US008637029B2

(12) United States Patent
Solinger

(10) Patent No.: US 8,637,029 B2
(45) Date of Patent: Jan. 28, 2014

(54) METHODS FOR THE TREATMENT OF GOUT

(75) Inventor: Alan M. Solinger, Oakland, CA (US)

(73) Assignee: XOMA Technology Ltd., Berkeley, CA (US)

( * ) Notice: Subject to any disclaimer, the term of this patent is extended or adjusted under 35 U.S.C. 154(b) by 0 days.

(21) Appl. No.: 12/338,957

(22) Filed: Dec. 18, 2008

(65) Prior Publication Data

US 2009/0181019 A1 Jul. 16, 2009

Related U.S. Application Data

(60) Provisional application No. 61/015,633, filed on Dec. 20, 2007, provisional application No. 61/059,378, filed on Jun. 6, 2008, provisional application No. 61/095,191, filed on Sep. 8, 2008.

(51) Int. Cl.
*A61K 45/00* (2006.01)
*A61K 39/395* (2006.01)
*A61K 38/00* (2006.01)
*C07K 1/00* (2006.01)
*C07K 16/00* (2006.01)

(52) U.S. Cl.
USPC ... 424/145.1; 424/85.2; 514/12.2; 530/387.1; 530/350

(58) Field of Classification Search
None
See application file for complete search history.

(56) References Cited

U.S. PATENT DOCUMENTS

| | | | |
|---|---|---|---|
| 4,762,914 A | 8/1988 | Auron et al. | |
| 4,766,069 A | 8/1988 | Auron et al. | |
| 4,772,685 A | 9/1988 | Schmidt et al. | |
| 4,935,343 A | 6/1990 | Allison et al. | |
| 5,001,057 A | 3/1991 | Auron et al. | |
| 5,077,219 A | 12/1991 | Auron et al. | |
| 5,122,459 A | 6/1992 | Conlon et al. | |
| 5,286,847 A | 2/1994 | Gehrke et al. | |
| 5,348,858 A | 9/1994 | Uetsuki et al. | |
| 5,474,899 A | 12/1995 | Lisi | |
| 5,484,887 A | 1/1996 | Kronheim et al. | |
| 5,510,462 A | 4/1996 | Auron et al. | |
| 5,658,570 A | 8/1997 | Newman et al. | |
| 5,681,933 A | 10/1997 | Auron et al. | |
| 5,766,886 A | 6/1998 | Studnicka et al. | |
| 5,789,185 A | 8/1998 | Lisi | |
| 5,869,619 A | 2/1999 | Studnicka | |
| 5,885,793 A | 3/1999 | Griffiths et al. | |
| 5,959,085 A | 9/1999 | Garrone et al. | |
| 6,899,878 B2 | 5/2005 | Graham et al. | |
| 7,531,166 B2 | 5/2009 | Masat et al. | |
| 7,582,742 B2 | 9/2009 | Masat et al. | |
| 7,632,490 B2 | 12/2009 | Vicary et al. | |
| 2003/0022869 A1 | 1/2003 | Wiemer et al. | |
| 2003/0026806 A1 | 2/2003 | Witte et al. | |
| 2003/0124617 A1 | 7/2003 | Gram et al. | |
| 2003/0166069 A1 | 9/2003 | Welcher et al. | |
| 2004/0023869 A1 | 2/2004 | Sims et al. | |
| 2004/0063913 A1 | 4/2004 | Gram et al. | |
| 2005/0084493 A1 | 4/2005 | Witte | |
| 2005/0152850 A1 | 7/2005 | Engebretson | |
| 2005/0186615 A1 | 8/2005 | Lin et al. | |
| 2005/0256197 A1 | 11/2005 | Engebretson | |
| 2006/0094663 A1 | 5/2006 | Chemtob | |
| 2007/0161559 A1 | 7/2007 | Petrilli et al. | |
| 2008/0292640 A1 | 11/2008 | Solinger et al. | |
| 2008/0300185 A1 | 12/2008 | Vicary | |

FOREIGN PATENT DOCUMENTS

| | | |
|---|---|---|
| EP | 0267611 B1 | 5/1993 |
| EP | 0161901 B1 | 12/1993 |
| EP | 0364778 B1 | 3/1996 |
| EP | 0569687 B1 | 8/2002 |
| WO | 9501997 B1 | 1/1995 |
| WO | 0216436 A2 | 2/2002 |
| WO | 03010282 A2 | 2/2003 |
| WO | 03034984 A2 | 5/2003 |
| WO | 03073982 A2 | 9/2003 |
| WO | 2004002512 A1 | 1/2004 |
| WO | 2004022718 A2 | 3/2004 |
| WO | 2004067568 A2 | 8/2004 |
| WO | 2004072116 A2 | 8/2004 |
| WO | 2005019259 A2 | 3/2005 |
| WO | 2005084696 A1 | 9/2005 |
| WO | 2006081139 A2 | 8/2006 |
| WO | 2007002261 A2 | 1/2007 |
| WO | 2007077042 A1 | 7/2007 |
| WO | 2007077261 A1 | 7/2007 |
| WO | 2008051496 A2 | 5/2008 |
| WO | 2008077145 A2 | 6/2008 |
| WO | 2009086003 A1 | 7/2009 |
| WO | 2009149370 A1 | 12/2009 |

OTHER PUBLICATIONS

Houghten et al. New Approaches to Immunization, Vaccines 86, Cold Spring Harbor Laboratory, p. 21-25, 1986.*
Abbott RD, Gout and coronary heart disease: the Framingham Study, J Clin Epidemiol. 41:237-242 (1988).
Abramson et al., Blocking the effects of IL-1 in rheumatoid arthritis protects bone and cartilage. Rheumatology 41:972-980 (2002).
Akahoshi et al., Recent advances in crystal-induced acute inflammation, Current Opinion in Rheumatology 19:146-150 (2007).
Aksentijevich et al., De Novo CIAS1 Mutations, Cytokine Activation, and Evidence for Genetic Heterogeneity in Patients with Neonatal-Onset Multisystem Inflammatory Disease (NOMID), Arthritis & Rheumatisn 46(12):3340-3348 (2002).
Alheim et al., Hyperresponsive febrile reactions to interleukin (IL) 1 alpha and IL-1 beta, and altered brain cytokine mRNA and serum cytokine levels in IL 1 beta deficient mice. Proc. Natl. Acad. Sci. 94:2681-2686 (1997).

(Continued)

Primary Examiner — Christine J Saoud
Assistant Examiner — Jegatheesan Seharaseyon
(74) Attorney, Agent, or Firm — Diane Wilcock; Jones Day

(57) ABSTRACT

Disclosed are methods for the treatment and/or prevention of gout, comprising administering to a subject an effective amount of anti-IL-1β antibody or fragment thereof.

20 Claims, 10 Drawing Sheets

(56) References Cited

OTHER PUBLICATIONS

Arend et al., Binding of IL-1a, IL-1 beta, and IL-1 receptor antagonist by soluble IL-1 receptors and levels of soluble IL-1 receptors in synovial fluids. J. Immunol. 153:4766-4774 (1994).

Arend, The balance between IL-1 and IL-1Ra in disease, Cytokine & Growth Factor Reviews 13:323-340 (2002).

Arnett FC, Edworthy SM, Bloch, et al., The American Rheumatism Association 1987 revised criteria for the classification of rhematoid arthritis. Arthritis and Rheumatism 31:315-324 (1988).

Bieber & Terkeltaub, On the Brink of Novel Therapeutic Options for an Ancient Disease, Arthritis & Rheumatism 50(8): 2400-2414 (2004).

Bloomgarden, Concepts of Insulin Resistence, Metabolic Syndrome and related Disorders, 3(4): 282-293 (2005).

Boraschi et al., A monoclonal antibody to the IL-1 beta peptide 163-171 blocks adjuvanticity but not pyrogenicity of IL-1 beta in vivo J. Immul. 143:131-134 (1989); Erratum in: J. Immunol. 143:1403 (1989).

Boraschi et al., Differential inhibition of IL-1BETA activities and receptor binding of monoclonal antibodies mapping within a discrete region of the protein. Lymphokine Cytokine Res. 10:377-384 (1991).

Boschan et al., Neonatal-Onset Multisystem Inflammatory Disease (NOMID) Due to a Novel S331R Mutation of the CIAS1 gene and Response to Interleukin-1 Receptor Antagonist Treatment, Am J Medical Genetics 240S:883-886 (2006).

Braddock & Quinn, Targeting IL-1 in Inflammatory Disease: New Opportunities for Therapeutic Intervention, Nature Reviews—Drug Discovery 3:1-10 (2004).

Bresinihan B. et al., Treatment of rheumatoid arthritis with recombinant human interleukin-1 receptor antagonist. Arthritis Rheum. 41(12):2196-2204 (1998).

Burls & Jobanputra, The trials of anakinra, Lancet 364:827-828 (2004).

Chen et al., My D88 dependent IL-1 receptor signalling in essential for gouty inflammation stimulated my monosodium urate crystals, J. Clin. Investig. 116(8):2262-2271 (2006).

Chevalier et al., Safety Study of Intraarticular Injection of Interleukin 1 Receptor Antagonist in Patients with Painful Knee Osteoarthritis: A Multicenter Study, J Rheumatology 32(7):1317-1323 (2005).

Choi HK et al., Purine-rich foods, dairy and protein intake, and the risk of gout in men. N. Engl J Med. (350):1093-1103 (2004).

Choy & Panayi, Cytokine Pathways and Joint Inflammation in Rheumatoid Arthritis, N Engl J Med 34(12):907-916 (2001).

Cronstein et al., The Inflammatory Process of Gout and its Treatment, Arthritis Research & Therapy 8(Suppl1):S3 (2006).

Darling et al., Kinetic Exclusion Assay Technology: Characterization of Molecular Interactions. Assay and Drug Dev. Tech. 2(6): 647-657 (2004).

Dayer, The pivotal role of interleukin-1 in the clinical manifestation of rheumatoid arthritis. Rheumatology 42 (Suppl2):ii3-ii10 (2003).

D'Ettorre et al., Functional epitope mapping of human interleukin-1Beta by surface plasmon resonance. Eur. Cytokine Netw. 8:161-171 (1997).

Di Giovine FS, Malawista SE, Nuki G, Duff GW, Interleukin1 (IL 1) as a mediator of crystal arthritis. Stimulation of T cell and synovial fibroblast mitogenesis by urate crystal-induced IL 1. J Immunol. 138(10):3213-3218 (1987).

Di Giovine et al., Urate Crystals Stimulate Production of Tumor Necrosis Factor Alpha from Human Blood Monocytes and Synovial Cells, J. Clin. Invest. 87:1375-1381 (1991).

Dinarello, C., Interleukin-1, inteleukin-1 receptor antagonist. Intern Rev Immunol. 16:457-499 (1998).

Dinarello et al., The production of antibody against human leukocytic pyrogen. J. Clin. Invest. 60:465-472 (1977).

Dinarello et al., Human leukocytic pyrogen: purification and development of a radioimmunoassay. Proc. Natl. Acad. Sci. USA 74:4624-4627 (1977).

Dinarello, C., Biologic basis for interleukin-1 in disease, Blood, J Amed Soc Hematology, 87(6):2095-2147 (1996).

Dinarello, C., Blocking IL-1 in systemic inflammation. J. Exp. Med. 201:1355-1359 (2005).

Dinarello, C., "IL-1 beta" in Cytokine Reference: A compendium of cytokines and other mediators of host defense. Academic Press 351-374 (2001).

Dinarello, The many worlds of reducing interleukin-1. Arthritis Rheum. 52:1960-1967 (2005).

Dinarello, Therapeutic strategies to reduce IL-1 activity in treating local and systemic inflammation. Curr. Opin. Pharmacol. 4(4):378-385 (2004).

Dinarello, Therapeutic strategies to reduce IL-1 activity in treating local and systemic inflammation, Current Opinion in Pharmacology 4:378-383 (2004).

Economides et al., Cytokine traps: multi-component, high affinity blockers of cytokine action, Nature Medicine 9 (1):47-52 (2003).

Eggebeen, Gout: An Update, Am. Family Physician 76(6):801-808, 811-812 (2007).

Emad et al., The Diagnostic dilemma of undifferentiated inflammatory synovitis of the knee joint/joints: a comprehensive approach, APLAR Journal of Rheumatology 10:182-189 (2007).

Evans et al., Mapping receptor binding sites in interleukin (IL)-1 receptor antagonist and IL-1 beta by site-directed mutagenesis. Identification of a single site in IL-1ra and two sites in IL-1 beta. J. Biol. Chem. 270:11477-11483 (1995).

Faggioni et al., ABX10-0031, a High Affinity Fully Human Anti-IL-1 beta Monoclonal Antibody for the Treatment of Inflammatory Disease. Abstract for Presentation at 7th World Congress of Inflammation. Aug. 20-24, 2005 (Melbourne, Australia).

Faggioni et al., IL-1 mediates leptin induction during inflammation, American Journal of Physiology-Regulatory 274:204-208 (1998).

Falasca, Metabolic diseases: gout, Clin. Dermatol. 24(6):298-508 (2006).

Fantuzzi, Adipose tissue, adipokines, and inflammation, J. Allergy Clin. Immunol. 115:911-919 (2005).

Fantuzzi et al., Effect of endotoxin in IL-1 beta deficient mice, Journal of Immunology 157:291-296 (1996).

Fantuzzi et al., Response to local inflammation of IL-1 beta converting enzyme-deficient mice, J Immunology 158:1818-1824 (1997).

Fantuzzi et al., Physiological and cyotkine responses in interleukin-1 beta deficient mice after zymosan-induced inflammation, American Journal of Physiology (1997).

Firestein GS, Rheumatiod Arthritis. ACPMedicine. 15(11):1-18 (2007).

Fitzgerald et al., Rapid Responses to Anakinra in Patients with Refractory Adult-Onset Still's Disease, Arthritis & Rheumatism 52(6):1794-1803 (2005).

Fredericks et al., Identification of potent human anti-IL-1 RI antagonist antibodies. Protein Eng. Des. Sel. 17:95-106 (2004).

Furst, Anakinra: Review of Recombinant Human Interleukin-1 Receptor Antagonist in the treatment of Rheumatoid Arthritis, Clinical Therapeutics 26(12):1960-1975 (2004).

Garrone et al., Generation and characterization of a human monoclonal autoantibody that acts as a high affinity interleukin-1 alpha specific inhibitor. Mol. Immunol. 33:649-658 (1996).

Geiger T et al., Neutralization of interleukin-1 beta activity in vivo with a monoclonal antibody alleviates collagen-induced arthritis in DBA/1 mice and prevents the associated acute-phase response. Clin Exp Rheumatol. 11 (5):515-522 (1993).

Genta et al., Systemic Rheumatoid Vascultis: A Review, Semin Arthritis Rheum 36:88-98 (2006).

Gershenwald et al., Interleukin 1 receptor blockage attenuates the host inflammatory response. Proc. Natl. Acad. Sci. USA 87:4966-4970 (1990).

Godinho, et al., Refractory adult onset Still's disease sucessfully treated with anakinra, Ann Rheum Dis 64:647-648 (2005).

Goldbach-Mansky et al., Neonatal-Onset Multisystem Inflammatory Disease responsive to Interlekin-1 beta Inhibition, N Engl J Med 355(6):581-592 (2006).

Goupille P et al., Safety and efficacy of intra-articular injection of IL-1 ra (IL-1 receptor antagonist) in patients with painful osteroarthritis of the knee: a multicenter, double blind study. Arthritis and Rheumatism 48(9) (2003).

(56) References Cited

OTHER PUBLICATIONS

Gracie et al, A proinflammatory role for IL-1 beta in rheumatoid arthritis. J. Clin. Invest. 104(10):1393-1401 (1999).
Grundy, S.M., Metabolic syndrome: connecting and reconciling cardiovascular and diabetes worlds, J. Am. Coli. Cardiol. 47:1093-1000 (2006).
Grutter, MG et al., A mutational analysis of receptor binding sites of interleukin-1 beta differences in binding of human interleukin-1 Beta muteins to human and mouse receptors. Protein Eng. 7:663-671 (1994).
Gruver D., Living with Rheumatoid Arthritis: Unmet Needs (2004).
Guerne et al., Inflammatory mircocrystals stimulate interleukin-6 production and secretion by human monocytes and synoviocytes. Arthritis and Rheumatism 32(11):1443-1452 (1989).
Guo et al., Fluorescence resonance energy transfer reveals interleukin (IL)-1-dependent aggregation of IL-1 type I receptors that correlate with receptor activation, J. Biol. Chem. 270:27562-27568 (1995).
Hallegua & Weisman, Potential therapeutic uses of interleukin 1 receptor antagonists in human diseases, Ann Rheum Dis 61:960-967 (2002).
Haraoui et al., Biological agents in the treatment of rheumatoid arthritis. Curr. Pharm. Biotechnol. 1:217-233 (2000).
Harris ED et al., Overview of the management of rheumatoid arthritis. UptoDate. Feb. 4, 2008.
Hawkins, Interleukin-1-Receptor Antagonist in the Muckle-Wells Syndrome, N Engl J Med 348(25):2583-2584 (2003).
Hawkins, Lack of association between the corticotrophin-releasing hormone locus and rheumatoid arthritis, Arthritis & Rheumatism, 50(8):2706-2709 (2004).
Hawkins, PN et al., Spectrum of clinical feature in Muckle-Wells syndrome and response to anakinra. Arthritis and Rheumatism. 50:607-612 92004).
Herzbeck et al., Functional and molecular characterization of a monoclonal antibody against the 165-186 peptide of human IL-1 beta. Scand. J. Immunol. 30:549-562 (1989).
Hochberg MC., Racial differences in the incidence of gout. The role of hypertension. Arthritis and Rheumatism 38:628-632 (1995).
Hoffman et al., Prevention of cold-associated acute inflammation in familial cold autoinflammatory syndrome by interleukin-1 receptor antagonist, Lancet 364:1779-1785 (2004).
Hull et al., The expanding spectrum of systemic autoinflammatory disorders and their rheumatic manifestations, Curr Opin Rheumatol 15:61-69 (2003).
Inoue K, Masuko-Hongo K., Okamoto M., Nishiota K., Efficacy of daily compared to intermittent administration of IL-1 RA for protection against bone and cartilage destruction in collagen-challenged mice. Clin Exp Rheumatol 21(1):33-39 (2003).
International Search Report dated May 12, 2009 for PCT/US2008/087519 filed Dec. 18, 2008.
Jackson et al., In vitro antibody maturation: Improvement of a high affinity, neutralizing antibody against IL-1 Beta. J. Immunol. 154:3310-3319 (1995).
Jacques, C. et al., The role of IL-1 and IL-Ra in joint inflammation and cartilage degradation. Vitam Horm 74:371-404 (2006).
Johnson et al., "Inhibition of vagally medicated immune-to-brain signalling by vanadyl sulfate speeds recovery from sickness", PNAS 102:15184-15189 (2005).
Joosten, L., et al., IL-1aBeta blockade prevents cartilage and bone destruction in murine type II collagen-induced arthritis, whereas TNF-a blockade only ameliorates joint inflammation. J. Immunol. 163:5049-5055 (1999).
Joosten, L., et al., Anticyotkine treatment of established type II collagen-induced arthritis in DBA/1 mice. A comparative study using anti-TNF alpha, anti-IL-1 alpha/beta, and IL-1 RA. Arthritis Rheum. 39(5): 797-809 (1996).
Kenney et al., Monoclonal antibodies to human recombinant interleukin 1 (IL1) beta: Quantitation of IL-1 beta and Inhibition of biological activity. J. Immunol. 138:4236-4242 (1987).
Keystone, E. & Strond, V., Emerging Therapies in Rheumatoid Arthritis IN: Kelley's Textbook of Rheumatology. Harris E., Jr., M.D., et al., eds. Philadelphia, Elsevier Saunders, 951-960 (chapter 62) (2005).
Khilko, et al., Measuring interactions of MHC Class I Molecules Using Surface Plasmon Resonance. J. Immun. Methods. 183:77-94 (1995).
Khovidhunkit, et al., Effects of infection and inflammation on lipo and lipoprotein metabolism; mechanisms and consequences to the host. J Lipid Research, 45:1169-1196 (2004).
Kim, K.Y., A literature review of the epidemiology and treatment of acute gout. Clin Ther 25:1593-1616 (2003).
Klemp, P., Gout is on the increase in New Zealand. Ann Rheum Dis 56:22-26 (1997).
Kobayashi, et al., Role of Interlekin-1 and Tumor Necrosis Factor in Matrix Degradation of Human Osteoarthritic Cartilage, Arthritis & Rheumatism, 52(1):128-135 (2005).
Kock et al., Characterization of a monoclonal antibody directed against the biologically active site of human interleukin 1. J. Exp. Med. 163:463-468 (1986).
Kozak et al., IL-6 and IL-1 beta in fever: studies using cytokine-deficient (knockout) mice, Annals of the New York Academy of Sciences 856:33-47 (1998).
Levesque et al., Activated T lymphocytes Regulate Hyalurnan Binding to Monocyte CD44 Via Production of IL-2 and IFN-y. J. Immuno. 166(1): 188-196 (2001).
Li et al., Expression of caspase-1 in synovial membrane-like interface tissue around loosened hip prostheses. Rheum. Int. 22:97-102 (2002).
Lichtman AH et al., Role of interleukin 1 in the activation of T lymphocytes. PNAS 85:9699-9703 (1988).
Lillicrap, Crystal arthritis: contemporary approaches to disease of antiquity. Clin Med, 7(1):60-64 (2007).
Lin et al., *Pseudomonas aeruginosa* Activates Human Mast Cells to Induce Neutrophil Transendothelial Migration Via Mast Cell-Derived IL-1a and beta. J. Immuno. 169:4522-4530 (2002).
Liote & EA, Recent developments in crystal-induced inflammation pathogenesis and management. Cur Rheum Rep, 9(3): 243-250 (2007).
Lipsky PE, Rheumatoid arthritis. In: Harrison's principles of internal medicine. Wilson, J., et al., eds. McGraw-Hill, Inc. 313:1880-1888 (1998).
Liu-Bryan et al., Innate Immunity Conferred by Toll-like Receptors 2 and 4 and Myeloid Differentiation Factor Expressions Pivotal to Monosodium Urate Monohydrate Crystal-Induced Inflammation, Arthritis & Rheumatism 52 (9):2936-2946 (2005).
Liu-Bryan et al., TLR2 Signaling in Chondrocytes Drives Calcium Pyrophosphate Dyhydrate and Monosodium Urate Crystal-Induced Nitric Oxide Generation, J. Immunology 174:5016-5023 (2005).
Lovell, O.J., et al., Preliminary evidence for bioactivity of IL-1 trap (rilonacept), a long acting IL-1 inhibitor, in systemic juvenile idiopathic arthritis (sJIA). Arthritis and Rheumatism 54(9): S325-6 (2006).
Lovell, et al., Interleukin-1 blockade by anakinra improves clinical systems in patients with neonatal-onset multisystem inflammatory disease, Arthritis and Rheumatism 52(4):1283-1286 (2005).
European Communication pursuant to Rules 161(1) and 162 EPC, for EP 08 866 346.3, mailed on Aug. 11, 2010, with International Preliminary Report on Patentability.
Response to Communication pursuant to Rules 161(1) and 162 EPC for EP Application No. 08 866 346.3 filed Sep. 21, 2010.
Roseff et al., "The Acute Phase Response in Gout," The Journal of Rheumatology, 1987, vol. 14, issue 5, pp. 974-977.
Taylor et al., "Toward a Valid Definition of Gout Flare: Results of Consensus Exercises Using Delphi Methodology ad Cognitive Mapping," Arthritis & Rheumatism (Arthritis Care & Research), vol. 16, No. 4, Apr. 15, 2009, pp. 535-543.
Lu et al. IL-1 beta epitope mapping using site-directed mutagenesis and hydrogen-deuterium exchange mass spectrometry analysis. Biochemistry 44:1 106-11114 (2005).
Luk & Simpkin, Epidemiology of Hyperuricemia and Gout, Am J Manag Care 11(15 SUP):S435-S442 (2005).

(56) References Cited

OTHER PUBLICATIONS

Martinon & Glimcher, Gout: new insights into an old disease, J Cin Investigation 116(8):2073-2075 (2006).
Martinon F et al., Gout-associated uric acid crystals activate the nalpinflammasome. Nature 440(9):237-241 (2006).
Massone et al., Mapping of Biologically Relevant Sites of Human IL-1 Using Monoclonal Antibodies. J Immuno 140 (11):3812-3816 (1988).
Matsubara et al., A Severe Case of Chronic Infantile Neurologic, Cutaneous, Articular Syndrome Treated with Biologic Agents, Arthritis & Rheumatism 54(7):2314-2320 (2006).
McGonagle et al.. Management of treatment resistent inflammation of acute on chronic tophaceous gout with anakinra. Ann. Rheum. Dis. 66:1683-1984 (2007).
McItntyre et al., Inhibition of interleukin1 (IL-1) binding and bioactivity in vitro and modulation of acute inflammation in vivo IL-1 receptor antagonist and anti-IL-1 receptor monoclonal antibody. J. Exp. Med. 173:931-939 (1991).
Moldovan et al., Diacerhein and Rhein reduce the ICE-induced IL-1 Beta and IL-1Beta activation in human osteoarthritic cartilage. Osteoarthritis and Cartilage, 8:186-196 (2000).
Nishimura, Akito et al., Attenuation of monosodium urate crystal-induced arthritis in rabbits by a neutralizing antibody against interieukin-8, J Leukocyte Biology 62(4):444-449 (1997).
Nuki G & Simkin PA, A concise history of gout and hyperuricemia and their treatment. Arthritis Research and Therapy 8(1):1-5 92006).
Osnes et al.. Inhibition of IL-1 induced tissue factor (TF) synthesis and procoagulant activity (PCA) in purified human monocyptes by IL-4, IL-10 and IL-13. Cytokine 8(11):822-827 (1996).
Pascual & Sivera, Therapeutic advances in gout, Curr Opin Rheumatol, 19(2).122-127 (2007).
Pascual et al., Role of interleukin-1 (IL-1) in the pathogenesis of systemic onset juvenile idiopathic arthritis and clinical response to IL-1 blockade. J. Exp. Med. 201:1479-1486 (2005).
Perrier, et al., IL-1 receptor antagonist in metabolic disease: Dr. Jekyll or Mr. Hyde?, FEBS Letters 580:6289-6294 (2006).
Petrilli & Martinon, The inflammasome, autoinflammatory diseases and gout, Joint Bone Spine 74:571-576 (2007).
Pope & Tschopp, The Role of Interleukin-1 and the Inflammasome in Gout, Arthritis and Rheumatism, 56 (10):3183-3188 (2007).
Punzi L. et al., Pro-inflammatory interleukins in the synovial fluid of rheumatoid arthritis associated with joint D hypermobility. Rheumatology. 40:202-204 (2001).
Ramos et al., Positive clinical and biochemical responses to anakinra in a 3-yr-old patient with cryopryin-associated periodic syndrome. Rheumattology 44.1072-1073 (2005).
Rose & Liu-Bryan, Innate immunity in triggering and resolution of acute gouty inflammation. Curr Rheumatol Rep, 8 (3):209-214 (2006).
Rudinskaya & Trock, Successful Treatment of a Patient with Refractory Adult-Onset till Disease with Anakinra, J Clin Rheumatology 9(5):330-335 (2003).
Ruggiero et al., Inhibitory activity of IL-1 receptor antagonist depends on the balance between binding capacity for IL-1 receptor type 1 and IL-1 receptor type II, J. Immunol. 158:3881-3887 (1997).

Schlesinger, Management of Acute and Chronic Gouty Arthritis, Drugs 64(21):2399-2416 (2004).
Schumacher & Chen, Newer therapeutic approaches: gout. Rheum Dis Clin North Am, 32(1):235-244 (2006).
Sennikov et al., Production of cytokines by immature erythroid cells derived from human embryonic live. Eur. Cytokine Netw. 12(2):214-279 (2001).
Simkin PA, The pathogenesis of podagra. Annals of Internal Medicine 86:230-233 (1977).
Simon P. et al., Mapping of neutralizing epitopes and the receptor binding site of human interleukin 1 beta, J Biological Chemistry, American Society of Biochemical Biologists 268(13):9771-9779 (1993).
Slack et al.. Independent binding of interleukin-1 alpha and interleukin-1 beta to type I and type II interleukin-1 receptors. J. Biol Chem 268:2513-2524 (1993).
Smith et al., A single amino acid difference between human and monkey interleukin (IL)-1 beta dictates effective binding to soluble type II IL-1 receptor. J. Biol. Chem, 277:47619-47625 (2002).
So et al., A pilot study of IL-1 inhibition by anakinra in acute gout, Arthritis Research & Therapy 9:R28 (2007).
Studnicka et al., Human-engineered monoclonal antibodies retain full specific binding activity by preserving non-CDR complementarity-modulating residues. Protein Engineering 7:805-814 (1994).
Svenson et al., Differential binding of human interleukin-1 (IL-1) receptor antagonist to natural and recombinant soluble and cellular IL-1 type I receptors, Eur. J. Immuol 25:2842-2850 (1995).
Terkeltaub et al., Monocyte-derived neutrophil chemotactic factor/interleukin-8 is a potential mediator of crystal-induced inflammation. Arthritis and Rheumatism 34(0:894-903 (1991).
Towbin et al., Neoepitope immunoassay: An assay for human interleukin 1 beta based on an antibody induced conformational change, J. Immunoassay 17:353-369 (1996).
Vigers et al., Crystal structure of the type-1 interleukin-1 receptor cornplexed with interleukin-1 beta. Nature 386:190-194 (1997).
Vigers et al., X-ray crystal structure of a small antagonist peptide bound to interleukin-1 receptor type 1. J. Biol. Chem. 215:36927-36933 (2000).
Wisse, The inflammatory syndrome: the ole of adipose tissue cytokines in metabolic disorders linked to obesity. J. Am. Soc. Nephrol. 15:2792-2800 (2004).
Wooley P.H., et al,, The effect of an interleukin-1 receptor antagonist protein on type II collagen-induced arthritis and antigen-induced arthritis in mice. Arthritis Rheum. 36(9):1305-1314 (1993).
Yanofsky et al., High affinity type I interleukin 1 receptor and antagonists discovered by screening recombinant peptide libraries Proc. Natl. Acad. Sci. USA 93:7381-7386 (1996).
Yoon; et al., Antibodies to Domains II and II of IL-1 Receptor Accessory Protein Inhibit IL-1Beta Activity But Not Binding: Regulation of IL-1 Responses Is Via Type I Receptor, Not the Accessory Protein, J. Immuno. 160:3170-3179 (1998).
Yoshiie, et al., Intracellular infection by the Human Granulocytic Ehrlichiosis Agent Inhibits Human Neutrophil Apoptosis, Infection and Immunity 68(3):1125-1133 (2000).
Zheng et al., Resistance to fever induction and impaired acute-phase response in interleukin-1 beta deficient mice. Immunity 3:9-19 (1995).

* cited by examiner

Figure 6

| Stimulant | Ab | IL-1β | IL-1a | IL-6 | IL-8 | IL-1Ra | TNFα | IFNγ |
|---|---|---|---|---|---|---|---|---|
| RPMI | 0 | 0.0 | 0.0 | 0.0 | 0.1 | 0.0 | 0.0 | 1.1 |
| RPMI | 10000 | 0.0 | 0.0 | 0.0 | 13.4 | 22.0 | 0.0 | 0.8 |
| Staph | 10000 | 0.0 | 31.7 | 45.6 | 93.6 | 79.7 | 52.6 | 22.1 |
| Staph | 1000 | 0.0 | 30.7 | 49.4 | 85.9 | 94.8 | 74.0 | 26.7 |
| Staph | 100 | 0.9 | 40.8 | 74.1 | 97.1 | 92.6 | 69.5 | 34.9 |
| Staph | 10 | 18.4 | 46.9 | 80.4 | 97.9 | 93.3 | 94.9 | 36.9 |
| Staph | 3 | 23.8 | 41.1 | 71.3 | 93.7 | 101.2 | 97.3 | 43.8 |
| Staph | 1 | 26.4 | 49.6 | 69.8 | 98.0 | 95.7 | 96.1 | 48.7 |
| Staph | 0.1 | 56.1 | 63.3 | 75.1 | 103.6 | 102.5 | 101.0 | 54.8 |
| Staph | 0 | 100.0 | 100.0 | 100.0 | 100.0 | 100.0 | 100.0 | 100.0 |

$T_\alpha$ = 1.42 days
$T_\beta$ = 22.0 days
CL = 2.54 mL/day/kg
$V_C$ = 41.3 mL/kg
$F_{alpha}$ = 0.061

LOQ = Limit of Quantification

METHODS FOR THE TREATMENT OF GOUT

This application claims benefit under 35 U.S.C. §119 of U.S. Provisional Application No. 61/015,633, filed Dec. 20, 2007, U.S. Provisional Application No. 61/059,378, filed Jun. 6, 2008, and U.S. Provisional Application No. 61/095,191, filed Sep. 8, 2008, the disclosures of which are herein incorporated by reference in their entirety.

FIELD OF INVENTION

The invention relates to methods and materials for the treatment and/or prevention of gout. Such methods and materials may be used to treat a subject suffering from gout or to prevent occurrence of the same in an at risk subject.

BACKGROUND OF THE INVENTION

The present disclosure is directed to methods and materials for the treatment and/or prevention of gout in a subject. Such methods and materials may be used to treat a mammalian (e.g., human) subject suffering from gout or to prevent occurrence of the same in an at risk subject.

Gout is a form of acute arthritis that causes severe pain and swelling in the joints. Gouty arthritis accounted for an estimated 3.9 million outpatient visits in the United States in 2002. Unlike other rheumatic diseases, the etiology of gout is well characterized, its pathophysiology is well understood, and the disease is easily diagnosed. For many patients, therapy with nonsteroidal anti-inflammatory drugs (NSAIDs) or corticosteroids for acute attacks and prevention of recurrence with agents that lower the serum uric acid levels are highly effective. However, these therapies are not sufficient for many patients with acute, chronic or refractory gout due to their lack of adequate clinical efficacy, associated toxicities, or because of co-morbid diseases.

Gout is precipitation of crystals into tissue, usually in and around joints, most often causing recurrent acute or chronic arthritis.

The disease is marked by deposits of monosodium urate (MSU) crystals into tissue, usually in and around the joints and in the synovial fluid and lining, and usually an excessive amount of uric acid in the blood. Intense joint inflammation occurs as white blood cells engulf the uric acid crystals, causing pain, heat, and redness of the joint tissues. Gouty arthritis is due to monosodium urate crystal-induced release of proinflammatory cytokines from leukocytes. Among the many cytokines implicated, IL-1 may have a special role in the inflammatory network, as MSU crystals stimulate IL-1 release by monocytes and synovial mononuclear cells. Acute gout flares usually come on suddenly, go away after 5 to 10 days, and can keep recurring.

IL-1β is a pro-inflammatory cytokine secreted by a number of different cell types including monocytes and macrophages. When released as part of an inflammatory reaction, IL-1β produces a range of biological effects, mainly mediated through induction of other inflammatory mediators such as corticotrophin, platelet factor-4, prostaglandin E2 (PGE2), IL-6, and IL-8. IL-1β induces both local and systemic inflammatory effects through the activation of the IL-1 receptor found on almost all cell types. The interleukin-1 (IL-1) family of cytokines has been implicated in a number of disease states. IL-1 family members include IL-1α, IL-1β, and IL-1Ra. Although related by their ability to bind to IL-1 receptors (IL-1R1 and IL-1R2), each of these cytokines is different, being expressed by a different gene and having a different primary amino acid sequence. Furthermore, the physiological activities of these cytokines can be distinguished from each other.

Experiments indicating the apparent involvement of IL-1β and other inflammatory mediators in gout have been published (see for example, Petrilli et al., Joint Bone Spine (2007) 74:571-576; Pope et al., Arthritis Rheum. (2007) 56:3183-3188; Chen et al., J. Clin. Invest. (2006) 116:2073-2075; Akahoshi, T., et al., Curr. Opin. Rheumatol. (2007) 19:146-150; Martinon, F., et al., Nature (2006) 440:237-241; and Cronstein et al., Arthritis Res. Ther. (2006) 8, Suppl. 1:S3). So et al., Arthritis Res. Ther. (2007) 9(2):R28 describe the use of a recombinant IL-1 receptor antagonist (IL-1Ra, anakinra) in an open label study for the treatment of acute gout, performed with daily dosing of 100 mg subcutaneously for 3 days. McGonagle, et al., Ann. Rheum. Dis. (2007) 66:1683-1684 describe the use of a recombinant IL-1 receptor antagonist (IL-1Ra, anakinra) for the treatment of gout in a patient receiving continuous daily subcutaneous doses of 100 mg. The daily dosing of injectable medications is generally undesirable and may result in problems with patient compliance, thereby decreasing effectiveness of this treatment modality/ or limiting its desirability. Thus, there remains a need for effective means to treat gout, particularly treatment compositions and methods that do not require frequent (e.g., daily) injections.

Because of the problems with current treatments, new therapies to treat gout are needed to replace or complement available pharmaceutical approaches. The present disclosure provides compositions and methods for the treatment of gout (e.g., acute gout, chronic gout, refractory gout). The methods disclosed herein comprise, for example, administering an anti-IL-1β antibody or fragment thereof. Methods that directly target the IL-1β ligand with an antibody, particularly antibodies that exhibit high affinity, provide advantages over other potential methods of treatment, such as IL-1β receptor antagonists (e.g., IL-1Ra, Anakinra). The challenge for IL-1 receptor antagonist-based therapeutics is the need for such therapeutics to occupy a large number of receptors, which is a formidable task since these receptors are widely expressed on all cells except red blood cells (Dinarello, Curr. Opin. Pharmacol. 4:378-385, 2004). In most immune-mediated diseases, such as the diseases disclosed herein, the amount of IL-1β cytokine that is measurable in body fluids or associated with activated cells is relatively low. Thus, a method of treatment and/or prevention that directly targets the IL-1β ligand should provide a superior strategy, particularly when administering an IL-1β antibody with high affinity.

SUMMARY OF THE INVENTION

The present disclosure is directed to compositions and methods for the treatment and/or prevention of gout in a subject. Such compositions and methods may be used to treat a mammalian subject (e.g., human) suffering from or at risk for gout. The methods and materials also may be used to prevent the occurrence of gout in an at risk subject.

In one aspect of the disclosure, a method of treating gout in a subject (e.g., human subject) is provided, the method comprising administering (e.g., in a therapeutically effective amount) an anti-IL-1β antibody or fragment thereof to the subject. In one embodiment of the disclosure, the gout is chronic gout. In another embodiment, the gout is acute gout. In yet another embodiment, the gout is refractory gout.

In another aspect, the disclosure provides a method of treating gout in a subject (e.g., human subject), the method comprising administering (e.g., in a therapeutically effective amount) an anti-IL-1β antibody or fragment thereof to the subject, wherein the dose of the antibody or fragment is sufficient to achieve at least a 50% reduction in joint pain. In one embodiment, the anti-IL-1β antibody or fragment thereof is sufficient to achieve at least a 60% reduction in joint pain, at least a 70% reduction in joint pain, at least a 80% reduction in joint pain, at least a 90% reduction in joint pain, at least a 95% reduction in joint pain or a 100% reduction in joint pain.

In another aspect of the disclosure, the dose of the antibody or fragment is sufficient to achieve at least a 20% decrease in C-reactive protein (CRP) levels, at least a 30% decrease in CRP levels, at least a 40% decrease in CRP levels, at least a 50% decrease in CRP levels, at least a 60% decrease in CRP levels, at least a 70% decrease in CRP levels, at least a 80% decrease in CRP levels, at least a 90% decrease in CRP levels.

In a preferred embodiment, the dose of the antibody or fragment is sufficient to achieve at least a 50% reduction in joint pain and at least a 20% decrease in CRP levels, at least a 30% decrease in CRP levels, at least a 40% decrease in CRP levels, at least a 50% decrease in CRP levels, at least a 60% decrease in CRP levels, at least a 70% decrease in CRP levels, at least a 80% decrease in CRP levels, and/or at least a 90% decrease in CRP levels.

In another aspect of the disclosure, the dose of the antibody or fragment is sufficient to achieve at least a 20% decrease in Erythrocyte Sedimentation Rate (ESR), at least a 40% decrease in ESR, at least a 50% decrease in ESR, at least a 60% decrease in ESR, at least a 70% decrease in ESR, at least a 80% decrease in ESR, at least a 90% decrease in ESR. In a preferred embodiment, the dose of the antibody or fragment is sufficient to achieve at least a 50% reduction in joint pain and at least a 20% decrease in ESR, at least a 40% decrease in ESR, at least a 50% decrease in ESR, at least a 60% decrease in ESR, at least a 70% decrease in ESR, at least a 80% decrease in ESR, and/or at least a 90% decrease in ESR In another aspect, the disclosure provides a method of treating gout in a subject (e.g., human subject), the method comprising administering (e.g., in a therapeutically effective amount) an anti-IL-1β antibody or fragment thereof to the subject, wherein the dose of the antibody or fragment is sufficient to achieve at least a 50% reduction in joint pain, at least a 20% decrease in CRP levels and at least a 20% decrease in ESR. In one embodiment, the dose of the antibody or fragment is sufficient to achieve at least a 50% reduction in joint pain, at least a 30% decrease in CRP levels and a 30% decrease in ESR. In another embodiment, the dose of the antibody or fragment is sufficient to achieve at least a 50% reduction in joint pain, at least a 40% decrease in CRP levels and a 40% decrease in ESR. In another embodiment, the dose of the anti-IL-1β antibody or fragment is sufficient to achieve at least a 60% reduction in joint pain, at least a 20% decrease in CRP levels and at least a 20% decrease in ESR. In another embodiment, the dose of the anti-IL-1β antibody or fragment is sufficient to achieve at least a 60% reduction in joint pain, at least a 40% decrease in CRP levels and at least a 40% decrease in ESR. In another embodiment, the dose of the anti-IL-1β antibody or fragment is sufficient to achieve at least a 60% reduction in joint pain, at least a 50% decrease in CRP levels and at least a 50% decrease in ESR. In yet another embodiment, the dose of the anti-IL-1β antibody or fragment is sufficient to achieve at least a 70% reduction in joint pain, at least a 20% decrease in CRP levels and at least a 20% decrease in ESR. In another embodiment, the dose of the anti-IL-1β antibody or fragment is sufficient to achieve at least a 70% reduction in joint pain, at least a 40% decrease in CRP levels and a 40% decrease in ESR. In another embodiment, the dose of the anti-IL-1β antibody or fragment is sufficient to achieve at least a 70% reduction in joint pain, at least a 50% decrease in CRP levels and at least a 50% decrease in ESR.

The anti-IL-1β antibodies or antibody fragments used in the methods of the disclosed herein generally bind to IL-1β with high affinity. In one preferred embodiment, the disclosure provides a method of treating gout in a subject (e.g., human subject), the method comprising administering (e.g., in a therapeutically effective amount) an anti-IL-1β antibody or fragment thereof to the subject, wherein, the antibody or antibody fragment binds to IL-1β with a dissociation constant of about 10 nM or less, about 5 nM or less, about 1 nM or less, about 500 pM or less, about 250 pM or less, about 100 pM or less, about 50 pM or less, or about 25 pM or less. In particularly preferred embodiments, the antibody or antibody fragment binds to human IL-1β with a dissociation constant of about 100 pM or less, about 50 pM or less, about 10 pM or less, about 5 pM or less, about 3 pM or less, about 1 pM or less, about 0.75 pM or less, about 0.5 pM or less, about 0.3 pM or less, about 0.2 pM or less, or about 0.1 pM or less.

In another aspect of the invention, the anti-IL-1β antibody or antibody fragment is a neutralizing antibody. In another aspect, the anti-IL-1β antibody or antibody fragment binds to an IL-1β epitope such that the bound antibody or fragment substantially permits the binding of IL-1β to IL-1 receptor I (IL-1RI). In another aspect, the anti-IL-1β antibody or antibody fragment binds to IL-1β, but does not substantially prevent the bound IL-1β from binding to IL-1 receptor I (IL-1RI). In another aspect, the antibody or antibody fragment does not detectably bind to IL-1α, IL-1R or IL-1Ra. In yet another aspect of the invention, the antibody or antibody fragment binds to an epitope contained in the sequence ESVDPKNYPKKKMEKRFVFNKIE (SEQ ID NO: 1). In another aspect, the antibody or fragment thereof competes with the binding of an antibody having the light chain variable region of SEQ ID NO:5 and the heavy chain variable region of SEQ ID NO:6

In yet another aspect of the invention, the antibody or antibody fragment binds to an epitope incorporating Glu64 of IL-1β. In yet another aspect of the invention, the antibody or antibody fragment binds to amino acids 1-34 of the N terminus of IL-1β. Preferably, the antibody or antibody fragment is human engineered, humanized or human.

In another aspect, the invention provides a method of treating a subject (e.g., mammal, human) displaying symptoms of, or at risk for, developing gout, the method comprising administering an anti-IL-1β antibody or fragment thereof to the subject in one or more doses.

In another aspect of the invention, a method is provided for treating gout in a subject (e.g., mammal, human), the method comprising administering an anti-IL-1β antibody or fragment thereof to the human, wherein administration of an initial dose of the IL-1β antibody or antibody fragment is followed by the administration of one or more subsequent doses. In one embodiment, administration of an initial dose of the antibody or antibody fragment is followed by the administration of two or more subsequent doses. In another embodiment, administration of an initial dose of the antibody or antibody fragment is followed by the administration of one or more subsequent doses, and wherein said one or more subsequent doses are in an amount that is approximately the same or less than the initial dose. In another embodiment, administration of an initial dose of the antibody or antibody fragment is followed by the administration of one or more subsequent doses, and wherein at least one of the subsequent doses is in an amount that is more than the initial dose. In yet another embodiment, administration of the antibody or antibody fragment is one time for each episode of acute gout. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In one embodiment, two or more, three or more, four or more, five or more, six or more, seven or more, eight or more, nine or more, ten or more or eleven or more subsequent doses of the antibody are administered. In another embodiment administration of the initial dose and each one or more subsequent doses are separated from each other by an interval of at least about two weeks, at least about three weeks, at least about one month, at least about two months, at least about three months, at least about four months, at least about five months, at least about six months, at least about seven months, at least about eight months, at least about nine months, at least about ten months, at least about eleven months, or at least about twelve months. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In another embodiment, the antibody or fragment is administered in one or more doses of 5 mg/kg or less of antibody or fragment, 3 mg/kg or less of antibody or fragment, 2 mg/kg or less of antibody or fragment, 1 mg/kg or less of antibody or fragment, 0.75 mg/kg or less of antibody or fragment, 0.5 mg/kg or less of antibody or fragment, 0.3 mg/kg or less of antibody or fragment, 0.1 mg/kg or less of antibody or fragment, 0.03 mg/kg or less of antibody or fragment, 0.01 mg/kg or less of antibody or fragment, 0.003 mg/kg or less of antibody or fragment or 0.001 mg/kg or less of antibody or fragment. Preferably, in each of the aforementioned embodiments, the antibody or fragment is administered in one or more doses of at least 0.01 mg/kg of antibody or fragment, at least 0.01 mg/kg of antibody or fragment, or at least 0.03 mg/kg of antibody or fragment. Preferably, the antibody or fragment is administered in one or more doses of 0.001 mg/kg to 1 mg/kg, 0.001 mg/kg to 0.3 mg/kg, 0.003 mg/kg to 1 mg/kg, 0.003 mg/kg to 0.3 mg/kg. The above dosage amounts refer to mg (antibody or fragment)/kg (weight of the individual to be treated). In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In another embodiment, the initial dose and one or more subsequent doses of antibody or fragment are each from about 0.01 mg/kg to about 10 mg/kg of antibody, from about 0.03 to about 1 mg/kg of antibody, from about 0.03 to about 0.3 mg/kg of antibody, from about 0.05 to about 5 mg/kg of antibody, from about 0.05 mg/kg to about 3 mg/kg of antibody, from about 0.1 mg/kg to about 3 mg/kg of antibody, from about 0.1 mg/kg to about 1 mg/kg of antibody, from about 0.1 mg/kg to about 0.5 mg/kg of antibody, from about 0.3 mg/kg to about 5 mg/kg of antibody, from about 0.3 mg/kg to about 3 mg/kg of antibody, from about 0.3 mg/kg to about 1 mg/kg of antibody, from about 0.5 mg/kg to about 5 mg/kg of antibody, from about 0.5 mg/kg to about 3 mg/kg of antibody, from about 0.5 mg/kg to about 1 mg/kg of antibody, from about 1 mg/kg to about 5 mg/kg of antibody, or from about 1 mg/kg to about 3 mg/kg of antibody. In certain embodiments, two or more, three or more, four or more, five or more, six or more, seven or more, eight or more, nine or more, ten or more or eleven or more subsequent doses of the antibody are administered. The above dosage amounts refer to mg (antibody or fragment)/kg (weight of the individual to be treated). The same applies hereinafter if a dosage amount is mentioned. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In another aspect, the invention provides a method of treating gout in a subject (e.g., human), the method comprising administering a therapeutically effective amount of an anti-IL-1β antibody or fragment thereof to the subject as an initial dose of about 5 mg/kg or less of antibody or fragment, 3 mg/kg or less of antibody or fragment, 2 mg/kg or less of antibody or fragment, 1 mg/kg or less of antibody or fragment, 0.75 mg/kg or less of antibody or fragment, 0.5 mg/kg or less of antibody or fragment, 0.3 mg/kg or less of antibody or fragment, 0.1 mg/kg or less of antibody or fragment, or 0.03 mg/kg or less of antibody or fragment, and a plurality of subsequent doses of antibody or fragment in an amount about the same or less than the initial dose. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

Preferably, in the aforementioned embodiments wherein the antibody or fragment is administered as an initial dose and a plurality of subsequent doses, the dose of antibody or fragment is at least 0.001 mg/kg of antibody or fragment, at least 0.003 mg/kg of antibody or fragment, at least 0.01 mg/kg of antibody or fragment, at least, 0.03 mg/kg of antibody or fragment, at least 0.05 mg/kg of antibody or fragment, or at least 0.09 mg/kg of antibody or fragment. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In yet another aspect of the invention, the antibody or fragment is administered as a fixed dose, independent of a dose per subject weight ratio. In one embodiment, the antibody or fragment is administered in one or more fixed doses of 1000 mg or less of antibody or fragment, 750 mg or less of antibody or fragment, 500 mg or less of antibody or fragment, 250 mg or less of antibody or fragment, 100 mg or less of antibody or fragment, about 25 mg or less of antibody or fragment, about 10 mg or less of antibody or fragment or about 1.0 mg or less of antibody or fragment. In another embodiment, the antibody or fragment is administered in one or more fixed doses of at least about 0.1 mg of antibody or fragment, at least about 1 mg of antibody or fragment, at least about 5 mg of antibody or fragment, or at least about 10 mg of antibody or fragment. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In certain embodiments, the fixed dose is from about 1 mg to about 10 mg, about 1 mg to about 25 mg, about 10 mg to about 25 mg, about 10 mg to about 50 mg, about 10 mg to about 100 mg, about 25 mg to about 50 mg, about 25 mg to about 100 mg, about 50 mg to about 100 mg, about 50 mg to about 150 mg, about 100 mg to about 150 mg, about 100 mg to about 200 mg, about 150 mg to about 200 mg, about 150 mg to about 250 mg, about 200 mg to about 250 mg, about 200 mg to about 300 mg, about 250 mg to about 300 mg, about 250 mg to about 500 mg, about 300 mg to about 400 mg, about 400 mg to about 500 mg, about 400 mg to about 600 mg, about 500 mg to about 750 mg, about 600 mg to about 750 mg, about 700 mg to about 800 mg, about 750 mg to about 1000 mg. In a preferred embodiment, the fixed dose is administered in one or more doses of about 0.1 mg to about 100 mg, about 1.0 mg to about 100 mg or about 1.0 mg to about 50 mg. In another preferred embodiment, the fixed dose is selected from the group consisting of about 1 mg to about 10 mg, about 1 mg to about 25 mg, about 10 mg to about 25 mg, about 10 mg to about 100 mg, about 25 mg to about 50 mg, about 50 mg to about 100 mg, about 100 mg to about 150 mg, about 150 mg to about 200 mg, about 200 mg to about 250 mg. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In another aspect, the invention provides a method of treating gout in a subject, the method comprising administering a therapeutically effective amount of an anti-IL-1β antibody or fragment thereof to the subject, wherein administration of an initial dose of the antibody or antibody fragment is followed by the administration of one or more subsequent doses, and wherein the plasma concentration of said antibody or antibody fragment in the human is permitted to decrease below a level of about 0.1 ug/mL for a period of time greater than about 1 week and less than about 6 months between administrations during a course of treatment with said initial dose and one or more subsequent doses. In one embodiment, the plasma concentration of said antibody or antibody fragment is permitted to decrease below a level of about 0.07 ug/mL, about 0.05 ug/mL, about 0.03 ug/mL or about 0.01 ug/mL for a period of time greater than about 1 week and less than about 5 months, about 4 months, about 3 months, about 2 months, about 1 month, about 3 weeks, or about 2 weeks between administrations. In one embodiment, these plasma values refer to values obtained for an individual that is treated with the antibody of fragment in accordance with the invention. In one embodiment, such an individual may be a patient suffering from gout. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

The invention contemplates that an anti-IL-1β antibody or fragment used in accordance with the methods herein may be administered in any of the aforementioned dose amounts, numbers of subsequent administrations, and dosing intervals between administrations, and that any of the disclosed dose amounts, numbers of subsequent administrations, and dosing intervals between administrations may be combined with each other in alternative regimens to modulate the therapeutic benefit. In certain embodiments, the one or more subsequent doses are in an amount that is approximately the same or less than the first dose administered. In another embodiment, the one or more subsequent doses are in an amount that is approximately more than the first dose administered. Preferably the anti-IL-1β antibody or fragment is administered by subcutaneous, intramuscular or intravenous injection. The invention contemplates that each dose of antibody or fragment may be administered at one or more sites. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In one embodiment, the anti-IL-1β antibody or fragment is administered in combination with at least one other medically accepted treatment for the disease, condition or complication. In another embodiment, the at least one other medically accepted treatment for the disease, condition or complication is reduced or discontinued, while treatment with the anti-IL-1β antibody or fragment is maintained at a constant dosing regimen. In another embodiment, the at least one other medically accepted treatment for the disease, condition or complication is reduced or discontinued, and treatment with the anti-IL-1β antibody or fragment is reduced. In another embodiment, the at least one other medically accepted treatment for the disease, condition or complication is reduced or discontinued, and treatment with the anti-IL-1β antibody or fragment is increased. In yet another embodiment, the at least one other medically accepted treatment for the disease, condition or complication is maintained and treatment with the anti-IL-1β antibody or fragment is reduced or discontinued. In yet another embodiment, the at least one other medically accepted treatment for the disease, condition or complication and treatment with the anti-IL-1β antibody or fragment are reduced or discontinued. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In another aspect, methods provided herein are in conjunction with at least one additional treatment method, said additional treatment method comprising administering at least one pharmaceutical composition comprising an active agent other than an IL-1β antibody or fragment. In yet another aspect, the methods prevent or delay the need for at least one additional treatment method, said additional treatment method comprising administering at least one pharmaceutical composition comprising an active agent other than an IL-1β antibody or fragment. In still another aspect, the methods reduce the amount, frequency or duration of at least one additional treatment method, said additional treatment method comprising administering at least one pharmaceutical composition comprising an active agent other than an IL-1β antibody or fragment. In yet another embodiment, treatment with the at least one active agent is maintained. In another embodiment, treatment with the at least one active agent is reduced or discontinued, while treatment with the anti-IL-1β antibody or fragment is maintained at a constant dosing regimen. In another embodiment, treatment with the at least one active agent is reduced or discontinued and treatment with the anti-IL-1β antibody or fragment is reduced. In another embodiment, treatment with the at least one active agent is reduced or discontinued, and treatment with the anti-IL-1β antibody or fragment is increased. In yet another embodiment, treatment with the at least one active agent is maintained and treatment with the anti-IL-1β antibody or fragment is reduced or discontinued. In yet another embodiment, treatment with the at least one active agent and treatment with the anti-IL-1β antibody or fragment are reduced or discontinued. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In another aspect, the invention provides a method of treating gout in a subject, the method comprising administering a therapeutically effective amount of an anti-IL-1β antibody or fragment thereof to the subject, wherein administration of an initial dose of the antibody or antibody fragment is followed by the administration of one or more subsequent doses, and wherein the plasma concentration of said antibody or antibody fragment in the human is maintained at a level of at least about 0.03 ug/mL, at least about 0.05 ug/mL, at least about 0.08 ug/mL, at least about 0.1 ug/mL, at least about 0.15 ug/mL, at least about 0.2 ug/mL, at least about 0.25 ug/mL, at least about 0.3 ug/mL, at least about 0.4 ug/mL, at least about 0.5 ug/mL, at least about 0.6 ug/mL, at least about 0.8 ug/mL, at least about 1 ug/mL, at least about 1.5 ug/mL, at least about 2 ug/mL, at least about 3 ug/mL, at least about 4 ug/mL, or at least about 5 ug/mL during a course of treatment with said initial dose and one or more subsequent doses. In one embodiment, these plasma values refer to values obtained for an individual that is treated with the antibody of fragment in accordance with the invention. In one embodiment, such an individual may be a patient suffering from gout. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In another aspect, the invention provides a method of treating gout in a subject, the method comprising administering a therapeutically effective amount of an anti-IL-1β antibody or fragment thereof to the subject, wherein the antibody or fragment thereof has a lower $IC_{50}$ than an IL-1β receptor antagonist in a human whole blood IL-1β inhibition assay that measures IL-1β induced production of IL-8. In one embodiment, the antibody or fragment has an $I_{50}$ that is less than about 90%, 80%, 70%, 60%, 50% of the $IC_{50}$ of an IL-1β receptor antagonist in a human whole blood IL-1β inhibition assay that measures IL-1β induced production of IL-8. In a further embodiment, the antibody or fragment has an $IC_{50}$ that is less than about 40%, 30%, 20%, 10% of the $IC_{50}$ of an IL-1β receptor antagonist in a human whole blood IL-1β inhibition assay that measures IL-1β induced production of IL-8. In a preferred embodiment, the antibody or fragment has an $I_{50}$ that is less than about 8%, 5%, 4%, 3%, 2%, 1% of the $IC_{50}$ of an IL-1β receptor antagonist in a human whole blood IL-1β inhibition assay that measures IL-1β induced production of IL-8. In one embodiment, the IL-1β receptor antagonist is anakinra (i.e., KINERET®). In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In another aspect, the invention provides a method of treating gout in a subject, the method comprising administering a therapeutically effective amount of an anti-IL-1β antibody or fragment thereof to the subject, wherein the antibody or fragment thereof provides in vivo inhibition of IL-1β stimulated release of IL-6 in mice compared to a control antibody using an assay that is described by Economides et al., *Nature Med.*, 9:47-52 (2003) which is incorporated by reference. In one embodiment the antibody or fragment provides in vivo inhibition of IL-8B stimulated release of IL-6 in mice of at least about 10%, 20%, 30%, 40%, 50% compared to the control antibody. In a further embodiment, the antibody or fragment provides in vivo inhibition of IL-1β stimulated release of IL-6 in mice of at least about 60%, 70%, 80%, 90%, 95% compared to the control antibody. In one embodiment, the control antibody is an isotype control antibody. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In another aspect, the invention provides a method of treating gout in a subject, the method comprising administering a therapeutically effective amount of an anti-IL-1β antibody or fragment thereof to the subject, wherein the antibody or fragment thereof inhibits *Staphylococcus epidermidis* induced cytokine production in human whole blood compared to a control where no antibody is used. In one embodiment the antibody or fragment provides a greater level of inhibition of *Staphylococcus epidermidis* induced cytokine production in human whole blood by at least about 10%, 20%, 30%, 40%, 50% compared to the control. In a further embodiment, the antibody or fragment provides a greater level of inhibition of *Staphylococcus epidermidis* induced cytokine production in human whole blood by at least about 60%, 70%, 80%, 90%, 95% compared to the control. In one embodiment, the inhibited cytokines are IL-1β, IL-1a, IL-6, IL-8, IL-1Ra, TNFα or IFNγ. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In another aspect, the invention discloses the use of an anti-IL-1β antibody or fragment thereof which as a lower $IC_{50}$ than an IL-1β receptor antagonist in a human whole blood IL-1β inhibition assay that measures IL-1β induced production of IL-8, in the manufacture of a composition for use in the treatment of gout. In one embodiment, the IL-1β receptor antagonist is anakinra (i.e., KINERET®). In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In another aspect of the invention, the use of the IL-1β antibodies or binding fragments is contemplated in the manufacture of a medicament for treating or preventing a disease or condition as disclosed herein. In any of the uses, the medicament can be coordinated with treatment using a second active agent. In another embodiment of the invention, the use of a synergistic combination of an antibody of the invention for preparation of a medicament for treating a patient exhibiting symptoms of at risk for developing a disease or condition as disclosed herein, wherein the medicament is coordinated with treatment using a second active agent is contemplated. Embodiments of any of the aforementioned uses are contemplated wherein the amount of the IL-1β binding antibody or fragment in the medicament is at a dose effective to reduce the dosage of second active agent required to achieve a therapeutic effect. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In yet another aspect of the invention, an article of manufacture is provided, comprising a container, a composition within the container comprising an anti-IL-1β antibody or fragment thereof, and a package insert containing instructions to administer the antibody or fragment to a human in need of treatment according to the aforementioned methods of the invention. In one embodiment, the container further comprises a pharmaceutically suitable carrier, excipient or diluent. In a related embodiment, the composition within the container further comprises a second active agent. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

Kits are also contemplated by the present invention. In one embodiment, a kit comprises a therapeutically or prophylactically effective amount of an anti-IL-1β antibody or fragment, packaged in a container, such as a vial or bottle, and further comprising a label attached to or packaged with the container, the label describing the contents of the container and providing indications and/or instructions regarding use of the contents of the container for treatment or prevention of a disease or condition according to the aforementioned methods of the invention. In one embodiment, the container further comprises a pharmaceutically suitable carrier, excipient or diluent. In a related embodiment, the container further contains a second active agent. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In one embodiment, the article of manufacture, kit or medicament is for the treatment or prevention of gout in a subject. In another embodiment, the instructions of a package insert of an article of manufacture or label of a kit comprise instructions for administration of the antibody or fragment according to any of the aforementioned dose amounts, numbers of subsequent administrations, and dosing intervals between administrations, as well as any combination of dose amounts numbers of subsequent administrations, and dosing intervals between administrations described herein. In yet another embodiment, the container of kit or article of manufacture is a pre-filled syringe. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

In another aspect of the disclosure, a method of treating monosodium urate (MSU) crystal-induced release of a pro-inflammatory cytokine in a subject (e.g., human subject) is provided, the method comprising administering a therapeutically effective amount of an anti-IL-1β antibody or fragment thereof to the subject. In one embodiment, the pro-inflammatory cytokine is IL-1β. In another embodiment, the pro-inflammatory cytokine is IL-6. In these embodiments, one may use, for example, an antibody or antibody fragment (e.g., a neutralizing antibody) which binds IL-1β with a dissociation constant of less than 100 pM. Such an antibody or fragment thereof may compete with the binding of an antibody having the light chain variable region of SEQ ID NO:5 and the heavy chain variable region of SEQ ID NO:6 to IL-1β.

It is to be understood that where the present specification mentions methods of treatments making use of antibodies or fragments thereof with certain properties (such as Kd values or $IC_{50}$ values), this also means to embody the use of such antibodies or fragments thereof in the manufacture of a medicament for use in these methods. Further, the invention also encompasses antibodies or fragments thereof having these properties as well as pharmaceutical compositions comprising these antibodies or fragments thereof for use in the methods of treatment discussed hereinafter.

BRIEF DESCRIPTION OF THE DRAWINGS

FIG. 6 is a table showing reduction of *Staphyloccus epidermidis*-induced cytokine production in human whole blood by treatment with an anti-IL-1β antibody.

DETAILED DESCRIPTION

Figure 1:
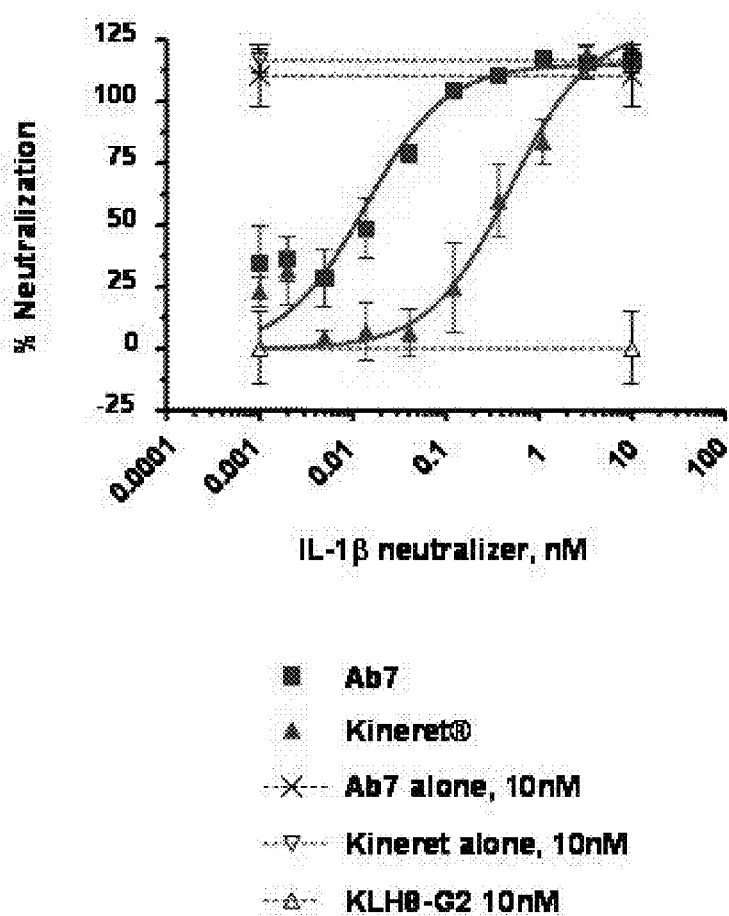
FIG. 1 is a graph showing the results of an in vitro IL-1β inhibition experiment for the antibody designated AB7 and for KINERET® (anakinra) involving IL-1β induced production of IL-8.

The present disclosure is directed to methods and related articles of manufacture for the treatment of gout (e.g., acute gout, chronic gout, refractory gout) in a subject, the method comprising administering to the subject one or more doses of an anti-IL-1β antibody or fragment thereof. Because of the problems with current treatments, new therapies to treat gout are needed to replace or complement available pharmaceutical approaches. The methods disclosed herein comprise, for example, administering an anti-IL- IL-1β antibody or fragment thereof. Methods that directly target the IL-1β ligand with an antibody, particularly antibodies that exhibit high affinity, provide advantages over other potential methods of treatment, such as IL-1β receptor antagonists (e.g., IL-1Ra, KINERET® (anakinra)). The challenge for IL-1 receptor antagonist-based therapeutics is the need for such therapeutics to occupy a large number of receptors, which is a formidable task since these receptors are widely expressed on all cells except red blood cells (Dinarello, Curr. Opin. Pharmacol. 4:378-385, 2004). In most immune-mediated diseases, such as the diseases disclosed herein, the amount of IL-1β cytokine that is measurable in body fluids or associated with activated cells is relatively low. As illustrated in Examples below, we have surprisingly found that antibodies, such as those disclosed herein, can be used to achieve the desired level of activity over a broad range of doses, including at very low doses. Thus, a method of treatment and/or prevention that directly targets the IL-1β ligand should provide a superior strategy.

IL-1β is a pro-inflammatory cytokine secreted by a number of different cell types including monocytes and macrophages. When released as part of an inflammatory reaction, IL-1β produces a range of biological effects, mainly mediated through induction of other inflammatory mediators such as corticotrophin, platelet factor-4, prostaglandin E2 (PGE2), IL-6, and IL-8. IL-1β induces both local and systemic inflammatory effects through the activation of the IL-1 receptor found on almost all cell types.

The interleukin-1 (IL-1) family of cytokines has been implicated in several disease states such as rheumatoid arthritis (RA), osteoarthritis, Crohn's disease, ulcerative colitis (UC), septic shock, chronic obstructive pulmonary disease (COPD), asthma, graft versus host disease, atherosclerosis, adult T-cell leukemia, multiple myeloma, multiple sclerosis, stroke, and Alzheimer's disease. IL-1 family members include IL-1α, IL-1β, and IL-1Ra. Although related by their ability to bind to IL-1 receptors (IL-1R1, IL-1R2), each of these cytokines is expressed by a different gene and has a different primary amino acid sequence. Furthermore, the physiological activities of these cytokines can be distinguished from each other.

Compounds that disrupt IL-1 receptor signaling have been investigated as therapeutic agents to treat IL-1 mediated diseases, such as for example some of the aforementioned diseases. These compounds include recombinant IL-1Ra (Amgen Inc., Thousand Oaks, Calif.), IL-1 receptor "trap" peptide (Regeneron Inc., Tarrytown, N.Y.), as well as animal-derived IL-1β antibodies and recombinant IL-1β antibodies and fragments thereof.

As noted above, IL-1 receptor antagonist (IL-1Ra) polypeptide has been suggested for use in the treatment of gout (So et al., 2007, ibid; McGonagle et al., 2007, ibid), but there remains a need for effective means to treat gout, particularly those that do not require daily, repeated injections. An additional challenge for IL-1 receptor antagonist-based therapeutics is the need for such therapeutics to occupy a large number of receptors, which is a formidable task since these receptors are widely expressed on all cells except red blood cells (Dinarello, Curr. Opin. Pharmacol. 4:378-385, 2004). In most immune-mediated diseases, such as the diseases disclosed herein, the amount of IL-1β cytokine that is measurable in body fluids or associated with activated cells is relatively low. Thus, a method of treatment and/or prevention that directly targets the IL-1β ligand is a superior strategy, particularly when administering an IL-1β antibody with high affinity.

The present invention provides methods and related compositions and articles of manufacture for the treatment and/or prevention of gout in a subject (e.g., mammalian, human), using an antibody or fragment thereof specific for IL-1β.

As shown in Example 1 below, we have surprisingly found that such an antibody (e.g., with very high affinity) can be far more potent an inhibitor of the IL-1 pathway than is IL-Ra (e.g., KINERET® (anakinra)), and provides an opportunity to achieve a therapeutic effect at a lower dose and/or with less frequent administration than necessary for other drugs, such as recombinant IL-1Ra.

Such methods as described herein with an IL-1β antibody or fragment may include the treatment of a subject suffering from gout (e.g., acute gout, chronic gout, refractory gout). The methods also may include preventing the occurrence of gout (e.g., acute gout, chronic gout, refractory gout) in an at risk subject.

Antibodies, Humanized Antibodies, and Human Engineered Antibodies

The IL-1 (e.g., IL-1β) binding antibodies of the present invention may be provided as polyclonal antibodies, monoclonal antibodies (mAbs), recombinant antibodies, chimeric antibodies, CDR-grafted antibodies, fully human antibodies, single chain antibodies, and/or bispecific antibodies, as well as fragments, including variants and derivatives thereof, provided by known techniques, including, but not limited to enzymatic cleavage, peptide synthesis or recombinant techniques.

Antibodies generally comprise two heavy chain polypeptides and two light chain polypeptides, though single domain antibodies having one heavy chain and one light chain, and heavy chain antibodies devoid of light chains are also contemplated. There are five types of heavy chains, called alpha, delta, epsilon, gamma and mu, based on the amino acid sequence of the heavy chain constant domain. These different types of heavy chains give rise to five classes of antibodies, IgA (including $IgA_1$ and $IgA_2$), IgD, IgE, IgG and IgM, respectively, including four subclasses of IgG, namely $IgG_1$, $IgG_2$, $IgG_3$ and $IgG_4$. There are also two types of light chains, called kappa (κ) or lambda (λ) based on the amino acid sequence of the constant domains. A full-length antibody includes a constant domain and a variable domain. The constant region need not be present in an antigen binding fragment of an antibody. Antigen binding fragments of an antibody disclosed herein can include Fab, Fab', F(ab')$_2$, and F(v) antibody fragments. As discussed in more detail below, IL-1β binding fragments encompass antibody fragments and antigen-binding polypeptides that will bind IL-1β.

Each of the heavy chain and light chain sequences of an antibody, or antigen binding fragment thereof, includes a variable region with three complementarity determining regions (CDRs) as well as non-CDR framework regions (FRs). The terms "heavy chain" and "light chain," as used herein, mean the heavy chain variable region and the light chain variable region, respectively, unless otherwise noted. Heavy chain CDRs are referred to herein as CDR-H1, CDR-H2, and CDR-H3. Light chain CDRs are referred to herein as CDR-L1, CDR-L2, and CDR-L3. Variable regions and CDRs in an antibody sequence can be identified (i) according to general rules that have been developed in the art or (ii) by aligning the sequences against a database of known variable regions. Methods for identifying these regions are described in Kontermann and Dubel, eds., *Antibody Engineering*, Springer, New York, N.Y., 2001, and Dinarello et al., *Current Protocols in Immunology*, John Wiley and Sons Inc., Hoboken, N.J., 2000. Databases of antibody sequences are described in and can be accessed through "The Kabatman" database at www.bioinf.org.uk/abs (maintained by A. C. Martin in the Department of Biochemistry & Molecular Biology University College London, London, England) and VBASE2 at www.vbase2.org, as described in Retter et al., *Nucl. Acids Res.*, 33(Database issue): D671-D674 (2005). The "Kabatman" database web site also includes general rules of thumb for identifying CDRs. The term "CDR," as used herein, is as defined in Kabat et al., *Sequences of Immunological Interest*, 5$^{th}$ ed., U.S. Department of Health and Human Services, 1991, unless otherwise indicated.

Polyclonal antibodies are preferably raised in animals by multiple subcutaneous (sc) or intraperitoneal (ip) injections of the relevant antigen and an adjuvant. An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later, the animals are boosted with ⅕ to {fraction (1/10)} the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibody refers to an antibody obtained from a population of substantially homogeneous antibodies. Monoclonal antibodies are generally highly specific, and may be directed against a single antigenic site, in contrast to conventional (polyclonal) antibody preparations that typically include different antibodies directed against different determinants (epitopes). In addition to their specificity, the monoclonal antibodies are advantageous in that they are synthesized by the homogeneous culture, uncontaminated by other immunoglobulins with different specificities and characteristics.

Monoclonal antibodies to be used in accordance with the present invention may be made by the hybridoma method first described by Kohler et al., (*Nature*, 256:495-7, 1975), or may be made by recombinant DNA methods (see, e.g., U.S. Pat. No. 4,816,567). The monoclonal antibodies may also be isolated from phage antibody libraries using the techniques described in, for example, Clackson et al., (*Nature* 352:624-628, 1991) and Marks et al., (*J. Mol. Biol.* 222:581-597, 1991).

In the hybridoma method, a mouse or other appropriate host animal, such as a hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, *J. Immunol.*, 133: 3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by Scatchard analysis (Munson et al., Anal. Biochem., 107:220 (1980)).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, DMEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

It is further contemplated that antibodies of the invention may be used as smaller antigen binding fragments of the antibody well-known in the art and described herein.

The present invention encompasses IL-1 (e.g., IL-1β) binding antibodies that include two full length heavy chains and two full length light chains. Alternatively, the IL-1β binding antibodies can be constructs such as single chain antibodies or "mini" antibodies that retain binding activity to IL-1β. Such constructs can be prepared by methods known in the art such as, for example, the PCR mediated cloning and assembly of single chain antibodies for expression in *E. coli* (as described in Antibody Engineering, The practical approach series, J. McCafferty, H. R. Hoogenboom, and D. J. Chiswell, editors, Oxford University Press, 1996). In this type of construct, the variable portions of the heavy and light chains of an antibody molecule are PCR amplified from cDNA. The resulting amplicons are then assembled, for example, in a second PCR step, through a linker DNA that encodes a flexible protein linker composed of the amino acids Gly and Ser. This linker allows the variable heavy and light chain portions to fold in such a way that the antigen binding pocket is regenerated and antigen is bound with affinities often comparable to the parent full-length dimeric immunoglobulin molecule.

The IL-1 (e.g., IL-1β) binding antibodies and fragments of the present invention encompass variants of the exemplary antibodies, fragments and sequences disclosed herein. Variants include peptides and polypeptides comprising one or more amino acid sequence substitutions, deletions, and/or additions that have the same or substantially the same affinity and specificity of epitope binding as one or more of the exemplary antibodies, fragments and sequences disclosed herein. Thus, variants include peptides and polypeptides comprising one or more amino acid sequence substitutions, deletions, and/or additions to the exemplary antibodies, fragments and sequences disclosed herein where such substitutions, deletions and/or additions do not cause substantial changes in affinity and specificity of epitope binding. For example, a variant of an antibody or fragment may result from one or more changes to an antibody or fragment, where the changed antibody or fragment has the same or substantially the same affinity and specificity of epitope binding as the starting sequence. Variants may be naturally occurring, such as allelic or splice variants, or may be artificially constructed. Variants may be prepared from the corresponding nucleic acid molecules encoding said variants. Variants of the present antibodies and IL-1β binding fragments may have changes in light and/or heavy chain amino acid sequences that are naturally occurring or are introduced by in vitro engineering of native sequences using recombinant DNA techniques. Naturally occurring variants include "somatic" variants which are generated in vivo in the corresponding germ line nucleotide sequences during the generation of an antibody response to a foreign antigen.

Variants of IL-1 (e.g., IL-1β) binding antibodies and binding fragments may also be prepared by mutagenesis techniques. For example, amino acid changes may be introduced at random throughout an antibody coding region and the resulting variants may be screened for binding affinity for IL-1β or for another property. Alternatively, amino acid changes may be introduced in selected regions of an IL-1β antibody, such as in the light and/or heavy chain CDRs, and/or in the framework regions, and the resulting antibodies may be screened for binding to IL-1β or some other activity. Amino acid changes encompass one or more amino acid substitutions in a CDR, ranging from a single amino acid difference to the introduction of multiple permutations of amino acids within a given CDR, such as CDR3. In another method, the contribution of each residue within a CDR to IL-1β binding may be assessed by substituting at least one residue within the CDR with alanine. Lewis et al. (1995), Mol. Immunol. 32: 1065-72. Residues which are not optimal for binding to IL-1β may then be changed in order to determine a more optimum sequence. Also encompassed are variants generated by insertion of amino acids to increase the size of a CDR, such as CDR3. For example, most light chain CDR3 sequences are nine amino acids in length. Light chain sequences in an antibody which are shorter than nine residues may be optimized for binding to IL-1β by insertion of appropriate amino acids to increase the length of the CDR.

Variants may also be prepared by "chain shuffling" of light or heavy chains. Marks et al. (1992), Biotechnology 10: 779-83. A single light (or heavy) chain can be combined with a library having a repertoire of heavy (or light) chains and the resulting population is screened for a desired activity, such as binding to IL-1β. This permits screening of a greater sample of different heavy (or light) chains in combination with a single light (or heavy) chain than is possible with libraries comprising repertoires of both heavy and light chains.

The IL-1 (e.g., IL-1β) binding antibodies and fragments of the present invention encompass derivatives of the exemplary antibodies, fragments and sequences disclosed herein. Derivatives include polypeptides or peptides, or variants, fragments or derivatives thereof, which have been chemically modified. Examples include covalent attachment of one or more polymers, such as water soluble polymers, N-linked, or O-linked carbohydrates, sugars, phosphates, and/or other such molecules. The derivatives are modified in a manner that is different from naturally occurring or starting peptide or polypeptides, either in the type or location of the molecules attached. Derivatives further include deletion of one or more chemical groups which are naturally present on the peptide or polypeptide.

The IL-1β binding antibodies and fragments of the present invention can be bispecific. Bispecific antibodies or fragments can be of several configurations. For example, bispecific antibodies may resemble single antibodies (or antibody fragments) but have two different antigen binding sites (variable regions). Bispecific antibodies can be produced by chemical techniques (Kranz et al. (1981), Proc. Natl. Acad. Sci. USA, 78: 5807), by "polydoma" techniques (U.S. Pat. No. 4,474,893) or by recombinant DNA techniques. Bispecific antibodies of the present invention can have binding specificities for at least two different epitopes, at least one of which is an epitope of IL-1β. The IL-1β binding antibodies and fragments can also be heteroantibodies. Heteroantibodies are two or more antibodies, or antibody binding fragments (Fab) linked together, each antibody or fragment having a different specificity.

Techniques for creating recombinant DNA versions of the antigen-binding regions of antibody molecules which bypass the generation of monoclonal antibodies are contemplated for the present IL-1 (e.g., IL-1β) binding antibodies and fragments. DNA is cloned into a bacterial expression system. One example of such a technique suitable for the practice of this invention uses a bacteriophage lambda vector system having a leader sequence that causes the expressed Fab protein to migrate to the periplasmic space (between the bacterial cell membrane and the cell wall) or to be secreted. One can rapidly generate and screen great numbers of functional Fab fragments for those which bind IL-1β. Such IL-1β binding agents (Fab fragments with specificity for an IL-1β polypeptide) are specifically encompassed within the IL-1β binding antibodies and fragments of the present invention.

The present IL-1 (e.g., IL-1β) binding antibodies and fragments can be humanized or human engineered antibodies. As used herein, a humanized antibody, or antigen binding fragment thereof, is a recombinant polypeptide that comprises a portion of an antigen binding site from a non-human antibody and a portion of the framework and/or constant regions of a human antibody. A human engineered antibody or antibody fragment is a non-human (e.g., mouse) antibody that has been engineered by modifying (e.g., deleting, inserting, or substituting) amino acids at specific positions so as to reduce or eliminate any detectable immunogenicity of the modified antibody in a human.

Humanized antibodies include chimeric antibodies and CDR-grafted antibodies. Chimeric antibodies are antibodies that include a non-human antibody variable region linked to a human constant region. Thus, in chimeric antibodies, the variable region is mostly non-human, and the constant region is human. Chimeric antibodies and methods for making them are described in Morrison, et al., *Proc. Natl. Acad. Sci. USA*, 81: 6841-6855 (1984), Boulianne, et al., *Nature*, 312: 643-646 (1984), and PCT Application Publication WO 86/01533. Although, they can be less immunogenic than a mouse monoclonal antibody, administrations of chimeric antibodies have been associated with human anti-mouse antibody responses (HAMA) to the non-human portion of the antibodies. Chimeric antibodies can also be produced by splicing the genes from a mouse antibody molecule of appropriate antigen-binding specificity together with genes from a human antibody molecule of appropriate biological activity, such as the ability to activate human complement and mediate ADCC. Morrison et al. (1984), Proc. Natl. Acad. Sci., 81: 6851; Neuberger et al. (1984), Nature, 312: 604. One example is the replacement of a Fc region with that of a different isotype.

CDR-grafted antibodies are antibodies that include the CDRs from a non-human "donor" antibody linked to the framework region from a human "recipient" antibody. Generally, CDR-grafted antibodies include more human antibody sequences than chimeric antibodies because they include both constant region sequences and variable region (framework) sequences from human antibodies. Thus, for example, a CDR-grafted humanized antibody of the invention can comprise a heavy chain that comprises a contiguous amino acid sequence (e.g., about 5 or more, 10 or more, or even 15 or more contiguous amino acid residues) from the framework region of a human antibody (e.g., FR-1, FR-2, or FR-3 of a human antibody) or, optionally, most or all of the entire framework region of a human antibody. CDR-grafted antibodies and methods for making them are described in, Jones et al., *Nature*, 321: 522-525 (1986), Riechmann et al., *Nature*, 332: 323-327 (1988), and Verhoeyen et al., *Science*, 239: 1534-1536 (1988)). Methods that can be used to produce humanized antibodies also are described in U.S. Pat. Nos. 4,816,567, 5,721,367, 5,837,243, and 6,180,377. CDR-grafted antibodies are considered less likely than chimeric antibodies to induce an immune reaction against non-human antibody portions. However, it has been reported that framework sequences from the donor antibodies are required for the binding affinity and/or specificity of the donor antibody, presumably because these framework sequences affect the folding of the antigen-binding portion of the donor antibody. Therefore, when donor, non-human CDR sequences are grafted onto unaltered human framework sequences, the resulting CDR-grafted antibody can exhibit, in some cases, loss of binding avidity relative to the original non-human donor antibody. See, e.g., Riechmann et al., *Nature*, 332: 323-327 (1988), and Verhoeyen et al., *Science*, 239: 1534-1536 (1988).

Human engineered antibodies include for example "veneered" antibodies and antibodies prepared using HUMAN ENGINEERING™ technology (see for example, U.S. Pat. Nos. 5,766,886 and 5,869,619). HUMAN ENGINEERING™ technology is commercially available, and involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk", "moderate risk", or "high risk" residues. The classification is performed using a global risk/reward calculation that evaluates the predicted benefits of making particular substitution (e.g., for immunogenicity in humans) against the risk that the substitution will affect the resulting antibody's folding and/or antigen-binding properties. Thus, a low risk position is one for which a substitution is predicted to be beneficial because it is predicted to reduce immunogenicity without significantly affecting antigen binding properties. A moderate risk position is one for which a substitution is predicted to reduce immunogenicity, but is more likely to affect protein folding and/or antigen binding. High risk positions contain residues most likely to be involved in proper folding or antigen binding. Generally, low risk positions in a non-human antibody are substituted with human residues, high risk positions are rarely substituted, and humanizing substitutions at moderate risk positions are sometimes made, although not indiscriminately. Positions with prolines in the non-human antibody variable region sequence are usually classified as at least moderate risk positions.

The particular human amino acid residue to be substituted at a given low or moderate risk position of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., *Protein Engineering*, 7: 805-814 (1994), U.S. Pat. Nos. 5,766,886, 5,770,196, 5,821,123, and 5,869,619, and PCT Application Publication WO 93/11794.

"Veneered" antibodies are non-human or humanized (e.g., chimeric or CDR-grafted antibodies) antibodies that have been engineered to replace certain solvent-exposed amino acid residues so as to further reduce their immunogenicity or enhance their function. As surface residues of a chimeric antibody are presumed to be less likely to affect proper antibody folding and more likely to elicit an immune reaction, veneering of a chimeric antibody can include, for instance, identifying solvent-exposed residues in the non-human framework region of a chimeric antibody and replacing at least one of them with the corresponding surface residues from a human framework region.

Veneering can be accomplished by any suitable engineering technique, including the use of the above-described HUMAN ENGINEERING™ technology.

In a different approach, a recovery of binding avidity can be achieved by "de-humanizing" a CDR-grafted antibody. De-humanizing can include restoring residues from the donor antibody's framework regions to the CDR grafted antibody, thereby restoring proper folding. Similar "de-humanization" can be achieved by (i) including portions of the "donor" framework region in the "recipient" antibody or (ii) grafting portions of the "donor" antibody framework region into the recipient antibody (along with the grafted donor CDRs).

For a further discussion of antibodies, humanized antibodies, human engineered, and methods for their preparation, see Kontermann and Dubel, eds., *Antibody Engineering*, Springer, New York, N.Y., 2001.

Exemplary humanized or human engineered antibodies include IgG, IgM, IgE, IgA, and IgD antibodies. The present antibodies can be of any class (IgG, IgA, IgM, IgE, IgD, etc.) or isotype and can comprise a kappa or lambda light chain. For example, a human antibody can comprise an IgG heavy chain or defined fragment, such as at least one of isotypes, IgG1, IgG2, IgG3 or IgG4. As a further example, the present antibodies or fragments can comprise an IgG1 heavy chain and an IgG1 light chain.

The present antibodies and fragments can be human antibodies, such as antibodies which bind IL-1β polypeptides and are encoded by nucleic acid sequences which are naturally occurring somatic variants of human germline immunoglobulin nucleic acid sequence, and fragments, synthetic variants, derivatives and fusions thereof. Such antibodies may be produced by any method known in the art, such as through the use of transgenic mammals (such as transgenic mice) in which the native immunoglobulin repertoire has been replaced with human V-genes in the mammal chromosome. Such mammals appear to carry out VDJ recombination and somatic hypermutation of the human germline antibody genes in a normal fashion, thus producing high affinity antibodies with completely human sequences.

Human antibodies to target protein can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598 6,657,103 and 6,833,268.

Using a transgenic animal described above, an immune response can be produced to a selected antigenic molecule, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigenic molecules including IL-6, IL-8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (*Nat. Biotechnol.* 14:845-851, 1996), which contains gene sequences from unrearranged human antibody genes that code for the heavy and light chains of human antibodies. Immunization of a HuMAb-MOUSE® enables the production of fully human monoclonal antibodies to the target protein.

Also, Ishida et al. (*Cloning Stem Cells.* 4:91-102, 2002) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TC MOUSE™ with various human antigens produces antibody responses comprising human antibodies.

See also Jakobovits et al., *Proc. Natl. Acad. Sci. USA,* 90:2551 (1993); Jakobovits et al., *Nature,* 362:255-258 (1993); Bruggermann et al., *Year in Immunol.,* 7:33 (1993); and U.S. Pat. Nos. 5,591,669, 5,589,369, 5,545,807; and U.S. Patent Publication No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human antibodies can also be generated through the in vitro screening of antibody display libraries. See Hoogenboom et al. (1991), J. Mol. Biol. 227: 381; and Marks et al. (1991), J. Mol. Biol. 222: 581. Various antibody-containing phage display libraries have been described and may be readily prepared. Libraries may contain a diversity of human antibody sequences, such as human Fab, Fv, and scFv fragments, that may be screened against an appropriate target. Phage display libraries may comprise peptides or proteins other than antibodies which may be screened to identify selective binding agents of IL-1β.

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments-usually Fv or Fab fragments-in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

The invention contemplates a method for producing target-specific antibody or antigen-binding portion thereof comprising the steps of synthesizing a library of human antibodies on phage, screening the library with target protein or a portion thereof, isolating phage that bind target, and obtaining the antibody from the phage. By way of example, one method for preparing the library of antibodies for use in phage display techniques comprises the steps of immunizing a non-human animal comprising human immunoglobulin loci with target antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant target-specific antibodies of the invention may be obtained in this way.

Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach. Antibodies of the invention can be isolated by screening of a recombinant combinatorial antibody library, preferably a scFv phage display library, prepared using human $V_L$ and $V_H$ cDNAs prepared from mRNA derived from human lymphocytes. Methodologies for preparing and screening such libraries are known in the art. See e.g., U.S. Pat. No. 5,969,108. There are commercially available kits for generating phage display libraries (e.g., the Pharmacia Recombinant Phage Antibody System, catalog no. 27-9400-01; and the Stratagene SURFZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum. Antibod. Hybridomas* 3:81-85; Huse et al. (1989) Science 246:1275-1281; McCafferty et al., Nature (1990) 348:552-554; Griffiths et al. (1993) *EMBO J.* 12:725-734; Hawkins et al. (1992) *J. Mol. Biol.* 226:889-896; Clackson et al. (1991) Nature 352:624-628; Gram et al. (1992) *Proc. Natl. Acad. Sci. USA* 89:3576-3580; Garrad et al. (1991) *Bio/Technology* 9:1373-1377; Hoogenboom et al. (1991) Nuc Acid Res 19:4133-4137; and Barbas et al. (1991) *Proc. Natl. Acad. Sci. USA* 88:7978-7982.

In one embodiment, to isolate human antibodies specific for the target antigen with the desired characteristics, a human $V_H$ and $V_L$ library are screened to select for antibody fragments having the desired specificity. The antibody libraries used in this method are preferably scFv libraries prepared and screened as described herein and in the art (McCafferty et al., PCT Publication No. WO 92/01047, McCafferty et al., (*Nature* 348:552-554, 1990); and Griffiths et al., (*EMBO J.* 12:725-734, 1993). The scFv antibody libraries preferably are screened using target protein as the antigen.

Alternatively, the Fd fragment ($V_H$-$C_H$1) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., *Bio/Technology* 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., *J. Mol. Biol.*, 227:381 (1991); Marks et al., *J. Mol. Biol*, 222:581-597 (1991); U.S. Pat. Nos. 5,565,332 and 5,573,905; Clackson, T., and Wells, J. A., *TIBTECH* 12, 173-184 (1994)). In particular, in vitro selection and evolution of antibodies derived from phage display libraries has become a powerful tool (See Burton, D. R., and Barbas III, C. F., *Adv. Immunol.* 57, 191-280 (1994); Winter, G., et al., *Annu. Rev. Immunol.* 12, 433-455 (1994); U.S. patent publication no. 20020004215 and WO 92/01047; U.S. patent publication no. 20030190317; and U.S. Pat. Nos. 6,054,287 and 5,877,293.

Watkins, "Screening of Phage-Expressed Antibody Libraries by Capture Lift," Methods in Molecular Biology, Antibody Phage Display: Methods and Protocols 178: 187-193 (2002), and U.S. patent publication no. 20030044772, published Mar. 6, 2003, describe methods for screening phage-expressed antibody libraries or other binding molecules by capture lift, a method involving immobilization of the candidate binding molecules on a solid support.

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, f1, If1, Ike, ZJ/Z, Ff and one of the class II phages Xf, Pf1 and Pf3. The phage may be M13, or fd or a derivative thereof.

Once initial human $V_L$ and $V_H$ segments are selected, "mix and match" experiments, in which different pairs of the initially selected $V_L$ and $V_H$ segments are screened for target binding, are performed to select preferred $V_L/V_H$ pair combinations. Additionally, to further improve the quality of the antibody, the $V_L$ and $V_H$ segments of the preferred $V_L/V_H$ pair(s) can be randomly mutated, preferably within the any of the CDR1, CDR2 or CDR3 region of $V_H$ and/or $V_L$, in a process analogous to the in vivo somatic mutation process responsible for affinity maturation of antibodies during a natural immune response. This in vitro affinity maturation can be accomplished by amplifying $V_L$ and $V_H$ regions using PCR primers complimentary to the $V_H$ CDR1, CDR2, and CDR3, or $V_L$ CDR1, CDR2, and CDR3, respectively, which primers have been "spiked" with a random mixture of the four nucleotide bases at certain positions such that the resultant PCR products encode $V_L$ and $V_H$ segments into which random mutations have been introduced into the $V_H$ and/or $V_L$ CDR3 regions. These randomly mutated $V_L$ and $V_H$ segments can be rescreened for binding to target antigen.

Following screening and isolation of an target specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be carried out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3; and phage displaying or encoding a binding molecule fused to a capsid protein.

Antibodies are also generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described therein. This technique is also disclosed in Marks et al, (Bio/Technology, 10:779-783, 1992).

Methods for display of peptides on the surface of yeast and microbial cells have also been used to identify antigen specific antibodies. See, for example, U.S. Pat. No. 6,699,658. Antibody libraries may be attached to yeast proteins, such as agglutinin, effectively mimicking the cell surface display of antibodies by B cells in the immune system.

In addition to phage display methods, antibodies may be isolated using ribosome mRNA display methods and microbial cell display methods. Selection of polypeptide using ribosome display is described in Hanes et al., (Proc. Natl. Acad Sci USA, 94:4937-4942, 1997) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

The IL-1 (e.g., IL-1β) binding antibodies and fragments may comprise one or more portions that do not bind IL-1β but instead are responsible for other functions, such as circulating half-life, direct cytotoxic effect, detectable labeling, or activation of the recipient's endogenous complement cascade or endogenous cellular cytotoxicity. The antibodies or fragments may comprise all or a portion of the constant region and may be of any isotype, including IgA (e.g., IgA1 or IgA2), IgD, IgE, IgG (e.g. IgG1, IgG2, IgG3 or IgG4), or IgM. In addition to, or instead of, comprising a constant region, antigen-binding compounds of the invention may include an epitope tag, a salvage receptor epitope, a label moiety for diagnostic or purification purposes, or a cytotoxic moiety such as a radionuclide or toxin.

The constant region (when present) of the present antibodies and fragments may be of the γ1, γ2, γ3, γ4, μ, β2, or δ or ε type, preferably of the γ type, more preferably of the y, type, whereas the constant part of a human light chain may be of the κ or λ type (which includes the $\lambda_1$, $\lambda_2$ and $\lambda_3$ subtypes) but is preferably of the κ type.

Variants also include antibodies or fragments comprising a modified Fc region, wherein the modified Fc region comprises at least one amino acid modification relative to a wild-type Fc region. The variant Fc region may be designed, relative to a comparable molecule comprising the wild-type Fc region, so as to bind Fc receptors with a greater or lesser affinity.

For example, the present IL-1β binding antibodies and fragments may comprise a modified Fc region. Fc region refers to naturally-occurring or synthetic polypeptides homologous to the IgG C-terminal domain that is produced upon papain digestion of IgG. IgG Fc has a molecular weight of approximately 50 kD. In the present antibodies and fragments, an entire Fc region can be used, or only a half-life enhancing portion. In addition, many modifications in amino acid sequence are acceptable, as native activity is not in all cases necessary or desired.

The Fc region can be mutated, if desired, to inhibit its ability to fix complement and bind the Fc receptor with high affinity. For murine IgG Fc, substitution of Ala residues for Glu 318, Lys 320, and Lys 322 renders the protein unable to direct ADCC. Substitution of Glu for Leu 235 inhibits the ability of the protein to bind the Fc receptor with high affinity. Various mutations for human IgG also are known (see, e.g., Morrison et al., 1994, The Immunologist 2: 119 124 and Brekke et al., 1994, The Immunologist 2: 125).

In some embodiments, the present an antibodies or fragments are provided with a modified Fc region where a naturally-occurring Fc region is modified to increase the half-life of the antibody or fragment in a biological environment, for example, the serum half-life or a half-life measured by an in vitro assay. Methods for altering the original form of a Fc region of an IgG also are described in U.S. Pat. No. 6,998,253.

In certain embodiments, it may be desirable to modify the antibody or fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, International Publication No. WO96/32478). Salvage receptor binding epitope refers to an epitope of the Fc region of an IgG molecule (e.g., $IgG_1$, $IgG_2$, $IgG_3$, or $IgG_4$) that is responsible for increasing the in vivo serum half-life of the IgG molecule.

A salvage receptor binding epitope can include a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment. See also International applications WO 97/34631 and WO 96/32478 which describe Fc variants and their interaction with the salvage receptor.

Mutation of residues within Fc receptor binding sites can result in altered effector function, such as altered ADCC or CDC activity, or altered half-life. Potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position). For example it has been reported that mutating the serine at amino acid position 241 in IgG4 to proline (found at that position in IgG1 and IgG2) led to the production of a homogeneous antibody, as well as extending serum half-life and improving tissue distribution compared to the original chimeric IgG4. (Angal et al., Mol. Immunol. 30:105-8, 1993).

Antibody fragments are portions of an intact full length antibody, such as an antigen binding or variable region of the intact antibody. Examples of antibody fragments include Fab, Fab', F(ab')$_2$, and Fv fragments; diabodies; linear antibodies; single-chain antibody molecules (e.g., scFv); multispecific antibody fragments such as bispecific, trispecific, and multispecific antibodies (e.g., diabodies, triabodies, tetrabodies); minibodies; chelating recombinant antibodies; tribodies or bibodies; intrabodies; nanobodies; small modular immunopharmaceuticals (SMIP), adnectins, binding-domain immunoglobulin fusion proteins; camelized antibodies; V$_{HH}$ containing antibodies; and any other polypeptides formed from antibody fragments.

The present invention includes IL-1β binding antibody fragments comprising any of the foregoing heavy or light chain sequences and which bind IL-1β. The term fragments as used herein refers to any 3 or more contiguous amino acids (e.g., 4 or more, 5 or more 6 or more, 8 or more, or even 10 or more contiguous amino acids) of the antibody and encompasses Fab, Fab', F(ab')$_2$, and F(v) fragments, or the individual light or heavy chain variable regions or portion thereof. IL-1β binding fragments include, for example, Fab, Fab', F(ab')$_2$, Fv and scFv. These fragments lack the Fc fragment of an intact antibody, clear more rapidly from the circulation, and can have less non-specific tissue binding than an intact antibody. See Wahl et al. (1983), J. Nucl. Med., 24: 316-25. These fragments can be produced from intact antibodies using well known methods, for example by proteolytic cleavage with enzymes such as papain (to produce Fab fragments) or pepsin (to produce F(ab')$_2$ fragments).

In vitro and cell based assays are well described in the art for use in determining binding of IL-1β to IL-1 receptor type I (IL-1R1), including assays that determining in the presence of molecules (such as antibodies, antagonists, or other inhibitors) that bind to IL-1β or IL-1RI. (see for example Evans et al., (1995), J. Biol. Chem. 270:11477-11483; Vigers et al., (2000), J. Biol. Chem. 275:36927-36933; Yanofsky et al., (1996), Proc. Natl. Acad. Sci. USA 93:7381-7386; Fredericks et al., (2004), Protein Eng. Des. Sel. 17:95-106; Slack et al., (1993), J. Biol. Chem. 268:2513-2524; Smith et al., (2003), Immunity 18:87-96; Vigers et al., (1997), Nature 386:190-194; Ruggiero et al., (1997), J. Immunol. 158:3881-3887; Guo et al., (1995), J. Biol. Chem. 270:27562-27568; Svenson et al., (1995), Eur. J. Immunol. 25:2842-2850; Arend et al., (1994), J. Immunol. 153:4766-4774). Recombinant IL-1 receptor type I, including human IL-1 receptor type I, for such assays is readily available from a variety of commercial sources (see for example R&D Systems, SIGMA). IL-1 receptor type I also can be expressed from an expression construct or vector introduced into an appropriate host cell using standard molecular biology and transfection techniques known in the art. The expressed IL-1 receptor type I may then be isolated and purified for use in binding assays, or alternatively used directly in a cell associated form.

For example, the binding of IL-1β to IL-1 receptor type I may be determined by immobilizing an IL-1β binding antibody, contacting IL-1β with the immobilized antibody and determining whether the IL-1β was bound to the antibody, and contacting a soluble form of IL-1RI with the bound IL-1β/antibody complex and determining whether the soluble IL-1RI was bound to the complex. The protocol may also include contacting the soluble IL-1RI with the immobilized antibody before the contact with IL-1β, to confirm that the soluble IL-1 RI does not bind to the immobilized antibody. This protocol can be performed using a BIACORE® instrument for kinetic analysis of binding interactions. Such a protocol can also be employed to determine whether an antibody or other molecule permits or blocks the binding of IL-1β to IL-1 receptor type I.

For other IL-1β/IL-1RI binding assays, the permitting or blocking of IL-1β binding to IL-1 receptor type I may be determined by comparing the binding of IL-1β to IL-1RI in the presence or absence of IL-1β antibodies or IL-1β binding fragments thereof. Blocking is identified in the assay readout as a designated reduction of IL-1β binding to IL-1 receptor type I in the presence of anti-IL-1β antibodies or IL-1β binding fragments thereof, as compared to a control sample that contains the corresponding buffer or diluent but not an IL-1β antibody or IL-1β binding fragment thereof. The assay readout may be qualitatively viewed as indicating the presence or absence of blocking, or may be quantitatively viewed as indicating a percent or fold reduction in binding due to the presence of the antibody or fragment.

Alternatively or additionally, when an IL-1β binding antibody or IL-1β binding fragment substantially blocks IL-1β binding to IL-1RI, the IL-1β binding to IL-1RI is reduced by at least 10-fold, alternatively at least about 20-fold, alternatively at least about 50-fold, alternatively at least about 100-fold, alternatively at least about 1000-fold, alternatively at least about 10000-fold, or more, compared to binding of the same concentrations of IL-1β and IL-1RI in the absence of the antibody or fragment. As another example, when an IL-1β binding antibody or IL-1β binding fragment substantially permits IL-1β binding to IL-1RI, the IL-1β binding to IL-1RI is at least about 90%, alternatively at least about 95%, alternatively at least about 99%, alternatively at least about 99.9%, alternatively at least about 99.99%, alternatively at least about 99.999%, alternatively at least about 99.9999%, alternatively substantially identical to binding of the same concentrations of IL-1β and IL-1RI in the absence of the antibody or fragment.

The present invention may in certain embodiments encompass IL-1β binding antibodies or IL-1β binding fragments that bind to the same epitope or substantially the same epitope as one or more of the exemplary antibodies described herein. Alternatively or additionally, the IL-1β binding antibodies or IL-1β binding fragments compete with the binding of an antibody having variable region sequences of AB7, described in U.S. application Ser. No. 11/472,813 or WO 2007/002261 (sequences shown below). As an example, when an IL-1β binding antibody or IL-1β binding fragment competes with the binding of an antibody having the light chain variable region of SEQ ID NO:5 and the heavy chain variable region of SEQ ID NO:6, binding of an antibody having the light chain variable region of SEQ ID NO:5 and the heavy chain variable region of SEQ ID NO:6 to IL-1β may be reduced by at least about 2-fold, alternatively at least about 5-fold, alternatively at least about 10-fold, alternatively at least about 20-fold, alternatively at least about 50-fold, alternatively at least about 100-fold, alternatively at least about 1000-fold, alternatively at least about 10000-fold, or more, if the binding is measured in the presence of the IL-1β binding antibody or IL-1β binding fragment. The IL-1β binding antibody or IL-1β binding fragment may be present in excess of the antibody having the light chain variable region of SEQ ID NO:5 and the heavy chain variable region of SEQ ID NO:6, for example an excess of least about 2-fold, alternatively at least about 5-fold, alternatively at least about 10-fold, alternatively at least about 20-fold, alternatively at least about 50-fold, alternatively at least about 100-fold, alternatively at least about 1000-fold, alternatively at least about 10000-fold. Alternatively or additionally, the present invention encompasses IL-1β binding antibodies and fragments that bind to an epitope contained in the amino acid sequence ESVDPKNYPKKK-MEKRFVFNKIE (SEQ ID NO: 1), an epitope that the antibodies designated AB5 and AB7 (U.S. application Ser. No. 11/472,813, WO 2007/002261) bind to. As contemplated herein, one can readily determine if an IL-1β binding antibody or fragment binds to the same epitope or substantially the same epitope as one or more of the exemplary antibodies, such as for example the antibody designated AB7, using any of several known methods in the art.

For example, the key amino acid residues (epitope) bound by an IL-1β binding antibody or fragment may be determined using a peptide array, such as for example, a PEPSPOT™ peptide array (JPT Peptide Technologies, Berlin, Germany), wherein a scan of twelve amino-acid peptides, spanning the entire IL-1β amino acid sequence, each peptide overlapping by 11 amino acid to the previous one, is synthesized directly on a membrane. The membrane carrying the peptides is then probed with the antibody for which epitope binding information is sought, for example at a concentration of 2 μg/ml, for 2 hr at room temperature. Binding of antibody to membrane bound peptides may be detected using a secondary HRP-conjugated goat anti-human (or mouse, when appropriate) antibody, followed by enhanced chemiluminescence (ECL). The peptides spot(s) corresponding to particular amino acid residues or sequences of the mature IL-1β protein, and which score positive for antibody binding, are indicative of the epitope bound by the particular antibody.

Alternatively or in addition, antibody competition experiments may be performed and such assays are well known in the art. For example, to determine if an antibody or fragment binds to an epitope contained in a peptide sequence comprising the amino acids ESVDPKNYPKKKMEKRFVFNKIE (SEQ ID NO: 1), which corresponds to residues 83-105 of the mature IL-1β protein, an antibody of unknown specificity may be compared with any of the exemplary of antibodies (e.g., AB7) of the present invention that are known to bind an epitope contained within this sequence. Binding competition assays may be performed, for example, using a BIACORE® instrument for kinetic analysis of binding interactions or by ELISA. In such an assay, the antibody of unknown epitope specificity is evaluated for its ability to compete for binding against the known comparator antibody (e.g., AB7). Competition for binding to a particular epitope is determined by a reduction in binding to the IL-1β epitope of at least about 50%, or at least about 70%, or at least about 80%, or at least about 90%, or at least about 95%, or at least about 99% or about 100% for the known comparator antibody (e.g., AB7) and is indicative of binding to substantially the same epitope.

In view of the identification in this disclosure of IL-1β binding regions in exemplary antibodies and/or epitopes recognized by the disclosed antibodies, it is contemplated that additional antibodies with similar binding characteristics and therapeutic or diagnostic utility can be generated that parallel the embodiments of this disclosure.

Antigen-binding fragments of an antibody include fragments that retain the ability to specifically bind to an antigen, generally by retaining the antigen-binding portion of the antibody. It is well established that the antigen-binding function of an antibody can be performed by fragments of a full-length antibody. Examples of antigen-binding portions include (i) a Fab fragment, which is a monovalent fragment consisting of the VL, VH, CL and CH1 domains; (ii) a F(ab')$^2$ fragment, which is a bivalent fragment comprising two Fab fragments linked by a disulfide bridge at the hinge region; (iii) a Fd fragment which is the VH and CH1 domains; (iv) a Fv fragment which is the VL and VH domains of a single arm of an antibody, (v) a dAb fragment (Ward et al., (1989) Nature 341:544-546), which is a $V_H$ domain; and (vi) an isolated complementarity determining region (CDR). Single chain antibodies are also encompassed within the term antigen-binding portion of an antibody. The IL-1β binding antibodies and fragments of the present invention also encompass monovalent or multivalent, or monomeric or multimeric (e.g. tetrameric), CDR-derived binding domains with or without a scaffold (for example, protein or carbohydrate scaffolding).

The present IL-1β binding antibodies or fragments may be part of a larger immunoadhesion molecules, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibodies and fragments comprising immunoadhesion molecules can be obtained using standard recombinant DNA techniques, as described herein. Preferred antigen binding portions are complete domains or pairs of complete domains.

The IL-1β binding antibodies and fragments of the present invention also encompass domain antibody (dAb) fragments (Ward et al., Nature 341:544-546, 1989) which consist of a $V_H$ domain. The IL-1β binding antibodies and fragments of the present invention also encompass diabodies, which are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., Proc. Natl. Acad. Sci. USA 90:6444-6448, 1993, and Poljak et al., Structure 2:1121-1123, 1994). Diabodies can be bispecific or monospecific.

The IL-1β binding antibodies and fragments of the present invention also encompass single-chain antibody fragments (scFv) that bind to IL-1β. An scFv comprises an antibody heavy chain variable region ($V_H$) operably linked to an antibody light chain variable region ($V_L$) wherein the heavy chain variable region and the light chain variable region, together or individually, form a binding site that binds IL-1β. An scFv may comprise a $V_H$ region at the amino-terminal end and a $V_L$ region at the carboxy-terminal end. Alternatively, scFv may comprise a $V_L$ region at the amino-terminal end and a $V_H$ region at the carboxy-terminal end. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883).

An scFv may optionally further comprise a polypeptide linker between the heavy chain variable region and the light chain variable region. Such polypeptide linkers generally comprise between 1 and 50 amino acids, alternatively between 3 and 12 amino acids, alternatively 2 amino acids. An example of a linker peptide for linking heavy and light chains in an scFv comprises the 5 amino acid sequence Gly-Gly-Gly-Gly-Ser (SEQ ID NO: 2). Other examples comprise one or more tandem repeats of this sequence (for example, a polypeptide comprising two to four repeats of Gly-Gly-Gly-Gly-Ser (SEQ ID NO: 2) to create linkers.

The IL-1β binding antibodies and fragments of the present invention also encompass heavy chain antibodies (HCAb). Exceptions to the $H_2L_2$ structure of conventional antibodies occur in some isotypes of the immunoglobulins found in camelids (camels, dromedaries and llamas; Hamers-Casterman et al., 1993 Nature 363: 446; Nguyen et al., 1998 *J. Mol. Biol.* 275: 413), wobbegong sharks (Nuttall et al., *Mol. Immunol.* 38:313-26, 2001), nurse sharks (Greenberg et al., *Nature* 374:168-73, 1995; Roux et al., 1998 Proc. Nat. Acad. Sci. USA 95: 11804), and in the spotted ratfish (Nguyen, et al., "Heavy-chain antibodies in Camelidae; a case of evolutionary innovation," 2002 Immunogenetics 54(1): 39-47). These antibodies can apparently form antigen-binding regions using only heavy chain variable regions, in that these functional antibodies are dimers of heavy chains only (referred to as "heavy-chain antibodies" or "HCAbs"). Accordingly, some embodiments of the present IL-1β binding antibodies and fragments may be heavy chain antibodies that specifically bind to IL-1β. For example, heavy chain antibodies that are a class of IgG and devoid of light chains are produced by animals of the genus Camelidae which includes camels, dromedaries and llamas (Hamers-Casterman et al., Nature 363:446-448 (1993)). HCAbs have a molecular weight of about 95 kDa instead of the about 160 kDa molecular weight of conventional IgG antibodies. Their binding domains consist only of the heavy-chain variable domains, often referred to as $V_{HH}$ to distinguish them from conventional $V_H$. Muyldermans et al., J. Mol. Recognit. 12:131-140 (1999). The variable domain of the heavy-chain antibodies is sometimes referred to as a nanobody (Cortez-Retamozo et al., *Cancer Research* 64:2853-57, 2004). A nanobody library may be generated from an immunized dromedary as described in Conrath et al., (*Antimicrob Agents Chemother* 45: 2807-12, 2001) or using recombinant methods.

Since the first constant domain ($C_{H1}$) is absent (spliced out during mRNA processing due to loss of a splice consensus signal), the variable domain ($V_{HH}$) is immediately followed by the hinge region, the $C_{H2}$ and the $C_{H3}$ domains (Nguyen et al., Mol. Immunol. 36:515-524 (1999); Woolven et al., Immunogenetics 50:98-101 (1999)). Camelid $V_{HH}$ reportedly recombines with IgG2 and IgG3 constant regions that contain hinge, $CH_2$, and CH3 domains and lack a CH1 domain (Hamers-Casterman et al., supra). For example, llama IgG1 is a conventional ($H_2L_2$) antibody isotype in which $V_H$ recombines with a constant region that contains hinge, CH1, CH2 and CH3 domains, whereas the llama IgG2 and IgG3 are heavy chain-only isotypes that lack CH1 domains and that contain no light chains.

Although the HCAbs are devoid of light chains, they have an antigen-binding repertoire. The genetic generation mechanism of HCAbs is reviewed in Nguyen et al. Adv. Immunol 79:261-296 (2001) and Nguyen et al., Immunogenetics 54:39-47 (2002).

Sharks, including the nurse shark, display similar antigen receptor-containing single monomeric V-domains. Irving et al., J. Immunol. Methods 248:31-45 (2001); Roux et al., Proc. Natl. Acad. Sci. USA 95:11804 (1998).

$V_{HH}$s comprise small intact antigen-binding fragments (for example, fragments that are about 15 kDa, 118-136 residues). Camelid $V_{HH}$ domains have been found to bind to antigen with high affinity (Desmyter et al., *J. Biol. Chem.* 276:26285-90, 2001), with $V_{HH}$ affinities typically in the nanomolar range and comparable with those of Fab and scFv fragments. $V_{HH}$s are highly soluble and more stable than the corresponding derivatives of scFv and Fab fragments. $V_H$ fragments have been relatively difficult to produce in soluble form, but improvements in solubility and specific binding can be obtained when framework residues are altered to be more $V_{HH}$-like. (See, for example, Reichman et al., J Immunol Methods 1999, 231:25-38.) $V_{HH}$s carry amino acid substitutions that make them more hydrophilic and prevent prolonged interaction with BiP (immunoglobulin heavy-chain binding protein), which normally binds to the H-chain in the Endoplasmic Reticulum (ER) during folding and assembly, until it is displaced by the L-chain. Because of the $V_{HH}$s' increased hydrophilicity, secretion from the ER is improved.

Functional $V_{HH}$s may be obtained by proteolytic cleavage of HCAb of an immunized camelid, by direct cloning of $V_{HH}$ genes from B-cells of an immunized camelid resulting in recombinant $V_{HH}$s, or from naive or synthetic libraries. $V_{HH}$s with desired antigen specificity may also be obtained through phage display methodology. Using $V_{HH}$s in phage display is much simpler and more efficient compared to Fabs or scFvs, since only one domain needs to be cloned and expressed to obtain a functional antigen-binding fragment. Muyldermans, Biotechnol. 74:277-302 (2001); Ghahroudi et al., FEBS Lett. 414:521-526 (1997); and van der Linden et al., J. Biotechnol. 80:261-270 (2000). Methods for generating antibodies having camelid heavy chains are also described in U.S. Patent Publication Nos. 20050136049 and 20050037421.

Ribosome display methods may be used to identify and isolate scFv and/or $V_{HH}$ molecules having the desired binding activity and affinity. Irving et al., J. Immunol. Methods 248: 31-45 (2001). Ribosome display and selection has the potential to generate and display large libraries ($10^{14}$).

Other embodiments provide $V_{HH}$-like molecules generated through the process of camelisation, by modifying non-Camelidae $V_H$S, such as human $V_{HH}$s, to improve their solubility and prevent non-specific binding. This is achieved by replacing residues on the $V_L$S side of $V_H$S with $V_{HH}$-like residues, thereby mimicking the more soluble $V_{HH}$ fragments. Camelised $V_H$ fragments, particularly those based on the human framework, are expected to exhibit a greatly reduced immune response when administered in vivo to a patient and, accordingly, are expected to have significant advantages for therapeutic applications. Davies et al., FEBS Lett. 339:285-290 (1994); Davies et al., Protein Eng. 9:531-537 (1996); Tanha et al., J. Biol. Chem. 276:24774-24780 (2001); and Riechmann et al., Immunol. Methods 231:25-38 (1999).

A wide variety of expression systems are available for the production of IL-1β fragments including Fab fragments, scFv, and $V_{HH}$s. For example, expression systems of both prokaryotic and eukaryotic origin may be used for the large-scale production of antibody fragments and antibody fusion proteins. Particularly advantageous are expression systems that permit the secretion of large amounts of antibody fragments into the culture medium.

Production of bispecific Fab-scFv ("bibody") and trispecific Fab-(scFv)(2) ("tribody") are described in Schoonjans et al. (*J Immunol.* 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-$CH_1$ (Fd) chains, e.g., to produce a tribody two scFvs are fused to C-term of Fab while in a bibody one scFv is fused to C-term of Fab. A "minibody" consisting of scFv fused to $CH_3$ via a peptide linker (hingeless) or via an IgG hinge has been described in Olafsen, et al., Protein Eng Des Sel. 2004 April; 17(4):315-23.

Intrabodies are single chain antibodies which demonstrate intracellular expression and can manipulate intracellular protein function (Biocca, et al., *EMBO J.* 9:101-108, 1990; Colby et al., *Proc Natl Acad Sci USA.* 101: 17616-21, 2004).

Intrabodies, which comprise cell signal sequences which retain the antibody construct in intracellular regions, may be produced as described in Mhashilkar et al (*EMBO J.* 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med. Hypotheses.* 64:1105-8, 2005).

The IL-1β binding antibodies and fragments of the present invention also encompass antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

The IL-1β binding antibodies and fragments of the present invention also encompass immunoadhesins. One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs disclosed herein permit the immunoadhesin to specifically bind to IL-1β.

The IL-1β binding antibodies and fragments of the present invention also encompass antibody mimics comprising one or more IL-1β binding portions built on an organic or molecular scaffold (such as a protein or carbohydrate scaffold). Proteins having relatively defined three-dimensional structures, commonly referred to as protein scaffolds, may be used as reagents for the design of antibody mimics. These scaffolds typically contain one or more regions which are amenable to specific or random sequence variation, and such sequence randomization is often carried out to produce libraries of proteins from which desired products may be selected. For example, an antibody mimic can comprise a chimeric non-immunoglobulin binding polypeptide having an immunoglobulin-like domain containing scaffold having two or more solvent exposed loops containing a different CDR from a parent antibody inserted into each of the loops and exhibiting selective binding activity toward a ligand bound by the parent antibody. Non-immunoglobulin protein scaffolds have been proposed for obtaining proteins with novel binding properties. (Tramontano et al., J. Mol. Recognit. 7:9, 1994; McConnell and Hoess, J. Mol. Biol. 250:460, 1995). Other proteins have been tested as frameworks and have been used to display randomized residues on alpha helical surfaces (Nord et al., Nat. Biotechnol. 15:772, 1997; Nord et al., Protein Eng. 8:601, 1995), loops between alpha helices in alpha helix bundles (Ku and Schultz, Proc. Natl. Acad. Sci. USA 92:6552, 1995), and loops constrained by disulfide bridges, such as those of the small protease inhibitors (Markland et al., Biochemistry 35:8045, 1996; Markland et al., Biochemistry 35:8058, 1996; Rottgen and Collins, Gene 164:243, 1995; Wang et al., J. Biol. Chem. 270:12250, 1995). Methods for employing scaffolds for antibody mimics are disclosed in U.S. Pat. No. 5,770,380 and US Patent Publications 2004/0171116, 2004/0266993, and 2005/0038229.

Preferred IL-1β antibodies or antibody fragments for use in accordance with the invention generally bind to human IL-1β with high affinity (e.g., as determined with BIACORE®), such as for example with an equilibrium binding dissociation constant ($K_D$) for IL-1β of about 10 nM or less, about 5 nM or less, about 1 nM or less, about 500 pM or less, or more preferably about 250 pM or less, about 100 pM or less, about 50 pM or less, about 25 pM or less, about 10 pM or less, about 5 pM or less, about 3 pM or less about 1 pM or less, about 0.75 pM or less, about 0.5 pM or less, or about 0.3 pM or less. The dissociation constant may be measured using BIACORE® (GE Healthcare), and measurement using BIACORE® may be preferred when the dissociation constant is greater than about 10 pM. Alternatively or in addition, the dissociation constant may be measured using KinExA (Sapidyne Instruments, Inc), and measurement using KinExA may be preferred when the dissociation constant is less than about 10 pM.

Antibodies or fragments of the present invention may, for example, bind to IL-1β with an $IC_{50}$ of about 10 nM or less, about 5 nM or less, about 2 nM or less, about 1 nM or less, about 0.75 nM or less, about 0.5 nM or less, about 0.4 nM or less, about 0.3 nM or less, or even about 0.2 nM or less, as determined by enzyme linked immunosorbent assay (ELISA). Preferably, the antibody or antibody fragment of the present invention does not cross-react with any target other than IL-1. For example, the present antibodies and fragments may bind to IL-1β, but do not detectably bind to IL-1α, or have at least about 100 times (e.g., at least about 150 times, at least about 200 times, or even at least about 250 times) greater selectivity in its binding of IL-1β relative to its binding of IL-1α. Antibodies or fragments used according to the invention may, in certain embodiments, inhibit IL-1β induced expression of serum IL-6 in an animal by at least 50% (e.g., at least 60%, at least 70%, or even at least 80%) as compared to the level of serum IL-6 in an IL-1β stimulated animal that has not been administered an antibody or fragment of the invention. Antibodies may bind IL-1β but permit or substantially permit the binding of the bound IL-1β ligand to IL-1 receptor type I (IL-1RI). In contrast to many known IL-1β binding antibodies that block or substantially interfere with binding of IL-1β to IL-1RI, the antibodies designated AB5 and AB7 (U.S. application Ser. No. 11/472,813, WO 2007/002261) selectively bind to the IL-1β ligand, but permit the binding of the bound IL-1β ligand to IL-1RI. For example, the antibody designated AB7 binds to an IL-1β epitope but still permits the bound IL-1β to bind to IL-1RI. In certain embodiments, the antibody may decrease the affinity of interaction of bound IL-1β to bind to IL-1RI. Accordingly, the invention provides, in a related aspect, use of an IL-1β binding antibody or IL-1β binding antibody fragment that has at least one of the aforementioned characteristics. Any of the foregoing antibodies, antibody fragments, or polypeptides of the invention can be humanized or human engineered, as described herein.

A variety of IL-1 (e.g., IL-1β) antibodies and fragments known in the art may be used according the methods provided herein, including for example antibodies described in or derived using methods described in the following patents and patent applications: U.S. Pat. No. 4,935,343; US 2003/0026806; US 2003/0124617 (e.g., antibody AAL160); WO 2006/081139 (e.g., antibody 9.5.2); WO 03/034984; WO 95/01997 (e.g., antibody SK48-E26 VTKY); WO 02/16436 (e.g., antibody ACZ 885); WO 03/010282 (e.g., antibody Hu007); WO 03/073982 (e.g., antibody N55S), WO 2004/072116, WO 2004/067568, EP 0 267 611 B1, EP 0 364 778 B1, and U.S. application Ser. No. 11/472,813. As a non-limiting example, antibodies AB5 and AB7 (U.S. application Ser. No. 11/472,813, WO2007/002261) may be used in accordance with the invention. Variable region sequences of AB5 and AB7 (also referred to as XOMA 052) are as follows:

AB5
Light Chain (SEQ ID NO: 3)
DIQMTQTTSSLSASLGDRVTISC<u>RASQDISNYLS</u>WYQQKPDGTVKLLIY <u>YTSKLHS</u>GVPSRFSGSGSGTDYSLTISNLEQEDIATYFC<u>LQGKMLPWT</u>

FGGGTKLEIK

The underlined sequences depict (from left to right) CDR1, 2 and 3.

Heavy Chain (SEQ ID NO: 4)
QVTLKESGPGILKPSQTLSLTCSFSGFSLS<u>TSGMGVG</u>WIRQPSGKGLEWL <u>AHIWWDGDESYNPSLK</u>TQLTISKDTSRNQVFLKITSVDTVDTATYFCAR <u>NRYDPPWFVDW</u>GQGTLVTVSS The underlined sequences depict (from left to right) CDR1, 2 and 3.

AB7
Light Chain (SEQ ID NO: 5)
DIQMTQSTSSLSASVGDRVTITC<u>RASQDISNYLS</u>WYQQKPGKAVKLLIY <u>YTSKLHS</u>GVPSRFSGSGSGTDYTLTISSLQQEDFATYFC<u>LQGKMLPWT</u>

FGQGTKLEIK

The underlined sequences depict (from left to right) CDR1, 2 and 3.

Heavy Chain (SEQ ID NO: 6)
QVQLQESGPGLVKPSQTLSLTCSFSGFSLS<u>TSGMGVG</u>WIRQPSGKGLEWL <u>AHIWWDGDESYNPSLK</u>SRLTISKDTSKNQVSLKITSVTAADTAVYFCAR <u>NRYDPPWFVDW</u>GQGTLVTVSS The underlined sequences depict (from left to right) CDR1, 2 and 3.

The antibodies and antibody fragments described herein can be prepared by any suitable method. Suitable methods for preparing such antibodies and antibody fragments are known in the art. Other methods for preparing the antibodies and antibody fragments are as described herein as part of the invention. The antibody, antibody fragment, or polypeptide of the invention, as described herein, can be isolated or purified to any degree. As used herein, an isolated compound is a compound that has been removed from its natural environment. A purified compound is a compound that has been increased in purity, such that the compound exists in a form that is more pure than it exists (i) in its natural environment or (ii) when initially synthesized and/or amplified under laboratory conditions, wherein "purity" is a relative term and does not necessarily mean "absolute purity."

Pharmaceutical Compositions

IL-1 (e.g., IL-1β) binding antibodies and antibody fragments for use according to the present invention can be formulated in compositions, especially pharmaceutical compositions, for use in the methods herein. Such compositions comprise a therapeutically or prophylactically effective amount of an IL-1β binding antibody or antibody fragment of the invention in admixture with a suitable carrier, e.g., a pharmaceutically acceptable agent. Typically, IL-1β binding antibodies and antibody fragments of the invention are sufficiently purified for administration to an animal before formulation in a pharmaceutical composition.

Pharmaceutically acceptable agents include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with albumin are exemplary appropriate carriers. The pharmaceutical compositions can include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also can be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers can be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in *Remington's Pharmaceutical Sciences*, 18th Edition, A. R. Gennaro, ed., Mack Publishing Company, 1990.

The composition can be in liquid form or in a lyophilized or freeze-dried form and may include one or more lyoprotectants, excipients, surfactants, high molecular weight structural additives and/or bulking agents (see for example U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g. polysorbate 20, polysorbate 80); poloxamers (e.g. poloxamer 188); poly(ethylene glycol) phenyl ethers (e.g. Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearylsarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl ofeyl-taurate; and the MONAQUAT™. series (Mona Industries, Inc., Paterson, N.J.), polyethyl glycol, polypropyl glycol, and copolymers of ethylene and propylene glycol (e.g. Pluronics, PF68 etc). Exemplary amounts of surfactant that may be present in the pre-lyophilized formulation are from about 0.001-0.5%. High molecular weight structural additives (e.g. fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions can be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, intralesional, intrarectal, transdermal, oral, and inhaled routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980, which is incorporated herein by reference.

Pharmaceutical compositions described herein can be formulated for controlled or sustained delivery in a manner that provides local concentration of the product (e.g., bolus, depot effect) sustained release and/or increased stability or half-life in a particular local environment. The invention contemplates that in certain embodiments such compositions may include a significantly larger amount of antibody or fragment in the initial deposit, while the effective amount of antibody or fragment actually released and available at any point in time for is in accordance with the disclosure herein an amount much lower than the initial deposit. The compositions can include the formulation of IL-1β binding antibodies, antibody fragments, nucleic acids, or vectors of the invention with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies). See, for example, the description of controlled release porous polymeric microparticles for the delivery of pharmaceutical compositions in PCT Application Publication WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(−)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals.

Microencapsulation of recombinant proteins for sustained release has been performed successfully with human growth hormone (rhGH), interferon-(rhIFN—), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present invention. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humour of the eye. Esterified derivatives of hyaluronic acid have been used to produce microspheres for use in delivery that are biocompatible and biodegradable (see for example, Cortivo et al., Biomaterials (1991) 12:727-730; European Publication No. 517,565; International Publication No. WO 96/29998; illum et al., J. Controlled Rel. (1994) 29:133-141). Exemplary hyaluronic acid containing compositions of the present invention comprise a hyaluronic acid ester polymer in an amount of approximately 0.1% to about 40% (w/w) of an IL-1β binding antibody or fragment to hyaluronic acid polymer.

Both biodegradable and non-biodegradable polymeric matrices can be used to deliver compositions in accordance with the invention, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which can be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see for example WO 04/009664, WO 05/087201, Sawhney, et al., Macromolecules, 1993, 26, 581-587,) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324).

A pharmaceutical composition comprising an IL-1β binding antibody or fragment can be formulated for inhalation, such as for example, as a dry powder. Inhalation solutions also can be formulated in a liquefied propellant for aerosol delivery. In yet another formulation, solutions may be nebulized. Additional pharmaceutical composition for pulmonary administration include, those described, for example, in PCT Application Publication WO 94/20069, which discloses pulmonary delivery of chemically modified proteins. For pulmonary delivery, the particle size should be suitable for delivery to the distal lung. For example, the particle size can be from 1 µm to 5 µm; however, larger particles may be used, for example, if each particle is fairly porous.

Certain formulations containing IL-1β binding antibodies or antibody fragments can be administered orally. Formulations administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of a selective binding agent. Diluents, flavorings, low melting point waxes, vegetable oils, lubricants, suspending agents, tablet disintegrating agents, and binders also can be employed.

Another preparation can involve an effective quantity of an IL-1β binding antibody or fragment in a mixture with non-toxic excipients which are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations can be determined in view of the present disclosure and general knowledge of formulation technology, depending upon the intended route of administration, delivery format, and desired dosage. Regardless of the manner of administration, an effective dose can be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages can be ascertained through use of appropriate dose-response data.

Additional formulations will be evident in light of the present disclosure, including formulations involving IL-1β binding antibodies and fragments in combination with one or more other therapeutic agents. For example, in some formulations, an IL-1β binding antibody, antibody fragment, nucleic acid, or vector of the invention is formulated with a second inhibitor of an IL-1 signaling pathway Representative second inhibitors include, but are not limited to, antibodies, antibody fragments, peptides, polypeptides, compounds, nucleic acids, vectors and pharmaceutical compositions, such as, for example, those described in U.S. Pat. No. 6,899,878, US 2003022869, US 20060094663, US 20050186615, US 20030166069, WO/04022718, WO/05084696, WO/05019259. For example, a composition may comprise an IL-1β binding antibody, antibody fragment, nucleic acid, or vector of the invention in combination with another IL-1β binding antibody, fragment, or a nucleic acid or vector encoding such an antibody or fragment.

The pharmaceutical compositions can comprise IL-1β binding antibodies or fragments in combination with other active agents. Such combinations are those useful for their intended purpose. The combinations which are part of this invention can be IL-1β antibodies and fragments, such as for example those described herein, and at least one additional agent. Examples of active agents that may be used in combination set forth below are illustrative for purposes and not intended to be limited. The combination can also include more than one additional agent, e.g., two or three additional agents if the combination is such that the formed composition can perform its intended function.

The invention further contemplates that pharmaceutical compositions comprising one or more other active agents may be administered separately from the IL-1β binding antibodies or fragments, and such separate administrations may be performed at the same point or different points in time, such as for example the same or different days. Administration of the other active agents may be according to standard medical practices known in the art, or the administration may be modified (e.g., longer intervals, smaller dosages, delayed initiation) when used in conjunction with administration of IL-1β binding antibodies or fragments, such as disclosed herein.

Active agents or combinations with the present antibodies or fragments include indomethacin, non-steroidal anti-inflammatory drugs (NSAIDs) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors, aquaretics, oral glucocorticoids, intra-articular glucocorticoids, colchicine, xanthine-oxidase inhibitors, allopurinol, uricosuric agents, sulfinpyrazone, febuxostat, probenecid, fenofibrate, benemid, angiotensin II receptor antagonists, losartan, thiazides, PEG-uricase, sodium bicarbonate, ethylenediaminetetraacetic acid. Other active agents for combination include steroids such as prednisolone, prednisone, methylprednisolone, betamethasone, dexamethasone, or hydrocortisone. Such a combination may be especially advantageous, since one or more side-effects of the steroid can be reduced or even eliminated by tapering the steroid dose required when treating patients in combination with the present antibodies and fragments.

It is further contemplated that an anti-IL-1β antibody or fragment administered to a subject in accordance with the invention may be administered in combination with treatment with at least one additional active agent, such as for example any of the aforementioned active agents. In one embodiment, treatment with the at least one active agent is maintained. In another embodiment, treatment with the at least one active agent is reduced or discontinued (e.g., when the subject is stable) during the course of IL-1β antibody treatment (e.g., with the anti-IL-1β antibody or fragment maintained at a constant dosing regimen. In another embodiment, treatment with the at least one active agent is reduced or discontinued (e.g., when the subject is stable), and treatment with the anti-IL-1β antibody or fragment is reduced (e.g., lower dose, less frequent dosing, shorter treatment regimen). In another embodiment, treatment with the at least one active agent is reduced or discontinued (e.g., when the subject is stable), and treatment with the anti-IL-1β antibody or fragment is increased (e.g., higher dose, more frequent dosing, longer treatment regimen). In yet another embodiment, treatment with the at least one active agent is maintained and treatment with the anti-IL-1β antibody or fragment is reduced or discontinued (e.g., lower dose, less frequent dosing, shorter treatment regimen). In yet another embodiment, treatment with the at least one active agent and treatment with the anti-IL-1β antibody or fragment are reduced or discontinued (e.g., lower dose, less frequent dosing, shorter treatment regimen)

The pharmaceutical compositions used in the invention may include a therapeutically effective amount or a prophylactically effective amount of the IL-1β binding antibodies or fragments. A therapeutically effective amount refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A prophylactically effective amount refers to an amount effective, at dosages and for periods of time necessary, to achieve the desired prophylactic result.

A therapeutically or prophylactically effective amount of a pharmaceutical composition comprising an IL-1β binding antibody or fragment will depend, for example, upon the therapeutic objectives such as the indication for which the composition is being used, the route of administration, and the condition of the subject. Pharmaceutical compositions are administered in a therapeutically or prophylactically effective amount to treat an IL-1 related condition.

Methods of Use

Anti-IL-1β antibodies as provided herein may be used for the treatment and/or prevention of gout in a subject. Such methods may be used to treat a mammalian subject (e.g., human) suffering from gout or to prevent occurrence of the same in an at risk subject.

The terms "prevention", "prevent", "preventing", "suppression", "suppress", "suppressing", "inhibit" and "inhibition" as used herein refer to a course of action (such as administering a compound or pharmaceutical composition) initiated in a manner (e.g., prior to the onset of a clinical symptom of a disease state or condition) so as to prevent, suppress or reduce, either temporarily or permanently, the onset of a clinical manifestation of the disease state or condition. Such preventing, suppressing or reducing need not be absolute to be useful.

The terms "treatment", "treat" and "treating" as used herein refers a course of action (such as administering a compound or pharmaceutical composition) initiated after the onset of a clinical symptom of a disease state or condition so as to eliminate, reduce, suppress or ameliorate, either temporarily or permanently, a clinical manifestation or progression of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a condition that is treatable by a method or compound of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method or compound of the disclosure.

The term "therapeutically effective amount" as used herein refers to an amount of a compound (e.g., antibody), either alone or as a part of a pharmaceutical composition, that is capable of having any detectable, positive effect on any symptom, aspect, or characteristics of a disease state or condition when administered to a patient (e.g., as one or more doses). Such effect need not be absolute to be beneficial.

In one embodiment, the anti-IL-1β antibody or fragment is administered to a subject with gout and the subject also receives at least one other medically accepted treatment (e.g, medication, drug, therapeutic, active agent) for the disease, condition or complication. In another embodiment, the at least one other medically accepted treatment for the disease, condition or complication is reduced or discontinued (e.g., when the subject is stable), while treatment with the anti-IL-1β antibody or fragment is maintained at a constant dosing regimen. In another embodiment, the at least one other medically accepted treatment for the disease, condition or complication is reduced or discontinued (e.g., when the subject is stable), and treatment with the anti-IL-1β antibody or fragment is reduced (e.g., lower dose, less frequent dosing, shorter treatment regimen). In another embodiment, the at least one other medically accepted treatment for the disease, condition or complication is reduced or discontinued (e.g., when the subject is stable), and treatment with the anti-IL-1β antibody or fragment is increased (e.g., higher dose, more frequent dosing, longer treatment regimen). In yet another embodiment, the at least one other medically accepted treatment for the disease, condition or complication is maintained and treatment with the anti-IL-1β antibody or fragment is reduced or discontinued (e.g., lower dose, less frequent dosing, shorter treatment regimen). In yet another embodiment, the at least one other medically accepted treatment for the disease, condition or complication and treatment with the anti-IL-1β antibody or fragment are reduced or discontinued (e.g., lower dose, less frequent dosing, shorter treatment regimen)

In preferred methods of treating or preventing gout, anti-IL-1β antibody or fragment thereof is administered to the subject according to the aforementioned numbers of doses, amounts per dose and/or intervals between dosing. Alternatively, the anti-IL-1β antibody or fragment may be administered as one or more initial doses of the aforementioned amounts that are lower than one or more subsequent dose amounts. By providing the initial dose(s) in a lower amount, the effectiveness and/or tolerability of the treatment may be enhanced. For example, in a non-limiting embodiment of the invention, one or more initial doses (e.g., 1, 2, 3, 4, 5) of an amount of antibody or fragment $\leq 1$ mg/kg (e.g., $\leq 0.9$ mg/kg, $\leq 0.8$ mg/kg, $\leq 0.7$ mg/kg, $\leq 0.6$ mg/kg, $\leq 0.5$ mg/kg, $\leq 0.4$ mg/kg, $\leq 0.3$ mg/kg, $\leq 0.2$ mg/kg, $\leq 0.1$ mg/kg, $\leq 0.05$ mg/kg, $\leq 0.03$ mg/kg, $\leq 0.01$ mg/kg) may be administered, followed by one or more subsequent doses in an amount greater than the initial dose(s) (e.g., $\geq 0.01$ mg/kg, $\geq 0.03$ mg/kg, $\geq 0.1$ mg/kg, $\geq 0.3$ mg/kg $\geq 0.5$ mg/kg, $\geq 0.6$ mg/kg, $\geq 0.7$ mg/kg, $\geq 0.8$ mg/kg, $\geq 0.9$ mg/kg, $\geq 1.0$ mg/kg, $\geq 1.5$ mg/kg, $\geq 2$ mg/kg, $\geq 2.5$ mg/kg, $\geq 3$ mg/kg, $\geq 3.5$ mg/kg, $\geq 4$ mg/kg, $\geq 4.5$ mg/kg, $\geq 5$ mg/kg). The invention contemplates that each dose of antibody or fragment may be administered at one or more sites.

Methods of treating or preventing a disease or condition in accordance with the present invention may use a pre-determined or "routine" schedule for administration of the antibody or fragment. As used herein a routine schedule refers to a predetermined designated period of time between dose administrations. The routine schedule may encompass periods of time which are identical or which differ in length, as long as the schedule is predetermined. Any particular combination would be covered by the routine schedule as long as it is determined ahead of time that the appropriate schedule involves administration on a certain day.

The invention further contemplates that IL-1β antibodies or fragments used in accordance with the methods provided herein, may be administered in conjunction with more traditional treatment methods and pharmaceutical compositions (e.g., active agents). Such compositions may include for example, nonsteroidal anti-inflammatory drugs (NSAIDs) corticosteroids, adrenocorticotropic hormone, and colchicines. In certain embodiments, the antibodies and fragments used in accordance with the invention may prevent or delay the need for additional treatment methods or pharmaceutical compositions. In other embodiments, the antibodies or fragments may reduce the amount, frequency or duration of additional treatment methods or pharmaceutical compositions.

Alternatively, methods of treating or preventing a disease or condition in accordance with the present invention may use a schedule for administration of the antibody or fragment that is based upon the presence of disease symptoms and/or changes in any of the assessments herein as a means to determine when to administer one or more subsequent doses. Similar, this approach may be used as a means to determine whether a subsequent dose should be increased or decreased, based upon the effect of a previous dose.

Diagnosis of such diseases or conditions in patients, or alternatively the risk for developing such diseases or conditions may be according to standard medical practices known in art. Following administration of an anti-IL-1β antibodies or fragment, clinical assessments for a treatment or preventative effect on gout are well known in the art and may be used as a means to monitor the effectiveness of methods of the invention. For example, response to treatment of gout may be assessed based on a clinical assessment of the acute gout episode that includes a physician's assessment assessing redness, tenderness, and swelling (none of which are attributable to other causes), a physician's global assessment, a subject pain self-assessment, a patient's global assessment, and/or a HAQ. In one embodiment, efficacy of treatment is assessed by a reduction in joint pain of at least 50%, at least 60%, at least 70%, at least 80%, at least 90%, or about 100%. In another embodiment, the reduction in join pain occurs in less than about 48 hours, less than about 36 hours, less than about 24 hours. The clinical assessment of acute gout may include one or more of the following components:

Physician's Assessments:
  Physician's Global Assessment (10-point analog scale)
  Physician's assessment of erythema (10-point analog scale)
  Physician's assessment of heat (10-point analog scale)
  Physician's assessment of swelling (10-point analog scale)
Subject's Assessments:
  Patient's Global Assessment (10-point analog scale)
  Pain at rest (10-point analog scale)
  Pain on weight-bearing/movement (10-point analog scale)
  Health Assessment Questionnaire (HAQ)

One or more secondary endpoints, such as for example C-reactive protein (CRP) levels and/or erythrocyte sedimentation rate (ESR) also may be determined in order to assess efficacy of the treatment. A decrease in CRP levels of ≥0.2, ≥0.4, ≥0.6, ≥0.8, ≥1.0, ≥1.4, ≥1.8, ≥2.2, ≥2.6, ≥3.0 mg/L; alternatively a decrease of >20%, >30%, >40%, >50%, >60%, >70%, >80%, >90%, >95% from pre-treatment levels is indicative of therapeutic effect. A decrease in ESR of >20%, >30%, >40%, >50%, >60%, >70%, >80%, >90%, >95%, >98% from pre-treatment levels is indicative of therapeutic effect. The disclosure provides a method of treating gout in a subject (e.g., human subject), the method comprising administering (e.g., in a therapeutically effective amount) an anti-IL-1β antibody or fragment thereof to the subject, wherein the dose of the antibody or fragment is sufficient to achieve at least a 50% reduction in joint pain and at least a 20% decrease in CRP levels, at least a 30% decrease in CRP levels, at least a 40% decrease in CRP levels, at least a 50% decrease in CRP levels, at least a 60% decrease in CRP levels, at least a 70% decrease in CRP levels, at least a 80% decrease in CRP levels, and/or at least a 90% decrease in CRP levels. In a preferred embodiment, the dose of the antibody or fragment is sufficient to achieve at least a 50% reduction in joint pain and at least a 20% decrease in ESR, at least a 40% decrease in ESR, at least a 50% decrease in ESR, at least a 60% decrease in ESR, at least a 70% decrease in ESR, at least a 80% decrease in ESR, and/or at least a 90% decrease in ESR.

The disclosure also provides a method of treating gout in a subject (e.g., human subject), the method comprising administering (e.g., in a therapeutically effective amount) an anti-IL-1β antibody or fragment thereof to the subject, wherein the dose of the antibody or fragment is sufficient to achieve at least a 50% reduction in joint pain, at least a 20% decrease in CRP levels and at least a 20% decrease in ESR. In one embodiment, the dose of the antibody or fragment is sufficient to achieve at least a 50% reduction in joint pain, at least a 30% decrease in CRP levels and a 30% decrease in ESR. In another embodiment, the dose of the antibody or fragment is sufficient to achieve at least a 50% reduction in joint pain, at least a 40% decrease in CRP levels and a 40% decrease in ESR. In another embodiment, the dose of the anti-IL-1β antibody or fragment is sufficient to achieve at least a 60% reduction in joint pain, at least a 20% decrease in CRP levels and at least a 20% decrease in ESR. In another embodiment, the dose of the anti-IL-1β antibody or fragment is sufficient to achieve at least a 60% reduction in joint pain, at least a 40% decrease in CRP levels and at least a 40% decrease in ESR. In another embodiment, the dose of the anti-IL-1β antibody or fragment is sufficient to achieve at least a 60% reduction in joint pain, at least a 50% decrease in CRP levels and at least a 50% decrease in ESR. In yet another embodiment, the dose of the anti-IL-1β antibody or fragment is sufficient to achieve at least a 70% reduction in joint pain, at least a 20% decrease in CRP levels and at least a 20% decrease in ESR. In another embodiment, the dose of the anti-IL-1β antibody or fragment is sufficient to achieve at least a 70% reduction in joint pain, at least a 40% decrease in CRP levels and at least a 40% decrease in ESR. In another embodiment, the dose of the anti-IL-1 antibody or fragment is sufficient to achieve at least a 70% reduction in joint pain, at least a 50% decrease in CRP levels and at least a 50% decrease in ESR. In one embodiment, CRP levels may be measured by an ultra-sensitive CRP ELISA test. In another embodiment, ESR may be measured by a Westergren ESR test method.

Additional Embodiments

1. A method of treating gout in a subject, the method comprising administering an anti-IL-1β antibody or fragment thereof to the subject.
2. The method of embodiment 1, wherein the gout is chronic gout.
3. The method of embodiment 1, wherein the gout is acute gout.
4. The method of embodiments 1-3, wherein the antibody or antibody fragment binds to human IL-1β with a dissociation constant of about 10 nM or less.
5. The method of embodiments 4, wherein the antibody or antibody fragment binds to human IL-1β with a dissociation constant of about 1 nM or less.
6. The method of embodiments 5, wherein the antibody or antibody fragment binds to human IL-1β with a dissociation constant of about 500 pM or less.
7. The method of embodiments 6, wherein the antibody or antibody fragment binds to human IL-1β with a dissociation constant of about 250 pM or less.
8. The method of embodiment 7, wherein the antibody or antibody fragment binds to human IL-1β with a dissociation constant of about 10 pM or less.
9. The method of embodiment 8, wherein the antibody or antibody fragment binds to human IL-1β with a dissociation constant of about 1 pM or less.
10. The method of embodiment 9, wherein the antibody or antibody fragment binds to human IL-1β with a dissociation constant of about 0.5 pM or less.
11. The method of embodiment 10, wherein the antibody or antibody fragment binds to human IL-1β with a dissociation constant of about 0.3 pM or less.
12. The method of embodiments 1-11, wherein the anti-IL-1β antibody or antibody fragment is a neutralizing antibody.
13. The method of embodiments 1-11, wherein the anti-IL-1β antibody or antibody fragment binds to an IL-1β epitope such that the bound antibody or fragment substantially permits the binding of IL-1β to IL-1 receptor I (IL-1RI).
14. The method of embodiments 1-11, wherein the antibody or antibody fragment does not detectably bind to IL-1α, IL-1R or IL-1Ra.
15. The method of embodiments 1-11, wherein the antibody or antibody fragment binds to an epitope contained in the sequence ESVDPKNYPKKKMEKRFVFNKIE (SEQ ID NO: 1).

16. The method of embodiments 1-11, wherein the antibody or fragment thereof competes with the binding of an antibody having the light chain variable region of SEQ ID NO:5 and the heavy chain variable region of SEQ ID NO:6

17. The method of embodiments 1-11, wherein the antibody or antibody fragment binds to an epitope incorporating Glu64 of IL-1β.

18. The method of embodiments 1-11, wherein the antibody or antibody fragment binds to amino acids 1-34 of the N terminus of IL-1β.

19. The method of embodiments 1-11, wherein the antibody or antibody fragment is human engineered or humanized.

20. The method of embodiments 1-11, wherein the antibody or antibody fragment is human.

21. The method of embodiments 1-20, wherein the antibody or antibody fragment is administered in one or more doses of 3 mg/kg or less of antibody or fragment.

22. The method of embodiment 21, wherein the antibody or antibody fragment is administered in one or more doses of 1 mg/kg or less of antibody or fragment.

23. The method of embodiment 22, wherein the antibody or antibody fragment is administered in one or more doses of 0.3 mg/kg or less of antibody or fragment.

24. The method of embodiment 23, wherein the antibody or antibody fragment is administered in one or more doses of 0.1 mg/kg or less of antibody or fragment.

25. The method of embodiment 24, wherein the antibody or antibody fragment is administered in one or more doses of 0.03 mg/kg or less of antibody or fragment.

26. The method of embodiment 25, wherein the antibody or antibody fragment is administered in one or more doses of 0.01 mg/kg or less of antibody or fragment.

27. The method of embodiment 26, wherein the antibody or antibody fragment is administered in one or more doses of 0.003 mg/kg or less of antibody or fragment.

28. The method of embodiment 27, wherein the antibody or antibody fragment is administered in one or more doses of 0.001 mg/kg or less of antibody or fragment.

29. The method of embodiments 21-28, wherein the one or more doses are at least 0.001 mg/kg of antibody or fragment.

30. The method of embodiments 21-26, wherein the one or more doses are at least 0.01 mg/kg of antibody or fragment.

31. The method of embodiments 1-20, wherein the antibody or antibody fragment is administered in one or more doses of 0.001 mg/kg to 1 mg/kg.

32. The method of embodiment 31, wherein the antibody or antibody fragment is administered in one or more doses of 0.001 mg/kg to 0.3 mg/kg.

33. The method of embodiment 31, wherein the antibody or antibody fragment is administered in one or more doses of 0.003 mg/kg to 1 mg/kg.

34. The method of embodiment 33, wherein the antibody or antibody fragment is administered in one or more doses of 0.003 mg/kg to 0.3 mg/kg.

35. The method of embodiments 1-20, wherein the antibody or fragment is administered as a fixed dose, independent of a dose per subject weight ratio.

36. The method of embodiment 35, wherein the antibody or fragment is administered in one or more doses of 500 mg or less of antibody or fragment.

37. The method of embodiment 36, wherein the antibody or fragment is administered in one or more doses of 250 mg or less of antibody or fragment.

38. The method of embodiment 37, wherein the antibody or fragment is administered in one or more doses of 100 mg or less of antibody or fragment.

39. The method of embodiment 38, wherein the antibody or fragment is administered in one or more doses of 25 mg or less of antibody or fragment.

40. The method of embodiment 39, wherein the antibody or fragment is administered in one or more doses of 10 mg or less of antibody or fragment.

41. The method of embodiment 40, wherein the antibody or fragment is administered in one or more doses of 1.0 mg or less of antibody or fragment.

42. The method of embodiments 35-41, wherein the antibody or fragment is administered in one or more doses of at least 0.1 mg of antibody or fragment.

43. The method of embodiment 42, wherein the antibody or fragment is administered in one or more doses of at least 1.0 mg of antibody or fragment.

44. The method of embodiments 35-40, wherein the antibody or fragment is administered in one or more doses of at least 10 mg of antibody or fragment.

45. The method of embodiments 1-44, wherein the anti-IL-1β antibody or fragment is administered by subcutaneous, intravenous or intramuscular injection 46. The method of embodiments 1-45, wherein administration of an initial dose of the antibody or antibody fragment is followed by the administration of one or more subsequent doses.

47. The method of embodiments 1-45, wherein administration of an initial dose of the antibody or antibody fragment is followed by the administration of one or more subsequent doses, and wherein said one or more subsequent doses are in an amount that is approximately the same or less than the initial dose.

48. The method of embodiments 1-45, wherein administration of an initial dose of the antibody or antibody fragment is followed by the administration of one or more subsequent doses, and wherein at least one of the subsequent doses is in an amount that is more than the initial dose.

49. The method of embodiments 1-48, wherein the dose of the antibody or fragment is sufficient to achieve at least a 50% reduction in joint pain.

50. The method of embodiment 49, wherein the dose of the antibody or fragment is sufficient to achieve at least a 60% reduction in joint pain.

51. The method of embodiment 50, wherein the dose of the antibody or fragment is sufficient to achieve at least a 70% reduction in joint pain.

52. The method of embodiment 51, wherein the dose of the antibody or fragment is sufficient to achieve at least a 80% reduction in joint pain.

53. The method of embodiment 52, wherein the dose of the antibody or fragment is sufficient to achieve at least a 90% reduction in joint pain.

54. The method of embodiment 52, wherein the dose of the antibody or fragment is sufficient to achieve a 95% reduction in joint pain.

55. The method of embodiments 1-54, wherein the dose of the antibody or fragment is sufficient to achieve at least a 20% decrease in CRP levels.

56. The method of embodiment 55, wherein the dose of the antibody or fragment is sufficient to achieve at least a 30% decrease in CRP levels.

57. The method of embodiment 56, wherein the dose of the antibody or fragment is sufficient to achieve at least a 40% decrease in CRP levels.

58. The method of embodiment 57, wherein the dose of the antibody or fragment is sufficient to achieve at least a 50% decrease in CRP levels.

59. The method of embodiment 58, wherein the dose of the antibody or fragment is sufficient to achieve at least a 70% decrease in CRP levels.
60. The method of embodiment 59, wherein the dose of the antibody or fragment is sufficient to achieve at least a 90% decrease in CRP levels.
61. The method of embodiments 1-54, wherein the dose of the antibody or fragment is sufficient to achieve at least a 20% decrease in ESR.
62. The method of embodiment 61, wherein the dose of the antibody or fragment is sufficient to achieve at least a 40% decrease in ESR.
63. The method of embodiment 62, wherein the dose of the antibody or fragment is sufficient to achieve at least a 60% decrease in ESR.
64. The method of embodiment 63, wherein the dose of the antibody or fragment is sufficient to achieve at least a 70% decrease in ESR.
65. The method of embodiment 64, wherein the dose of the antibody or fragment is sufficient to achieve at least a 80% decrease in ESR.
66. The method of embodiment 65, wherein the dose of the antibody or fragment is sufficient to achieve at least a 90% decrease in ESR.
67. The method of embodiments 1-54, wherein the dose of the antibody or fragment is sufficient to achieve at least a 50% reduction in joint pain, at least a 20% decrease in CRP and at least a 20% decrease in ESR.
68. The method of embodiment 67, wherein the dose of the antibody or fragment is sufficient to achieve at least a 30% decrease in CRP and at least a 30% decrease in ESR.
69. The method of embodiment 68, wherein the dose of the antibody or fragment is sufficient to achieve at least a 40% decrease in CRP and at least a 40% decrease in ESR.
70. The method of embodiments 1-69, wherein said method is in conjunction with at least one additional treatment method, said additional treatment method comprising administering at least one pharmaceutical composition comprising an active agent other than an IL-1β antibody or fragment.
71. The method of embodiment 70, wherein said at least one pharmaceutical composition comprising an active agent other than an IL-1β antibody or fragment is selected from the group consisting of a nonsteroidal anti-inflammatory drug (NSAID), a corticosteroid, an adrenocorticotropic hormone, and a colchicines.
72. The method of embodiments 1-71, wherein the antibody or fragment thereof has a lower $IC_{50}$ than an IL-1β receptor antagonist in a human whole blood IL-1β inhibition assay that measures IL-1β induced production of IL-8.
73. The use of an anti-IL-1β antibody or fragment thereof which has a lower $IC_{50}$ than an IL-1β receptor antagonist in a human whole blood IL-1β inhibition assay that measures IL-1β induced production of IL-8, in the manufacture of a composition for use in the treatment of gout.
74. The method of embodiment 72 or the use according to embodiment 73, wherein the IL-1β receptor antagonist is anakinra.

EXAMPLES

The following examples are intended merely to further illustrate the practice of the present invention, but should not be construed as in any way limiting its scope. The disclosures of all patent and scientific literatures cited within are hereby expressly incorporated in their entirety by reference.

Example 1

Inhibition of IL-1, Using a High Affinity IL-1, Antibody in an In Vitro Cell Based Assay, with IL-1 Induced Production of IL-8 as a Read-Out The inhibitory effect of the IL-1β-specific antibody was compared to a non-antibody inhibitor of the IL-1 pathway, KINERET® (anakinra), which is a recombinant IL-1 receptor antagonist (IL-1Ra). Fresh, heparinized peripheral blood was collected from healthy donors. 180 µl of whole blood was plated in a 96-well plate and incubated with various concentrations of the antibody AB7 (U.S. application Ser. No. 11/472,813, WO 2007/002261) and 100 pM rhIL-1β. For KINERET® (anakinra) treated samples, KINERET® (anakinra) and rhIL-1β were combined 1:1 prior to mixing with blood. Samples were incubated for 6 hours at 37° C. with 5% $CO_2$. Whole blood cells were then lysed with 50 µl 2.5% Triton X-100. The concentration of interleukin-8 (IL-8) in cleared lysates was assayed by ELISA (Quantikine human IL-8 ELISA kit, R&D Systems) according to manufacturer's instructions. IL-8 concentrations in AB7 and KINERET® (anakinra) treated samples were compared to a control sample treated with anti-KLH control. The results are depicted in FIG. 1 and summarized in Table 6. $IC_{50}$ is the concentration of antibody required to inhibit 50% of IL-8 released by IL-1β stimulation.

TABLE 1

| | $IC_{50}$ (pM) |
|---|---|
| AB7 | 1.9 pM |
| Kineret ® | 53.4 pM |

These results demonstrate the in vitro potency of AB7, as measured by inhibition of IL-1β stimulated release of IL-8. The results showing greater potency compared with KINERET® (anakinra) indicate that the antibody will have IL-1β inhibitory efficacy in vivo.

Example 2

In Vivo Inhibition of the Biological Activity of Human IL-1β Using IL-1β-Specific Antibodies, as Measured by the Impact on IL-1β Stimulated Release of IL-6

To confirm the in vivo efficacy of AB7, its ability to block the biological activity of human IL-1β was tested in mice. Details of the assay are described in Economides et al., Nature Med., 9: 47-52 (2003). Briefly, male C57/Bl6 mice (Jackson Laboratory Bar Harbor, Me.) were injected intraperitoneally with titrated doses of AB7, another IL-1β antibody, AB5, or a control antibody. Twenty-four hours after antibody injection, mice were injected subcutaneously with recombinant human IL-1β (rhIL-1β) (from PeproTech Inc., Rocky Hill, N.J.) at a dose of 1 µg/kg. Two hours post-rhIL-1β injection (peak IL-6 response time), mice were sacrificed, and blood was collected and processed for serum. Serum IL-6 levels were assayed by ELISA (BD Pharmingen, Franklin Lakes, N.J.) according to the manufacturer's protocol. Percent inhibition was calculated from the ratio of IL-6 detected in experimental animal serum to IL-6 detected in control animal serum (multiplied by 100).

Figure 2A:
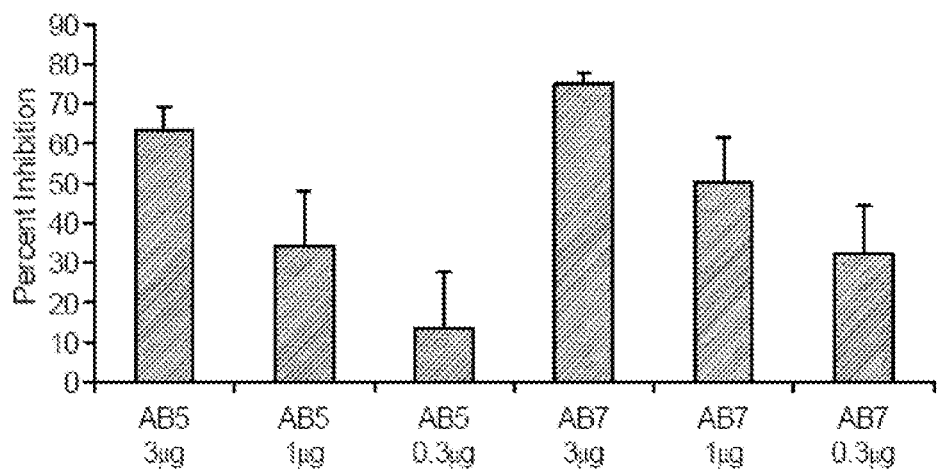
FIG. 2A is a graph showing the results of an in vivo IL-1β inhibition experiment for the antibodies designated AB5 and AB7 involving IL-1 stimulated release of IL-6.

The results are set forth in FIG. 2A. The ability to inhibit the in vivo activity of IL-1β was assessed as a function of IL-1β stimulated IL-6 levels in serum. As illustrated by FIG. 2A, the AB7 and AB5 antibodies were effective for inhibiting the in vivo activity of human IL-1β. These results also show that a single injection of AB7 or AB5 can block the systemic action to IL-1β stimulation and that such antibodies are useful for the inhibition of IL-1β activity in vivo.

Figure 2B:
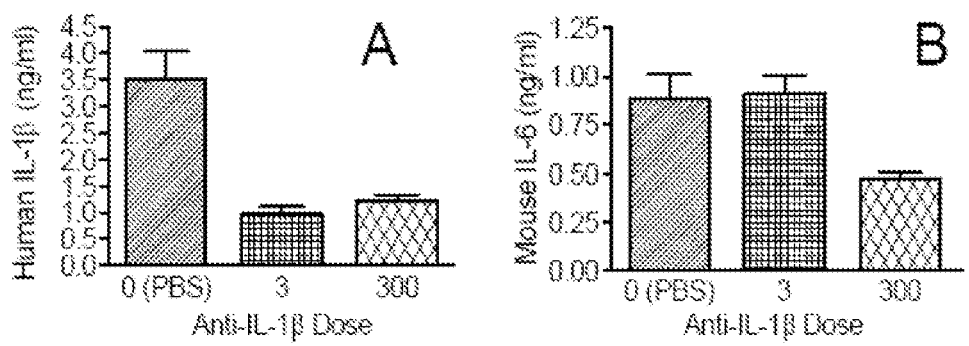
FIG. 2B is a graph showing the results of an in vivo IL-1β inhibition experiment for the antibodies designated AB7 involving IL-1 stimulated release of IL-6, and comparing inhibition of human (panel A) versus mouse (panel B) IL-1β.

A similar experiment was performed to further demonstrate the ability of AB7 to neutralize mouse IL-1β in vivo, to support the use of this antibody in mouse models of disease. It was determined that AB7 has an affinity for human IL-1β that is ~10,000 times greater than the affinity for mouse IL-1β, and an in vitro potency in the D10.G4.1 assay that is ~1,000 times greater than that for mouse IL-1β. In the C57BL/6 mouse model with IL-6 readout, the mice were injected with AB7 (3 or 300 ug) or PBS vehicle control i.p. 24 hours before a s.c. injection of human (FIG. 2B, panel A) or mouse (FIG. 2B, panel B) IL-1β (20 ng). Blood was drawn 2 hours later and serum samples were analyzed for IL-6 levels via ELISA. These data show maximum suppression of IL-6 levels (~75%) induced by human IL-1β at 3 µg (panel A), whereas submaximum suppression of IL-6 levels (~50%) induced by mouse IL-1β was demonstrated with 300 µg (panel B). These results are consistent with the observation of far greater affinity and in vitro potency of the AB7 antibody for human IL-1β, as compared to mouse IL-1β. In addition, the data indicate that this antibody may be used for mouse in vivo disease models with an appropriate higher dose than would be needed for treatment of human subjects, where the antibody has far superior affinity and potency. In the case of other IL-1β antibodies, such as for example other antibodies disclosed and/or cited herein, that do not exhibit significantly lower affinity and in vitro potency for mouse IL-1β, dose adjustments to higher levels in mouse models may not be necessary.

Example 3

Pharmacokinetics of an Anti-IL-1β Antibody Following Administration of a Single Intravenous or Subcutaneous Dose to Rats To examine the pharmacokinetic profile, an IL-1β antibody designated AB7 was administered to adult male rats as an intravenous (IV) bolus into the tail vein at doses of 0.1, 1.0, or 10 mg/kg (Groups 1, 2, and 3 respectively) or a subcutaneous (SC) dose between the shoulder blades at 1.0 mg/kg (Group 4). Blood samples were collected via the jugular vein cannula or the retro-orbital sinus at specified times for up to 91 days after dosing. Blood samples were centrifuged to obtain serum. Samples were analyzed for the concentration of anti-IL-1β antibody using an alkaline phosphatase-based ELISA assay as follows.

IL-1β (Preprotech) was diluted to 0.5 µg/mL in PBS and 50 µL of this solution was added to wells of Nunc-Immuno Maxisorp microtiter plates (VWR) and incubated overnight at 2-8° C. The antigen solution was removed and 200 µL of blocking buffer [1% bovine serum albumin (BSA) in 1×PBS containing 0.05% Tween 20] was added to all wells and incubated for 1 hour at room temperature. After blocking, the wells were washed three times with wash buffer (1×PBS, containing 0.05% Tween 20). Standards, samples and controls were diluted in sample diluent (25% Rat Serum in 1×PBS containing 1% BSA and 0.05% Tween 20). Anti-IL-1β antibody standard solutions were prepared as serial two-fold dilutions from 2000 to 0.24 ng/mL. Each replicate and dilution of the standards, samples and controls (50 µL) were transferred to the blocked microtiter plates and incubated for 1 hour at 37° C. After incubation, the wells were washed 3 times with wash buffer. Alkaline phosphatase conjugated goat anti-human IgG (H+L) antibody (Southern Biotech Associates Inc, Birmingham, Ala.) was diluted 1/1000 in conjugate diluent (1% BSA in 1×PBS containing 0.05% Tween 20). Fifty µL of the diluted conjugate was added to all wells except for the BLANK wells, which received 50 µL of conjugate diluent only. The plates were incubated for 1 hour at 37° C. and then all wells were washed 3 times with wash buffer and 3 times with deionized water. The substrate p-nitrophenylphosphate (1 mg/mL in 10% diethanolamine buffer, pH 9.8) was added to all wells and color development was allowed to proceed for 1 hour at room temperature, after which 50 µL of 1 N NaOH was added to stop the reaction. The absorbance at 405 nm was determined using a SPECTRAmax M2 Plate Reader (Molecular Devices, Menlo Park, Calif.) and a standard curve was then plotted as $A_{405}$ versus ng/mL of antibody standard. A regression analysis was performed and concentrations were determined for samples and controls by interpolation from the standard curve. The limit of quantification was 40 ng/mL.

Figure 3:
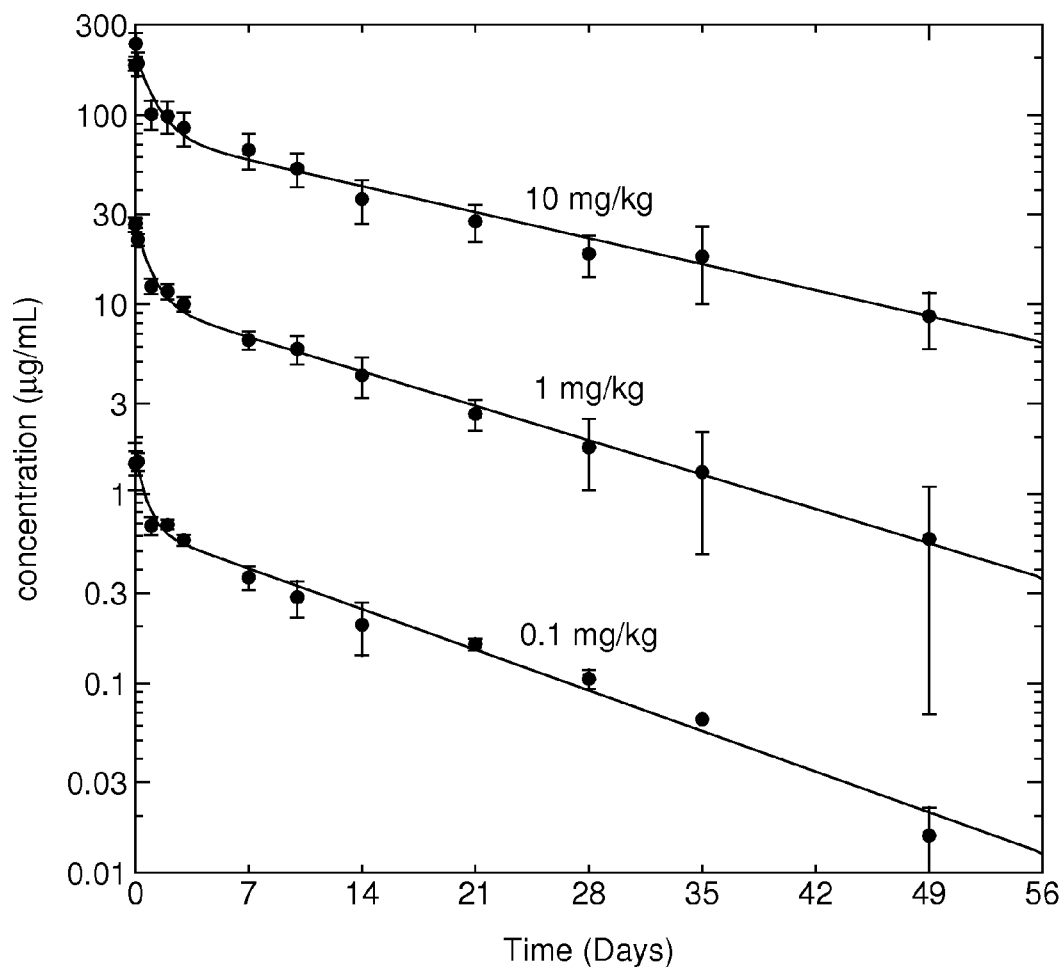
FIG. 3 is a graph showing serum concentrations following administration 0.1, 1 or 10 mg/kg of an anti-IL-1β antibody in rats.
Figure 4:
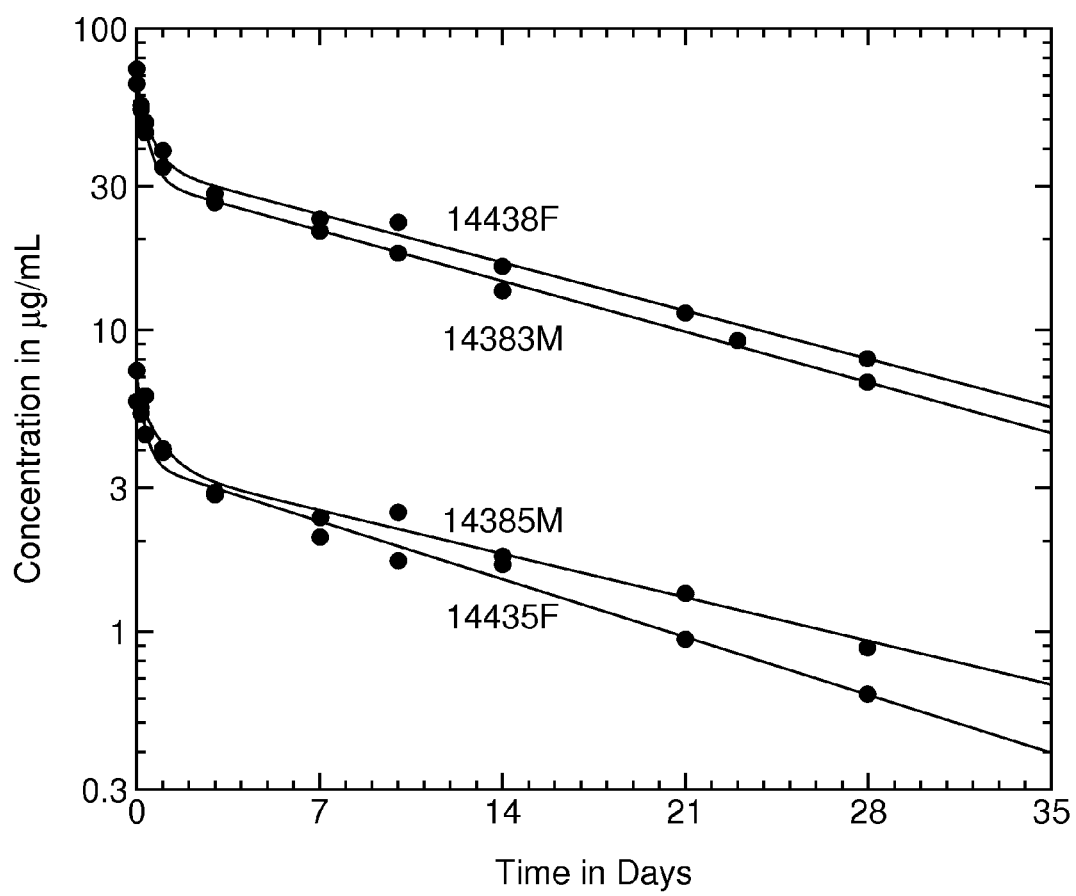
FIG. 4 is a graph showing serum concentrations following administration of 0.3 or 3 mg/kg of an anti-IL-1β antibody in Cynomolgus monkeys.

As shown in FIG. 3, serum concentrations declined bi-exponentially among the IV dose groups. A compartmental analysis was performed on the individual animal data, and resulting pharmacokinetic parameters were averaged for each dose group excluding those animals in which a RAHA response was generated. The serum levels of anti-IL-1β antibody declined with an average alpha phase half-life of 0.189±0.094 to 0.429±0.043 days (4.54 to 10.3 hours) and a beta phase half-life of 9.68±0.70 to 14.5±1.7 days. Among rats receiving a 1 mg/kg subcutaneous dose of AB7 serum levels increased to a peak of 4.26±0.065 µg/mL by 2-3 days, and declined with a half-life of 2.59±0.25 days.

Example 4

Pharmacokinetics of an Anti-IL-1β Antibody Following Administration of a Single Intravenous Dose To Cynomolgus Monkeys Adult male and female cynomolgus monkeys received the anti-IL-1β antibody designated AB7 as an intravenous (IV) single bolus injection at doses of 0.3, 3.0, or 30 mg/kg. Blood samples were collected from animals prior to dose, 5 minutes, 4 and 8 hours post dose on Day 1, and Days 2, 4, 8, 11, 15, 22, 29, 43 and 56. Samples were analyzed for the concentration of anti-IL-1β antibody using an alkaline phosphatase-based ELISA assay as follows.

IL-1β solution was diluted to 0.5 µg/mL in PBS and 50 µL of this solution was added to wells of Nunc-Immuno Maxisorp microtiter plates (VWR) and incubated overnight at 2-8° C. The antigen solution was removed and 200 µL of blocking buffer [1% bovine serum albumin (BSA) in 1×PBS containing 0.05% Tween 20] was added to all wells and then incubated for 1-4 hours at room temperature. After blocking, the wells of each plate were washed three times with wash buffer (1×PBS, containing 0.05% Tween 20). Standards, samples, and controls were diluted in sample diluent (2% Normal Cynomolgus Serum (NCS) in 1×PBS containing 1% BSA and 0.05% Tween 20). Anti-IL-1β standard solutions were prepared as serial two-fold dilutions from 8000 ng/mL. Each replicate and dilution of the standards, samples, and controls (50 µL) were transferred to the blocked microtiter plates and incubated for 1 hour at 37° C. After the primary incubation, the wells were washed 3 times with wash buffer and 50 µL of biotinylated rhIL-1 beta was added to all wells. The plates were then incubated for 1 hour at 37° C. The wells were washed 3 times with wash buffer and a tertiary incubation with fifty µL of diluted alkaline phosphatase conjugated streptavidin was added to all wells except for the BLANK wells, which received 50 µL of diluent only. The plates were incubated for 30 minutes at 37° C., and then all wells were washed 3 times with wash buffer and 3 times with deionized water. The substrate p-nitrophenylphosphate (1 mg/mL in 10% diethanolamine buffer, pH 9.8) was added to all wells. Color development was allowed to proceed in the dark for 1 hour at room temperature, after which 50 µL of 1 N NaOH was added to stop the reaction. The absorbance at 405 nm was determined for all wells using a SPECTRAmax M2 Plate Reader (Molecular Devices, Menlo Park, Calif.). A standard curve was then plotted as $A_{405}$ versus ng/mL of anti-IL-1β standard. A 4-parameter regression analysis was performed and concentrations were determined for samples and controls by interpolation from the standard curve. The limit of quantification was 40 ng/mL.

Figure 5:
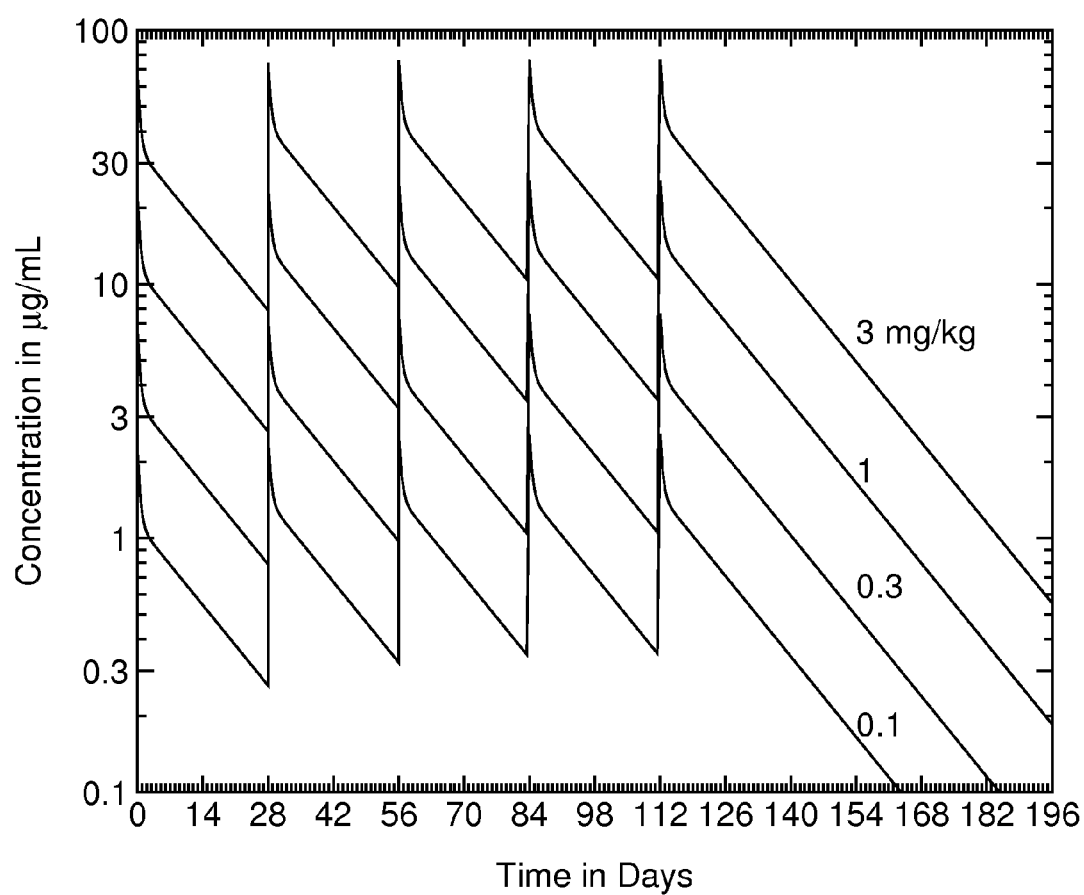
FIG. 5 is a graph modeling plasma concentration profiles of an anti-IL-1β antibody in Cynomolgus monkeys following five monthly doses of 0.1, 0.3, 1 or 3 mg/kg.

For the single dose 0.3 and 3 mg/kg groups, the serum anti-IL-1β antibody levels declined with an average alpha phase half-life of 9.40±2.00 hours, followed by a beta phase half-life of 13.3±1.0 days (FIG. 5). In cynomolgus monkeys receiving a single IV injection of 30 mg/kg, serum levels of antibody declined more rapidly, with alpha phase half life of 10.9±3.2 hours, followed by a beta phase half-life of 7.54±1.79 days. Modeling of plasma concentration-time profiles of 0.1, 0.3, 1 and 10 mg/kg doses administered at five monthly intervals also was performed and is shown in FIG. 5.

Example 5

Inhibition of Cytokine Production in Human Whole Blood by an IL-1β Antibody

Measuring cytokines in blood during a disease or the treatment of a disease can be useful for determining disease severity or response to a therapy. Usually, cytokine levels are measured in serum, but this method does not necessarily measure total cytokines. Many cytokines can be inside cells (intracellular). In addition, the ability for a cell to produce a cytokine may be more useful information than the level of circulating cytokine.

A method of stimulating whole blood was used to determine cytokine production and the effect of treating with an anti-IL-1β antibody. Blood was drawn from patients into sterile heparinized tubes and then 250 ul of the whole blood was added to each 4 mL orange top Corning sterile cryotube set up as follows:
Control Series
All tubes were pre-filled with 550 ul of RPMI. To tube 1 (control), 200 ul RPMI was added and to tubes 2-10, 100 ul additional RPMI was added. To each of tubes 2-10, 100 ul of dilutions of an anti-IL-1β antibody (AB7) was added.
Test Series
A similar series of antibody dilutions was set up as detailed above.
All tubes were mixed well using a 10 second vortex. Control series tubes A1-10 then received an additional 100 ul of RPMI, were vortexed 10 seconds, the screw cap tightly fixed and the tubes placed in incubator. To Test series tubes B1-10, 100 ul of heat-killed *Staphylococcus epidermidis* (final concentration of 1:1000 of stock resulting in a bacterium:white blood cell ration of 10:1) was added, the tubes were then vortexed for 10 seconds, capped and placed in 37° C. incubator. After 24 hours incubation, the cultures were all lysed with Triton X (0.5% final) to release the cell contents and the lysates were frozen. After lysis of the whole blood cultures, the tubes subjected to freeze thaw cycles and cytokine levels are measured by standard cytokine ELISA assays for human TNFα, IL-6, IFNγ, IL-8, IL-1α, IL-1Ra and IL-1β (R&D Systems, Minneapolis, Minn.).

Cytokines measured in the control series tubes, which contain only sterile culture medium and antibody (where indicated), reflect the spontaneous level of stimulation. In healthy subjects, very low levels of the various cytokines are found when measured after 24 hours of incubation. In patients with untreated diseases, the levels may be higher. The Test series of tubes additionally contained a defined amount of heat-killed *Staphylococcus epidermidis*, which stimulates production of a number of cytokines. If the anti-IL-1β antibody treatment is efficacious, this will be reflected by reduces cytokine production.

As shown in FIG. 6, the high affinity anti-IL-1β antibody AB7 was very effective at inhibiting the production of IL-1β in human blood. In an average of three human samples, the antibody inhibited the production of IL-1β induced by *Staphylococcus epidermidis* by 50% at 0.1 pM and by 75% at 3 pM. At 100 pM, inhibition was 100%. Interferon gamma (IFNγ) was induced by *Staphylococcus epidermidis* and AB7 reduced IFNγ induced by *Staphylococcus epidermidis* by 75% at 100 pM.

Example 6

Pharmacokinetics of an Anti-IL-1β Antibody Following Administration of a Single Intravenous Dose to Humans Pharmacokinetics of an IL-1β antibody having the aforementioned properties was demonstrated in a phase I human clinical study. Specifically, a double-blind, placebo controlled human clinical study was performed in Type 2 diabetes patients and data initially obtained from five patients receiving the IL-1β antibody designated AB7 (described above) at a dose of 0.01 mg/kg via constant rate intravenous infusion were used to examine pharmacokinetics.

Figure 7:
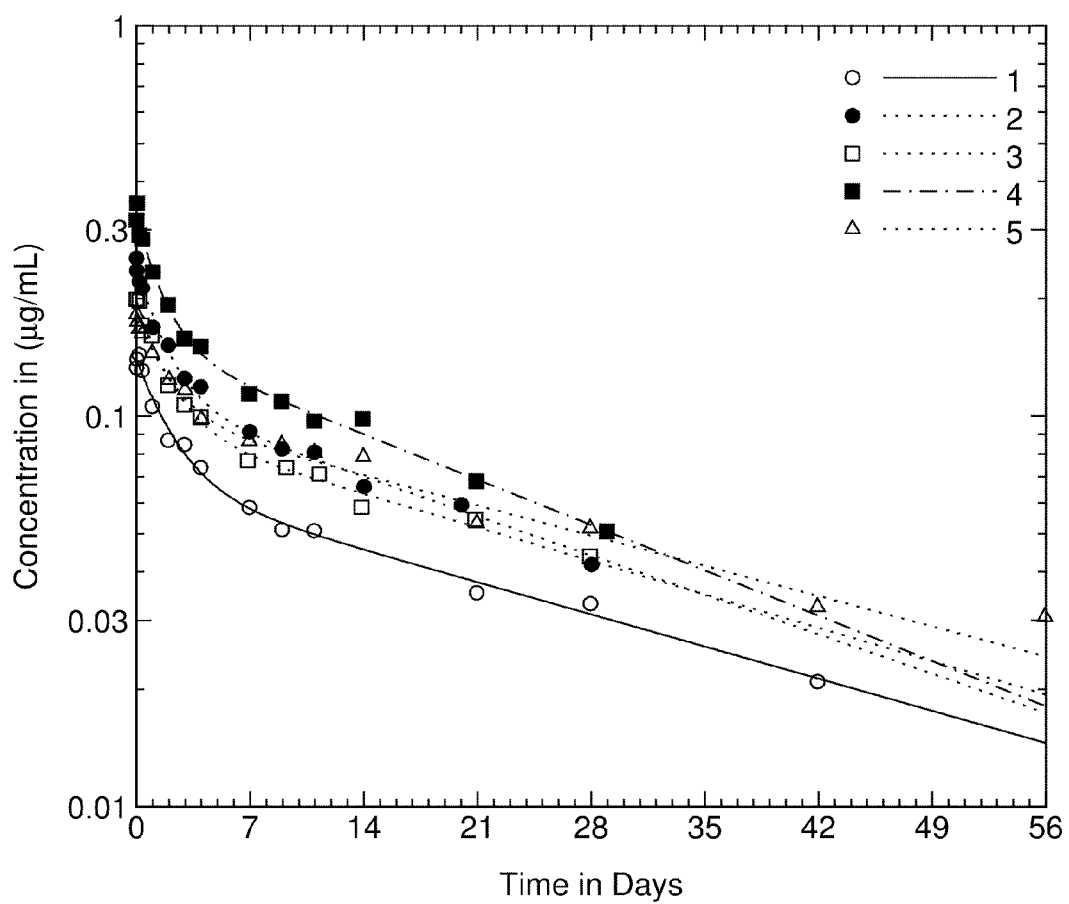
FIG. 7 is a graph showing the pharmacokinetics of AB7 in humans following administration of a dose of 0.01 mg/kg of antibody.

On study Day 1, antibody was administered either via a 30 minute constant rate intravenous infusion. Safety assessments, including the recording of adverse events, physical examinations, vital signs, clinical laboratory tests (e.g., blood chemistry, hematology, urinalysis), plasma cytokine levels, and electrocardiograms (ECGs) were conducted using standard medical practices known in the art. Blood samples were collected pre-dose administration and at days 0, 1, 2, 3, 4, 7, 9±1, 11±1, 14±1, 21±2, 28±2, 42±3, and 56±3 post-administration to assess IL-1β antibody levels (pharmacokinetics). Preliminary analysis of the pharmacokinetics of the IL-1β antibody in subjects receiving a single IV dose of 0.01 mg/kg showed serum concentration-time profiles with a terminal half-life of 22 days, clearance of 2.9 mL/day/kg and volume of distribution of the central compartment of 50 mL/kg, very similar to serum volume (FIG. 7).

Figure 8:
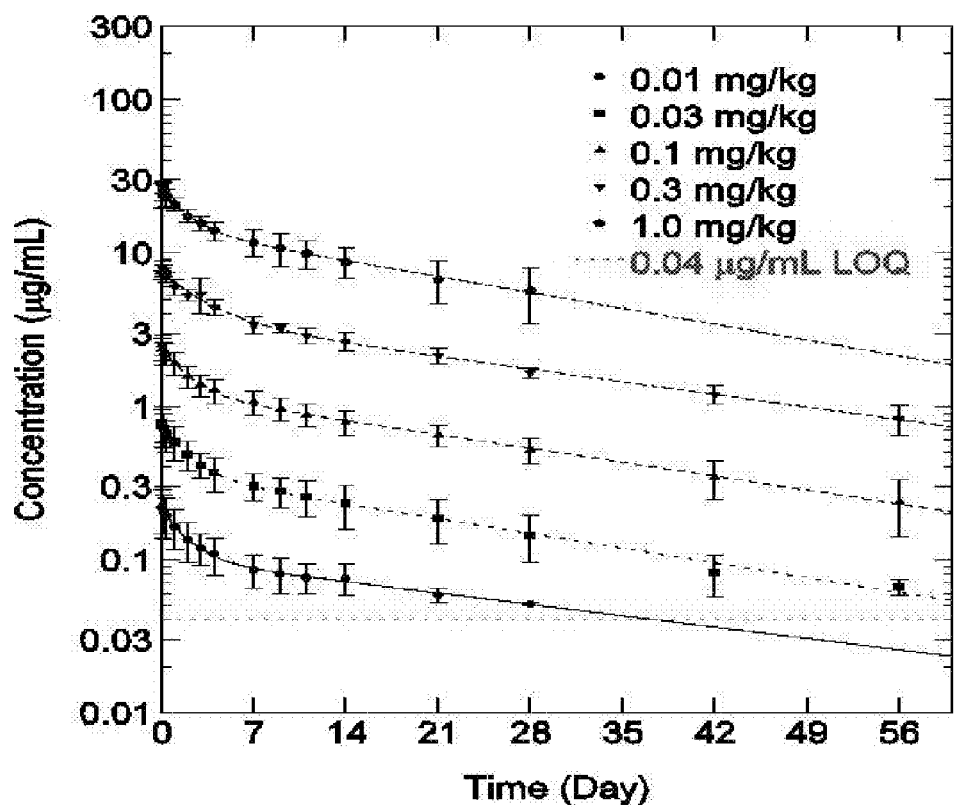
FIG. 8 is a graph showing serum concentrations following administration of 0.01, 0.03, 0.1, 0.3, or 1.0 mg/kg of an anti-IL-1β antibody in human subjects with Type 2 diabetes.

Interim analysis of pharmacokinetic data following IV administration of a single dose of AB7 (XOMA 052) in subjects through the 0.01, 0.03, 0.1, 0.3, or 1.0 mg/kg dose groups further confirmed that the serum concentration-time profiles with a terminal half-life of 22 days, clearance of 2.54 mL/day/kg and volume of distribution of the central compartment of 41.3 mL/kg, very similar to serum volume (FIG. 8).

Example 7

Effects of an IL-1β Antibody on CRP in Human Subjects with Type 2 Diabetes

Figure 9:
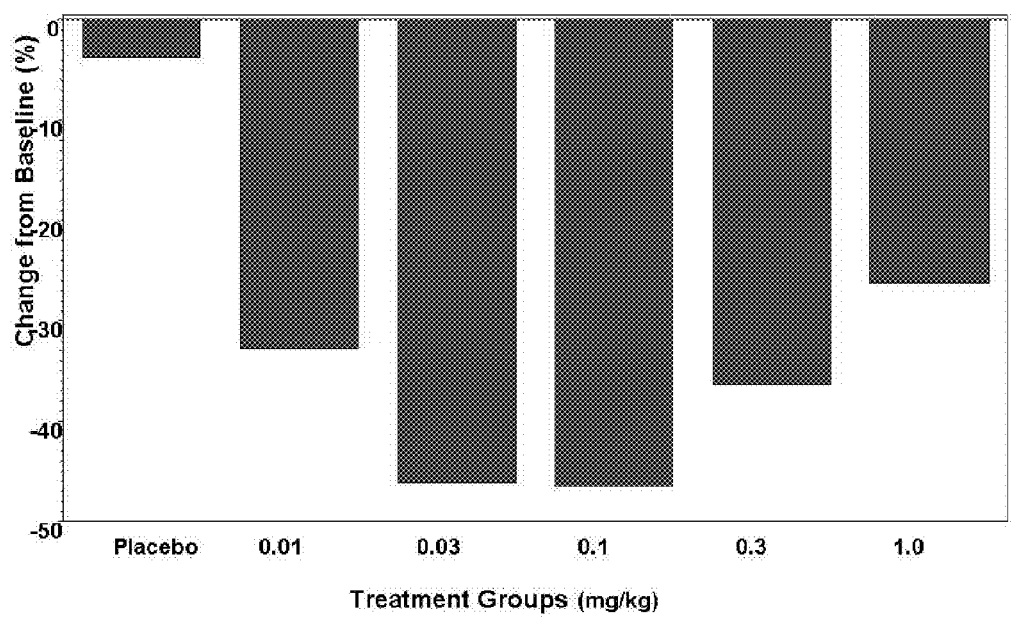
FIG. 9 is a graph showing median percent change in CRP at day 28 following administration of 0.01, 0.03, 0.1, 0.3, or 1.0 mg/kg of an anti-IL-1β antibody to human subjects with Type 2 diabetes.
Figure 10A:
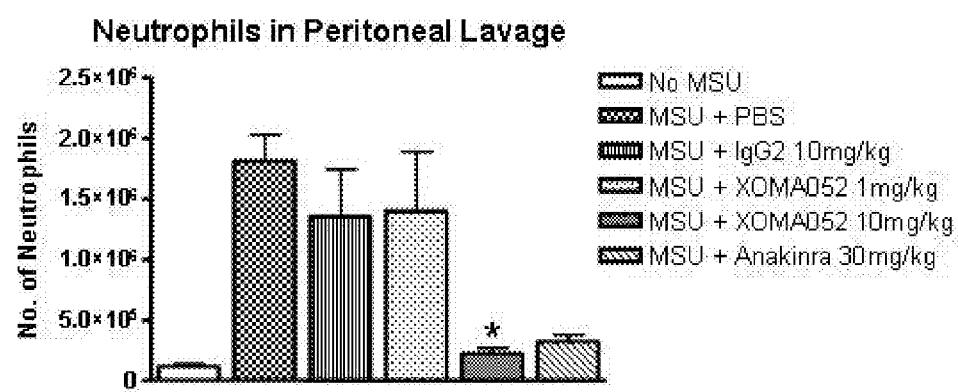
FIGS. 10A and 10B are graphs showing efficacy of an anti-IL-1β antibody in a mouse model of MSU-crystal induced acute gout.
Figure 10B:
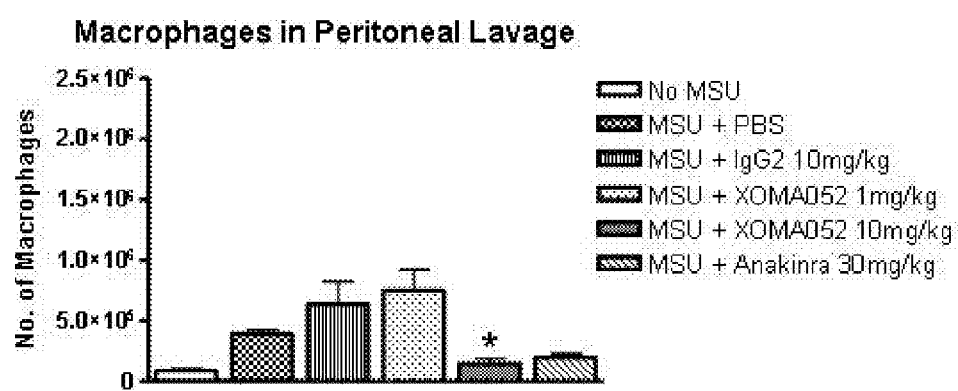

C-reactive protein (CRP), which is released by the liver in response to various stress triggers, including IL-6, produced in response to IL-1, also was measured in serum at the same time points as the PK samples to determine the activity of the antibody in human subjects. A single dose of XOMA 052 reduced ultra-sensitive C-reactive protein (usCRP) levels, a standard measure of systemic inflammation associated with multiple diseases and an indicator of cardiac risk, in all of the dose groups treated compared to placebo. As shown in FIG. 9, at 28 days after a single dose of XOMA 052, the median percent reductions in usCRP were 33, 46, 47, 36, and 26 for the 0.01, 0.03, 0.1, 0.3, and 1.0 mg/kg dose groups, respectively, compared to 4 percent for placebo. The activity resulting from a single administration of antibody at a dose of 0.01 mg/kg indicates that even lower doses may be used.

Example 8

Use of an IL-1, Antibody in the Treatment of Gout in an Animal Model

Efficacy of an IL-1β antibody, such as an antibody having the aforementioned properties or as described herein, was evaluated in an acute mouse model of gout. The acute mouse model of gout evaluates the ability of a therapeutic agent to block monosodium urate (MSU) crystal-induced acute peritonitis (Martinon et al., 2006, Nature 440:237-241). Specifically, peritonitis was induced by injecting 0.5 mg of MSU crystals into the peritoneal space of Balb/c mice. Mice were treated 2 hours earlier by intraperitoneal injection of isotype control antibody or anti-IL-1β antibody XOMA 052 (also referred to as AB7 herein, described above) at 10 mg/kg. For comparison, one group of mice received Anakinra at 30 mg/kg at the same time as MSU injection. After 6 hours, peritoneal lavage was performed and the lavage fluid was centrifuged to collect cells. Cells were counted and a fraction was used for cytospin and leukocyte differential counts. Peritonitis was measured by calculating the number of neutrophils in the lavage. The number of neutrophils is determined by multiplying the total cell count in the lavage by the percentage of neutrophils in the differential count. As shown in FIGS. 8A and 8B, the XOMA 052 antibody was able to block the neutrophil and macrophage infiltration, and reduce peritonitis induced by the MSU crystals relative to the PBS and isotype controls (p<0.05, unpaired t-test). There was no significant difference between treatment with 10 mg/kg XOMA 052 and 30 mg/kg Anakinra in the mouse model.

Example 9

Use of an IL-1β Antibody in the Treatment of Gout

IL-1β antibodies or fragments, such as those having the aforementioned properties or described herein, may be administered to a subject (e.g., human patient) for therapeutic treatment and/or prevention of gout. Specifically, in one example, an IL-1β antibody XOMA 052 (also known as AB7, described above) is used for the therapeutic treatment of patients displaying signs and symptoms of gout. Safety and effectiveness of the IL-1β antibody for gout are demonstrated in one or more human clinical studies, including for example a trial of the following design in subjects with recurrent acute gout.

Subjects may be included in the study if they meet all of the following criteria:
Acute gout diagnosed by meeting criteria from the 1977 Criteria for the Classification of Acute Arthritis of Primary Gout (American Rheumatism Association, ACR). A diagnosis of acute gout is confirmed by a) the presence of characteristic urate crystals in the joint fluid; b) a tophus proven or suspected to contain urate crystals by polarized light microscopy; or c) the presence of at least 7 of the following 12 clinical, laboratory, or radiographic phenomena:
More than one lifetime attack of acute arthritis
Maximum inflammation developed within 1 day
Attack of monoarticular arthritis
Observed joint redness
First metatarsophalangeal (MTP) joint painful or swollen
Unilateral first MTP joint attack
Unilateral tarsal joint attack
Tophus (proven or suspected)
Hyperuricemia
Asymmetric swelling within a joint on X-ray/exam
Subcorticol cysts without erosions on X-ray
Joint fluid culture negative for organisms during attack
At least two acute gout attacks within the previous year
Onset of the current acute episode must have occurred no more than 48 hours prior to study drug administration on Day 0 and the symptoms of the acute attack must not have significantly subsided prior to study drug dosing A phase ½, double-blind, placebo-controlled, parallel-group, single-dose study of the safety and pharmacokinetics of XOMA 052 antibody performed in subjects experiencing acute gout attacks. Subjects in parallel dose groups of six subjects each (multiple active drug groups and one placebo group) are enrolled to receive a single IV infusion of study drug (IL-1β antibody or placebo) at dose levels shown in the table below.

| Dose Group | Number of Subjects | Dose Regimen |
| --- | --- | --- |
| A | 6 | Single IV infusion of antibody at 0.03 mg/kg |
| B | 6 | Single IV infusion of antibody at 0.1 mg/kg |
| C | 6 | Single IV infusion of antibody at 0.3 mg/kg |
| D | 6 | Single IV infusion of antibody at 1.0 mg/kg |
| E | 6 | Single IV infusion of antibody at 3.0 mg/kg |
| F | 6 | Single IV infusion of placebo |

Subjects that meet all eligibility criteria are enrolled, randomized into one of the dose groups, and dosed on Day 0 with study drug (antibody or placebo). Subjects must be dosed within 48 hours of the onset of the new acute gout attack. A new attack is defined as one that follows at least 28 days in which the subject is free of acute gout symptoms.

Weekly assessments are performed through Day 28, followed by biweekly assessments through Day 56. Safety is assessed by pre- and post-treatment serial measurements of vital signs, clinical laboratory assessments, and the recording of adverse clinical events. PK data is collected and analyzed at the time points shown below.

Pharmacokinetic Assessment
Serum samples are collected on Day 0 (baseline) prior to study drug administration, and at selected time points after the administration of the study drug for the measurement of serum concentrations of IL-1β antibody.

From these serum concentrations, the appropriate pharmacokinetic parameters are calculated. These calculations are expected to employ compartmental and noncompartmental pharmacokinetic methods to estimate the following parameters: peak concentration, serum clearance, half-lives, volumes of distribution, and mean residence time. Population PK and PD analysis methods may be employed to better understand the PK/PD characteristics of the IL-1β antibody in this population.

The IL-1β antibody pharmacokinetics are evaluated for their correlation with biological markers and clinical outcome. In addition, an assessment is made of the correlation between drug exposure and any evidence of drug toxicity.

Biological and Clinical Activity

As measures of the biological activity of IL-1β antibody in subjects with acute recurrent gout, CRP and ESR are collected as inflammatory markers. The clinical status of the gout, including pain level and time course, is measured through periodic physician assessments and subject self-assessments. Clinical assessment of the acute gout episode includes a physician's assessment of redness, tenderness, and swelling (none of which are attributable to other causes), a physician's global assessment, and a subject pain self-assessment, a patient's global assessment, and a HAQ. Subjects are given a diary and asked to report on their symptoms every 2 hours during waking time in the first 24 hours post-dose, followed by two times per day through Day 7, once per day through Day 14, and only as symptoms recur thereafter.

The clinical assessment of acute gout includes the following components:

Physician's Assessments:
  Physician's Global Assessment (10-point analog scale)
  Physician's assessment of erythema (10-point analog scale)
  Physician's assessment of heat (10-point analog scale)
  Physician's assessment of swelling (10-point analog scale)

Subject's Assessments:
  Patient's Global Assessment (10-point analog scale)
  Pain at rest (10-point analog scale)
  Pain on weight-bearing/movement (10-point analog scale)
  Health Assessment Questionnaire (HAQ)

In addition, the following assessments are performed at various sample collection time points:

Serum collected at various time points is used to assess levels of adipokines and cytokines that may be produced by inflamed adipose tissue in gout patients. Such adipokines/cytokines include, for example, adiponectin, resistin, leptin, visfatin, PAI 1, TNFα, IL-1, IL-1Ra, IL-6, IL-8, RANTES, and MCP-1.

A whole blood sample is collected and assayed for cytokines that may include, for example, TNFα, IL-6, IFNγ, IL-8, and IL-1α.

| PK Sampling Schedule | |
|---|---|
| Time Point | All Groups |
| Day 0 | |
| Prior to infusion | X |
| EOI | X |
| EOI + 30 ± 5 min | X |
| EOI + 4 hr ± 15 min | X |
| Day 1 (24 ± 2 hr post EOI) | X |

| PK Sampling Schedule | |
|---|---|
| Time Point | All Groups |
| Day 2 (48 ± 2 hr post EOI) | X |
| Day 3 (72 ± 3 hr post EOI) | X |
| Day 4 (96 ± 3 hr post EOI) | X |
| Day 7 | X |
| Day 9 | X |
| Day 11 | X |
| Day 14 | X |
| Day 21 | X |
| Day 28 | X |
| Day 42 | X |
| Day 56 | X |

[1] Adipokines/cytokines are analyzed using samples collected at some or all of the PK time points. Measured adipokines/cytokines may include, for example, adiponectin, resistin, leptin, visfatin, PAI-1, TNFα, IL-1, IL-1Ra, IL-6, IL-8, RANTES, and MCP-1.
EOI = end of infusion Based on results obtained from the first clinical study, additional clinical trials are performed. Such trials may include one or more of the above dosages and dosing regimens, as well as or alternatively one or more other dosages of IL-1β antibody, longer treatment and/or observation periods and greater numbers of patients per group (e.g., at least about 10, 50, 100, 200, 300, 400, 500, 750, 1000)

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Wherever an open-ended term is used to describe a feature or element of the invention, it is specifically contemplated that a closed-ended term can be used in place of the open-ended term without departing from the spirit and scope of the invention. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those working in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating gout in a subject, the method comprising administering an anti-IL-1β antibody or fragment thereof to the subject, wherein the antibody or antibody fragment is administered in a dose of 0.03 mg/kg to 1 mg/kg of antibody or fragment.

2. The method of claim 1, wherein the gout is chronic gout.

3. The method of claim 1, wherein the gout is acute gout.

4. The method of claim 1, wherein the anti-IL-1β antibody or antibody fragment is a neutralizing antibody.

5. The method of claim 1, wherein the anti-IL-1β antibody or antibody fragment binds to an IL-1β epitope such that the bound antibody or fragment substantially permits the binding of IL-1β to IL-1 receptor I (IL-1RI).

6. The method of claim 1, wherein the antibody or antibody fragment does not detectably bind to IL-1α, IL-1R or IL-1Ra.

7. The method of claim 1, wherein the antibody or fragment thereof competes with the binding of an antibody having the light chain variable region of SEQ ID NO:5 and the heavy chain variable region of SEQ ID NO:6.

8. The method of claim 1, wherein the antibody or antibody fragment is human engineered or humanized.

9. The method of claim 1, wherein the antibody or antibody fragment is human.

10. The method of claim 1, wherein the anti-IL-1β antibody or fragment is administered by subcutaneous, intravenous or intramuscular injection.

11. The method of claim 1, wherein said method is in conjunction with at least one additional treatment method, said additional treatment method comprising administering at least one pharmaceutical composition comprising an active agent other than an IL-1β antibody or fragment.

12. The method of claim 11, wherein said at least one pharmaceutical composition comprising an active agent other than an IL-1β antibody or fragment is selected from the group consisting of a nonsteroidal anti-inflammatory drug (NSAID), a corticosteroid, an adrenocorticotropic hormone, and a colchicine.

13. The method of claim 1, wherein the antibody or fragment thereof has a lower $IC_{50}$ than an IL-1 receptor antagonist in a human whole blood IL-1β inhibition assay that measures IL-1β induced production of IL-8.

14. The method of claim 13, wherein the IL-1 receptor antagonist is anakinra.

15. The method of claim 1, wherein the antibody or antibody fragment binds to human IL-1β with a dissociation constant of about 10 nM or less.

16. The method of claim 15, wherein the antibody or antibody fragment binds to human IL-1β with a dissociation constant of about 1 nM or less.

17. The method of claim 16, wherein the antibody or antibody fragment binds to human IL-1β with a dissociation constant of about 100 pM or less.

18. The method of claim 17, wherein the antibody or antibody fragment binds to human IL-1β with a dissociation constant of about 10 pM or less.

19. The method of claim 18, wherein the antibody or antibody fragment binds to human IL-1β with a dissociation constant of about 1 pM or less.

20. The method of claim 19, wherein the antibody or antibody fragment binds to human IL-1β with a dissociation constant of about 0.3 pM or less.

* * * * *

SEQUENCE LISTING

<160> NUMBER OF SEQ ID NOS: 6

<210> SEQ ID NO 1
<211> LENGTH: 23
<212> TYPE: PRT
<213> ORGANISM: Artificial
<220> FEATURE:
<223> OTHER INFORMATION: Synthesized- epitope

<400> SEQUENCE: 1

Glu Ser Val Asp Pro Lys Asn Tyr Pro Lys Lys Met Glu Lys Arg
1               5                   10                  15

Phe Val Phe Asn Lys Ile Glu
            20

<210> SEQ ID NO 2
<211> LENGTH: 5
<212> TYPE: PRT
<213> ORGANISM: Artificial
<220> FEATURE:
<223> OTHER INFORMATION: Synthesized- linker

<400> SEQUENCE: 2

Gly Gly Gly Gly Ser
1               5

<210> SEQ ID NO 3
<211> LENGTH: 107
<212> TYPE: PRT
<213> ORGANISM: Artificial
<220> FEATURE:
<223> OTHER INFORMATION: Synthesized- AB5 light chain varaible region

<400> SEQUENCE: 3

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Ser Trp Tyr Gln Gln Lys Pro Asp Gly Thr Val Lys Leu Leu Ile
        35                  40                  45

Tyr Tyr Thr Ser Lys Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Leu Gln Gly Lys Met Leu Pro Trp
                85                  90                  95

Thr Phe Gly Gly Gly Thr Lys Leu Glu Ile Lys
            100                 105

<210> SEQ ID NO 4
<211> LENGTH: 120
<212> TYPE: PRT
<213> ORGANISM: Artificial
<220> FEATURE:
<223> OTHER INFORMATION: Synthesized- AB5 heavy chain variable region

<400> SEQUENCE: 4

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

```
Gly Met Gly Val Gly Trp Ile Arg Gln Pro Ser Gly Lys Gly Leu Glu
            35                  40                  45

Trp Leu Ala His Ile Trp Trp Asp Gly Asp Glu Ser Tyr Asn Pro Ser
     50                  55                  60

Leu Lys Thr Gln Leu Thr Ile Ser Lys Asp Thr Ser Arg Asn Gln Val
 65                  70                  75                  80

Phe Leu Lys Ile Thr Ser Val Asp Thr Val Thr Ala Thr Tyr Phe
                 85                  90                  95

Cys Ala Arg Asn Arg Tyr Asp Pro Pro Trp Phe Val Asp Trp Gly Gln
            100                 105                 110

Gly Thr Leu Val Thr Val Ser Ser
            115                 120

<210> SEQ ID NO 5
<211> LENGTH: 107
<212> TYPE: PRT
<213> ORGANISM: Artificial
<220> FEATURE:
<223> OTHER INFORMATION: Synthesized- AB7 light chain variable region

<400> SEQUENCE: 5

Asp Ile Gln Met Thr Gln Ser Thr Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ser Trp Tyr Gln Gln Lys Pro Gly Lys Ala Val Lys Leu Leu Ile
        35                  40                  45

Tyr Tyr Thr Ser Lys Leu His Ser Gly Val Pro Ser Arg Phe Ser Gly
 50                  55                  60

Ser Gly Ser Gly Thr Asp Tyr Thr Leu Thr Ile Ser Ser Leu Gln Gln
65                  70                  75                  80

Glu Asp Phe Ala Thr Tyr Phe Cys Leu Gln Gly Lys Met Leu Pro Trp
                85                  90                  95

Thr Phe Gly Gln Gly Thr Lys Leu Glu Ile Lys
            100                 105

<210> SEQ ID NO 6
<211> LENGTH: 120
<212> TYPE: PRT
<213> ORGANISM: Artificial
<220> FEATURE:
<223> OTHER INFORMATION: Synthesized- AB7 heavy chain variable region

<400> SEQUENCE: 6

Gln Val Gln Leu Gln Glu Ser Gly Pro Gly Leu Val Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Glu Ser Tyr Asn Pro Ser
 50                  55                  60

Leu Lys Ser Arg Leu Thr Ile Ser Lys Asp Thr Ser Lys Asn Gln Val
65                  70                  75                  80
```

```
Ser Leu Lys Ile Thr Ser Val Thr Ala Ala Asp Thr Ala Val Tyr Phe
            85              90              95

Cys Ala Arg Asn Arg Tyr Asp Pro Pro Trp Phe Val Asp Trp Gly Gln
            100             105             110

Gly Thr Leu Val Thr Val Ser Ser
        115             120
```